US011083707B2

(12) United States Patent
Kesteleyn et al.

(10) Patent No.: US 11,083,707 B2
(45) Date of Patent: Aug. 10, 2021

(54) SUBSTITUTED INDOLINE DERIVATIVES AS DENGUE VIRAL REPLICATION INHIBITORS

(71) Applicants: JANSSEN PHARMACEUTICALS, INC., Titusville, NJ (US); KATHOLIEKE UNIVERSITEIT LEUVEN, Leuven (BE)

(72) Inventors: Bart Rudolf Romanie Kesteleyn, Beerse (BE); Jean-François Bonfanti, Issy-les-Moulineaux (FR); Erwin Coesemans, Beerse (BE); Pierre Jean-Marie Bernard Raboisson, Beerse (BE); Arnaud Didier M Marchand, Leuven (BE); Dorothée Alice Marie-Eve Bardiot, Leuven (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/493,768

(22) PCT Filed: Mar. 29, 2018

(86) PCT No.: PCT/EP2018/058079
§ 371 (c)(1),
(2) Date: Sep. 13, 2019

(87) PCT Pub. No.: WO2018/178240
PCT Pub. Date: Oct. 4, 2018

(65) Prior Publication Data
US 2020/0121647 A1    Apr. 23, 2020

(30) Foreign Application Priority Data
Mar. 31, 2017 (EP) .................................... 17164048

(51) Int. Cl.
| A61P 31/14 | (2006.01) |
| A61P 31/12 | (2006.01) |
| C07D 403/12 | (2006.01) |
| A61K 31/4196 | (2006.01) |
| A61K 45/06 | (2006.01) |

(52) U.S. Cl.
CPC .......... *A61K 31/4196* (2013.01); *A61K 45/06* (2013.01); *A61P 31/14* (2018.01); *C07D 403/12* (2013.01)

(58) Field of Classification Search
CPC ........ A61P 31/14; A61P 31/12; C07D 403/12; A61K 31/4196; A61K 45/06
See application file for complete search history.

(56) References Cited

U.S. PATENT DOCUMENTS

| 6,177,426 B1 | 1/2001 | Denney et al. |
| 7,601,735 B2 | 10/2009 | Tyms et al. |
| 8,143,259 B2 | 3/2012 | Colburn et al. |
| 8,299,056 B2 | 10/2012 | Bahmanyar et al. |
| 8,324,217 B2 | 12/2012 | Colburn et al. |
| 8,524,764 B2 | 9/2013 | Canales et al. |
| 8,884,030 B2 | 11/2014 | Canales et al. |
| 8,993,604 B2 | 3/2015 | Byrd et al. |
| 9,029,376 B2 | 5/2015 | Byrd et al. |
| 9,522,923 B2 | 12/2016 | Richards et al. |
| 9,944,598 B2 | 4/2018 | Kesteleyn et al. |
| 10,029,984 B2 | 7/2018 | Kesteleyn et al. |
| 10,064,870 B2 | 9/2018 | Rajagopalan et al. |
| 10,071,961 B2 | 9/2018 | Vandyck et al. |
| 10,117,850 B2 | 11/2018 | Griffioen et al. |
| 10,209,902 B1 | 2/2019 | Kesteleyn et al. |
| 10,323,026 B2 | 6/2019 | Ikeda et al. |
| 2005/0239821 A1 | 10/2005 | Neyts et al. |
| 2006/0194835 A1 | 8/2006 | Dugourd et al. |
| 2006/0211698 A1 | 9/2006 | Botyanszki et al. |
| 2008/0318338 A1 | 12/2008 | Kamal et al. |
| 2013/0023532 A1 | 1/2013 | Casillas et al. |
| 2014/0213586 A1 | 7/2014 | Bardiot et al. |
| 2016/0297810 A1 | 10/2016 | Bardiot et al. |
| 2017/0002006 A1 | 1/2017 | Corte et al. |
| 2017/0096429 A1 | 4/2017 | Corte et al. |
| 2017/0281633 A1 | 10/2017 | Boylan et al. |
| 2017/0281766 A1 | 10/2017 | Wiltzius |

(Continued)

FOREIGN PATENT DOCUMENTS

| JP | 2012-206959 A | 10/2012 |
| WO | 99-21559 A1 | 5/1999 |

(Continued)

OTHER PUBLICATIONS

Japanese Office Action dated Jun. 2, 2020 from Japanese Patent Appln. No. JP2017-243354 (English language translation).

(Continued)

*Primary Examiner* — Sun Jae Yoo
(74) *Attorney, Agent, or Firm* — Burns & Levinson, LLP; Shawn P. Foley

(57) ABSTRACT

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

15 Claims, No Drawings

Specification includes a Sequence Listing.

(56) References Cited

U.S. PATENT DOCUMENTS

| | | |
|---|---|---|
| 2017/0283500 A1 | 10/2017 | Wiltzius et al. |
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |
| 2019/0183931 A1 | 6/2019 | Bakker et al. |

FOREIGN PATENT DOCUMENTS

| | | | |
|---|---|---|---|
| WO | 02089780 | A2 | 11/2002 |
| WO | 03050295 | A2 | 6/2003 |
| WO | 2006076529 | A1 | 7/2006 |
| WO | 2009149054 | A1 | 12/2009 |
| WO | 2010021878 | A1 | 2/2010 |
| WO | 2010027500 | A1 | 3/2010 |
| WO | 2010091413 | A1 | 8/2010 |
| WO | 2011037643 | A2 | 3/2011 |
| WO | 2011088303 | A1 | 7/2011 |
| WO | 2011-120025 | A1 | 9/2011 |
| WO | 2013045516 | A1 | 4/2013 |
| WO | 2014154682 | A1 | 10/2014 |
| WO | 2016050831 | A1 | 4/2016 |
| WO | 2016050841 | A1 | 4/2016 |
| WO | 2016053455 | A1 | 4/2016 |
| WO | 2017046255 | A1 | 3/2017 |
| WO | 2017046258 | A1 | 3/2017 |
| WO | 2017079216 | A1 | 5/2017 |
| WO | 2017167832 | A1 | 10/2017 |
| WO | 2017167950 | A1 | 10/2017 |
| WO | 2017167951 | A1 | 10/2017 |
| WO | 2017167952 | A1 | 10/2017 |
| WO | 2017167953 | A1 | 10/2017 |
| WO | 2017171100 | A1 | 10/2017 |
| WO | 2017173206 | A1 | 10/2017 |
| WO | 2017173256 | A1 | 10/2017 |
| WO | 2017173384 | A1 | 10/2017 |
| WO | 2017173410 | A1 | 10/2017 |
| WO | 2018178238 | A1 | 10/2018 |
| WO | 2018178240 | A1 | 10/2018 |
| WO | 2018215315 | A1 | 11/2018 |
| WO | 20188215316 | A1 | 11/2018 |

OTHER PUBLICATIONS

ACS on STN Registry No. 931079-09-3, Apr. 20, 2007.
ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.
EP Search Report dated Nov. 19, 2019 from European Patent Appln. No. EP 19183201.3.
"Solvation," Wikipedia, at Internet address: https://en.wikipedia.org/wiki/Solvation, web page last edited on Mar. 13, 2019, 6 pages.
Examination Report dated Jan. 7, 2020 from Indian Patent Appln. No. 201727014547.
PCT International Search Report and Written Opinion dated Jun. 8, 2018 in connection with PCT International Application No. PCT/EP2018/058079.
Prasad L. Polavarapu, et al., Intrinsic Rotation and Molecular Structure, Chirality 15: S143-S149 (2003).
Prevention, Dengue, Centers for Disease Control and Prevention (Sep. 27, 2012) https://www.cdc.govidengue/prevention/index.html, internet.
Lidia Moreira Lima et al., Bioisosterism: A Useful Strategy for Molecular Modification and Drug Design, Current Medicinal Chemistry, Bentham Science Publishers Ltd. (2005) 12, pp. 23-49.
Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65) (translation).
Wolff et al., Burger's Medicinal Chemistry and Drug Discovery, 5th Ed. part 1, p. 975-977 (1995).
Banker, et al., (1996) Modern Pharmaceuticals, 3rd Edition, Revised and Expanded, p. 596.

SEQUENCE LISTING

<160> NUMBER OF SEQ ID NOS: 6

<210> SEQ ID NO 1
<211> LENGTH: 19
<212> TYPE: DNA
<213> ORGANISM: Dengue virus group

<400> SEQUENCE: 1
cggttagagg agacccctc                                                    19

<210> SEQ ID NO 2
<211> LENGTH: 21
<212> TYPE: DNA
<213> ORGANISM: Dengue virus group

<400> SEQUENCE: 2
gagacagcag gatctctggt c                                                 21

<210> SEQ ID NO 3
<211> LENGTH: 28
<212> TYPE: DNA
<213> ORGANISM: Dengue virus group

<400> SEQUENCE: 3
aaggactaga ggttagagga gaccccccc                                          28

<210> SEQ ID NO 4
<211> LENGTH: 18
<212> TYPE: DNA
<213> ORGANISM: Dengue virus group

<400> SEQUENCE: 4
ggccaggtca tcaccatt                                                      18

<210> SEQ ID NO 5
<211> LENGTH: 21
<212> TYPE: DNA
<213> ORGANISM: Dengue virus group

<400> SEQUENCE: 5
atgtccacgt cacacttcat g                                                 21

<210> SEQ ID NO 6
<211> LENGTH: 21
<212> TYPE: DNA
<213> ORGANISM: Dengue virus group

<400> SEQUENCE: 6
ttccgctgcc ctgaggctct c                                                 21

SUBSTITUTED INDOLINE DERIVATIVES AS DENGUE VIRAL REPLICATION INHIBITORS

CROSS-REFERENCE TO RELATED APPLICATIONS

This application is a U.S. national stage entry under 35 U.S.C. § 371 of PCT International Patent Application No. PCT/EP2018/058079, filed Mar. 29, 2018, which claims priority to European Patent Application No. 17164048.5, filed Mar. 31, 2017, the contents of which are incorporated herein by reference in their entirety.

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Although progress is being made in the development of vaccines against dengue with the availability of the Dengvaxia® vaccine, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes.

Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases. WO-2013/045516 discloses indole and indoline derivatives for use in the treatment of dengue viral infections.

The present invention now provides compounds, substituted indoline derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision compounds of formula (I), including any stereochemically isomeric form thereof:

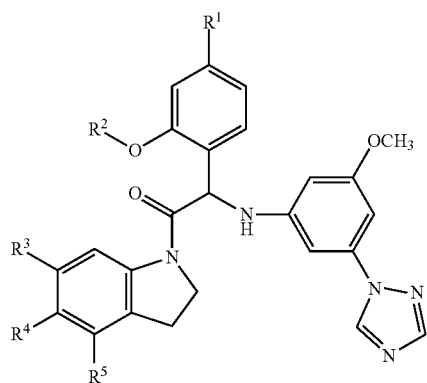

(I)

wherein
R¹ is chloro or fluoro,
R² is —CH₂CH₂OH, or C₃₋₅alkylCOOH;
R³ is trifluoromethyl, or trifluoromethoxy;
R⁴ is hydrogen, fluoro, or methoxy; and
R⁵ is hydrogen or methyl;
or a pharmaceutically acceptable salt, solvate or polymorph thereof.

The term "C₃₋₅alkyl" as used herein defines straight and branched chain saturated hydrocarbon radicals having from 3 to 5 carbon atoms such as, for example, propyl, butyl, pentyl, 1,1-dimethylpropyl, 2-methylpropyl, 2-methylbutyl and the like.

Specifically above mentioned compounds are selected from the group comprising:

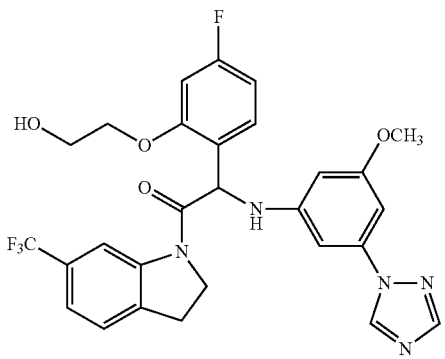 [SMILES: COc1cc(NC(C(=O)N2CCc3ccc(C(F)(F)F)cc32)c2ccc(F)cc2OCCO)cc(-n2cncn2)c1]

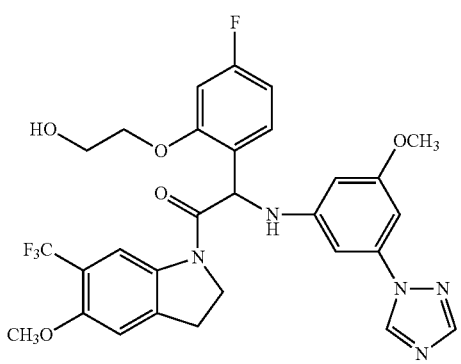

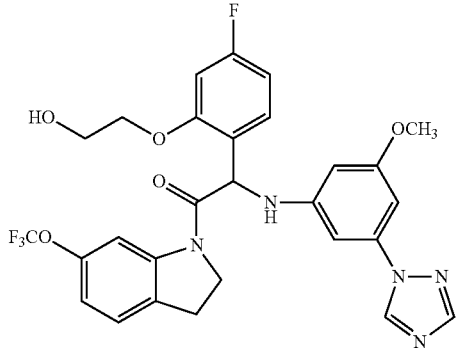

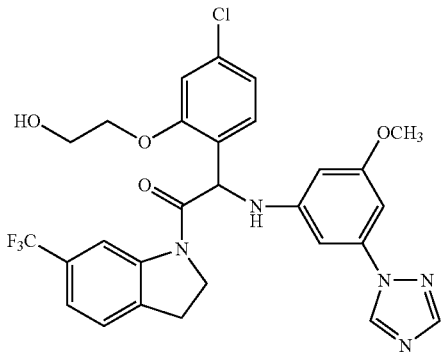

-continued
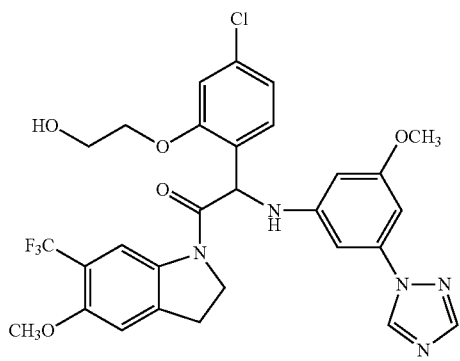
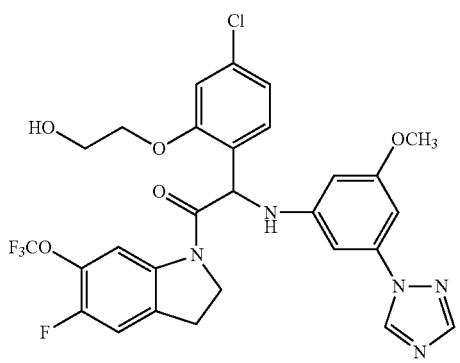
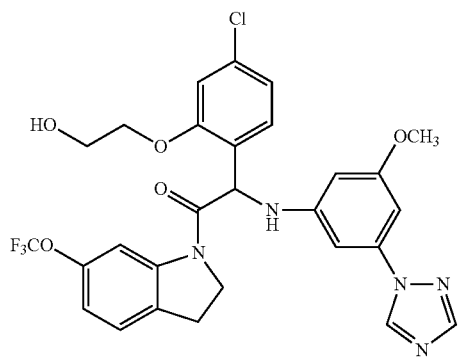
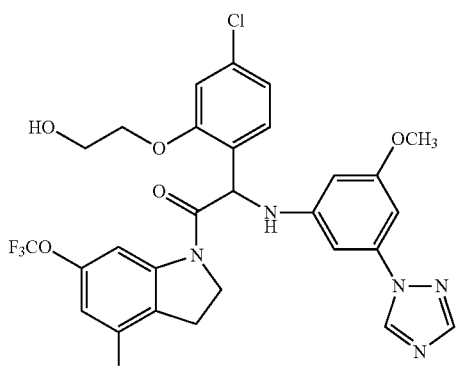
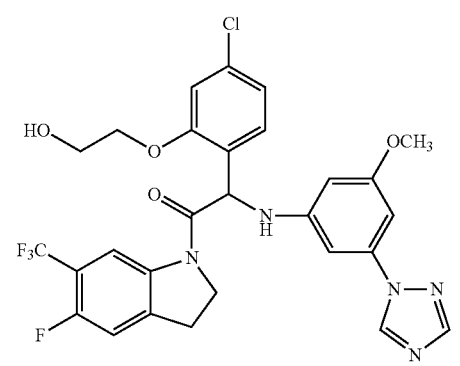
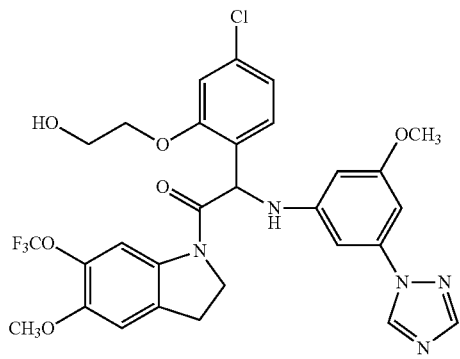
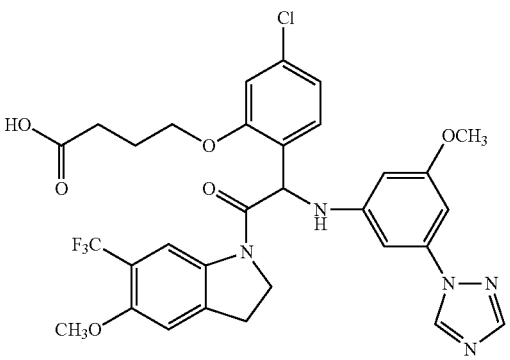

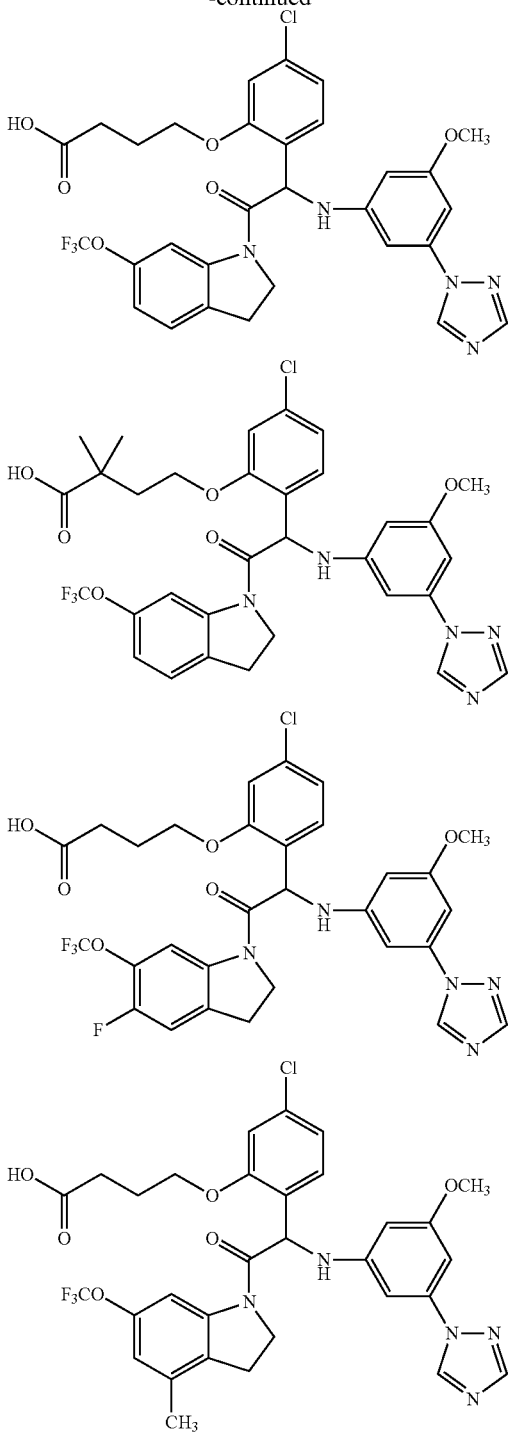

Part of the current invention is also a pharmaceutical composition comprising a compound mentioned above or a stereoisomeric form, a pharmaceutically acceptable salt, solvate or polymorph thereof together with one or more pharmaceutically acceptable excipients, diluents or carriers.

Pharmaceutically acceptable salts of said compounds include the acid addition and base salts thereof. Suitable acid addition salts are formed from acids which form non-toxic salts. Suitable base salts are formed from bases which form non-toxic salts.

The pharmaceutically acceptable acid salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-amino-salicylic, pamoic acid and the like acids.

The compounds of the invention may also exist in un-solvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of the invention used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The compounds of formula (I) of the present invention all have at least one chiral carbon atom as indicated in the figure below by the carbon atom labelled with *:

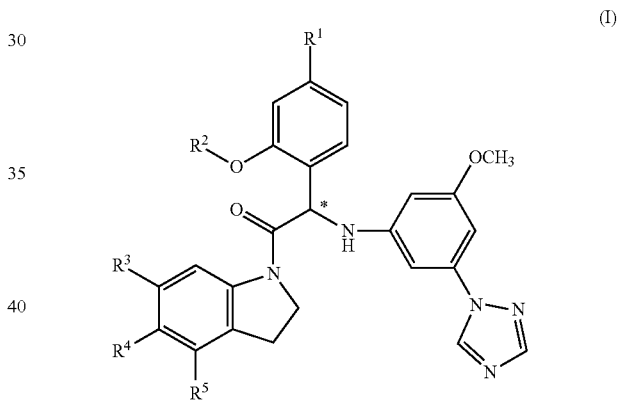

(I)

Due to the presence of said chiral carbon atom, a "compound of formula (I)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)-after measuring the specific optical rotation of said particular enantiomer.

In an aspect the present invention relates to a first group of compound of formula (I) wherein the compounds of formula (I) have the (+) specific rotation.

In a further aspect the present invention relates to a second ground of compounds of formula (I) wherein the compounds of formula (I) have the (−) specific rotation.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes).

| Method Code | Instrument | Column | Mobile phase | Gradient | Flow / Col T | Run time (min) |
|---|---|---|---|---|---|---|
| LC-A | Waters: Acquity ® UPLC ® - DAD- Quattro Micro ™ | Waters: BEH ® C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 mL/min / 40° C. | 6.2 |
| LC-B | Waters: Acquity ® H-Class - DAD and SQD2TM | Waters: BEH ® C18 (1.7 μm, 2.1 × 100 mm) | A: 95% $CH_3COONH_4$ 7 mM/5% $CH_3CN$, B: $CH_3CN$ | 84.2% A/15.8% B to 10.5% A in 2.18 min, held for 1.96 min, back to 84.2% A/ 15.8% B in 0.73 min, held for 0.49 min. | 0.343 mL/min / 40° C. | 6.1 |
| LC-C | Waters: Acquity ® UPLC ® -DAD- SQD | Waters: BEH C18 (1.7 μm, 2.1 × 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 mL/min / 55° C. | 2 |
| LC-D | Waters: Acquity ® UPLC ® -DAD- SQD | Waters: HSS T3 (1.8 μm, 2.1 × 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min / 55° C. | 3.5 |

SFC/MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow / Col T | Run time / BPR |
|---|---|---|---|---|---|
| SFC-A | Daicel Chiralpak ® IA column (5 μm, 150 × 4.6 mm) | A: $CO_2$<br>B: EtOH (+0.3% $iPrNH_2$) | 30% B hold 7 min, | 3 / 35 | 7 / 100 |
| SFC-B | Daicel Chiralpak ® AD-H column (5 μm, 150 × 4.6 mm) | A: $CO_2$<br>B: EtOH (+0.3% $iPrNH_2$) | 30% B hold 7 min, | 3 / 35 | 7 / 100 |
| SFC-C | Daicel Chiralpak ® AD-H column (5 μm, 150 × 4.6 mm) | A: $CO_2$<br>B: EtOH (+0.3% $iPrNH_2$) | 40% B hold 7 min, | 3 / 35 | 7 / 100 |
| SFC-D | Daicel Chiralpak ® IC column (5 μm, 150 × 4.6 mm) | A: $CO_2$<br>B: EtOH (+0.3% $iPrNH_2$) | 25% B hold 7 min, | 3 / 35 | 7 / 100 |
| SFC-E | Daicel Chiralpak ® IC column (5 μm, 150 × 4.6 mm) | A: $CO_2$<br>B: EtOH (+0.3% $iPrNH_2$) | 30% B hold 7 min, | 3 / 35 | 7 / 100 |
| SFC-F | Daicel Chiralpak ® AD-3 column (3 μm, 100 × 4.6 mm) | A: $CO_2$<br>B: EtOH (+0.3% $iPrNH_2$) | 30% B hold 3 min, | 3.5 / 35 | 3 / 103 |
| SFC-G | Daicel Chiralpak ® AD-H column (5 μm, 150 × 4.6 mm) | A: $CO_2$<br>B: EtOH | 30% B hold 7 min, | 3 / 35 | 7 / 100 |
| SFC-H | Daicel Chiralpak ® AS-3 column (3 μm, 100 × 4.6 mm) | A: $CO_2$<br>B: iPrOH (+0.3% $iPrNH_2$) | 20% B hold 10 min, | 3.5 / 35 | 10 / 103 |
| SFC-I | Daicel Chiralpak ® AS-3 column (3 μm, 100 × 4.6 mm) | A: $CO_2$<br>B: EtOH (+0.3% $iPrNH_2$) | 10% B hold 10 min, | 3.5 / 35 | 10 / 103 |
| SFC-J | Daicel Chiralcel ® OD-3 column (3 μm, 100 × 4.6 mm) | A: $CO_2$<br>B: MeOH (+0.3% $iPrNH_2$) | 20% B hold 6 min, | 3.5 / 35 | 6 / 103 |
| SFC-K | Daicel Chiralpak ® AS3 column (3.0 μm, 150 × 4.6 mm) | A: $CO_2$<br>B: EtOH (+0.2% $iPrNH_2$ +3% $H_2O$) | 10%-50% B in 6 min, hold 3.5 min | 2.5 / 40 | 9.5 / 110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: $[\alpha]°$ ($\lambda$, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Abbreviations Used in Experimental Part

| | |
|---|---|
| (M + H)+ | protonated molecular ion |
| aq. | aqueous |
| Boc | tert-butyloxycarbonyl |
| Boc$_2$O | di-tert-butyl dicarbonate |
| br | broad |
| CH$_3$CN | acetonitrile |
| CHCl$_3$ | chloroform |
| CH$_2$Cl$_2$ | dichloromethane |
| CH$_3$OH | methanol |
| CO$_2$ | carbon dioxide |
| d | doublet |
| DCM | dichloromethane |
| DIEA | diisopropylethylamine |
| DIPE | diisopropyl ether |
| DMA | dimethylacetamide |
| DMAP | 4-dimethylaminopyridine |
| DME | 1,2-dimethoxyethane |
| DMF | dimethylformamide |
| DMSO | dimethyl sulfoxide |
| eq. | equivalent |
| Et$_2$O | diethyl ether |
| Et$_3$N | triethylamine |
| EtOAc | ethyl acetate |
| EtOH | ethanol |
| H$_2$O | water |
| H$_2$SO$_4$ | sulfuric acid |
| HATU | O-(7-aza-1H-benzotriazol-1-yl)-N,N,N',N'-tetramethyl-uronium hexafluorophosphate-CAS [148893-10-1] |
| HCl | hydrochloric acid |
| HPLC | high performance liquid chromatography |
| iPrNH$_2$ | isopropylamine |
| iPrOH | 2-propanol |
| K$_2$CO$_3$ | potassium carbonate |
| LiAlH$_4$ | lithium aluminium hydride |
| m/z | mass-to-charge ratio |
| Me | methyl |
| MeOH | methanol |
| MgSO$_4$ | magnesium sulfate |
| min | minute(s) |
| N$_2$ | nitrogen |
| Na$_2$CO$_3$ | sodium carbonate |
| Na$_2$SO$_4$ | sodium sulfate |
| NaBH$_4$ | sodium borohydride |
| NaHCO$_3$ | sodium bicarbonate |
| NaOH | sodium hydroxide |
| NH$_4$Cl | ammonium chloride |
| q | quartet |
| rt or RT | room temperature |
| s | singlet |
| t | triplet |
| tBuOK | potassium tert-butanolaat |
| TEA | triethylamine |
| TFA | trifluoroacetic acid |
| THF | tetrahydrofuran |
| TMSCl | trimethylsilyl chloride |

Example 1: Synthesis of 2-(4-fluoro-2-(2-hydroxy-ethoxy)phenyl)-2-((3-methoxy-5-(1H-1,2,4-triazol-1-yl)phenyl)amino)-1-(6-(trifluoromethyl)indolin-1-yl)ethanone (Compound 1) and Chiral Separation into Enantiomers 1A and 1B

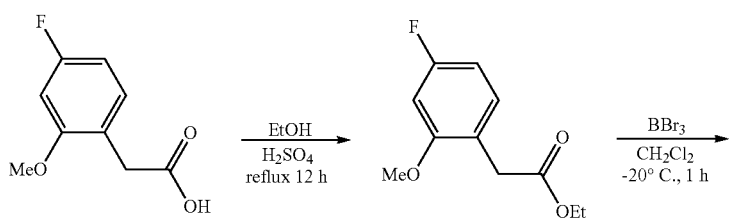

1a

-continued
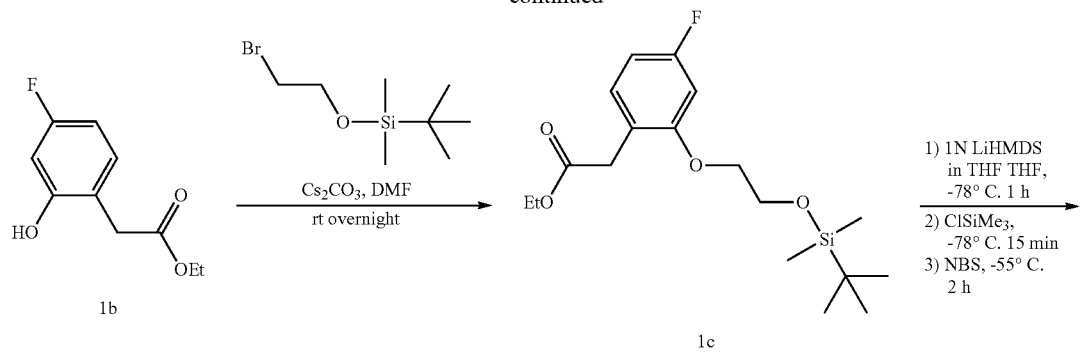
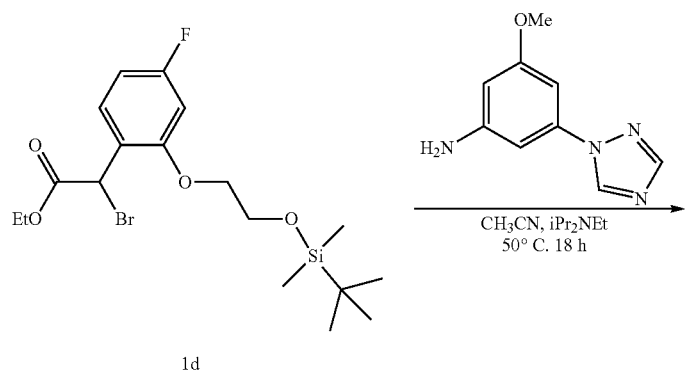
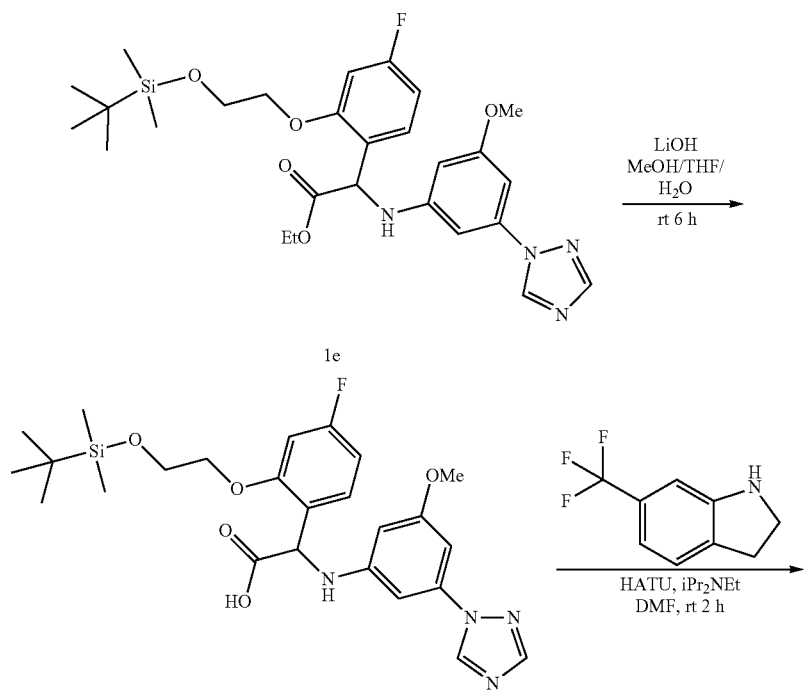

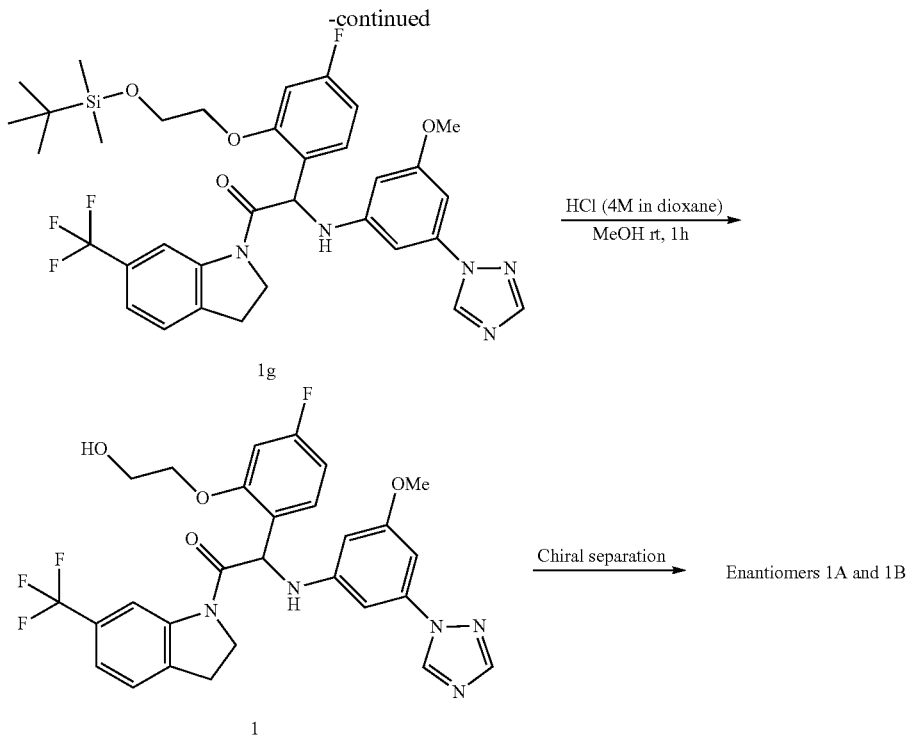

Synthesis of Intermediate 1a

A solution of 4-fluoro-2-methoxyphenylacetic acid [CAS 886498-61-9] (10 g, 54.3 mmol) in EtOH (200 mL) and $H_2SO_4$ (2 mL) was heated under reflux for 12 h. Water was added and the mixture was concentrated under reduced pressure to half of the original volume. Ice was added. The solution was basified with $K_2CO_3$ and extracted with EtOAc. The organic layer was washed with brine, dried over $MgSO_4$, filtered and the solvent was concentrated under reduced pressure to give ethyl 2-(4-fluoro-2-methoxyphenyl)acetate 1a (11.6 g). The compound was used directly in the next step.

Synthesis of Intermediate 1b

A 1M solution of boron tribromide in $CH_2Cl_2$ (109.3 mL, 109.3 mmol) was added dropwise to a solution of ethyl 2-(4-fluoro-2-methoxyphenyl)acetate 1a (11.6 g, 54.7 mmol) in $CH_2Cl_2$ (300 mL) at −30° C. The reaction was stirred at −20° C. for 1 h, and then quenched with $CH_3OH$. The pH was adjusted to 8 by adding a saturated water solution of $NaHCO_3$. The solution was extracted with $CH_2Cl_2$ and the combined organic layers were dried over $MgSO_4$, filtered and the solvent was concentrated under reduced pressure to give ethyl 2-(4-fluoro-2-hydroxyphenyl)acetate 1b (10.8 g). The compound was used directly in the next step without further purification.

Synthesis of Intermediate 1c

To a mixture of ethyl 2-(4-fluoro-2-hydroxyphenyl)acetate 1b (10.6 g, 53.5 mmol) and cesium carbonate (34.8 g, 106.9 mmol) in DMF (200 mL) at 10° C. was added (2-bromoethoxy)(tert-butyl)dimethylsilane [CAS 86864-60-0] (13.8 mL, 64.2 mmol). The reaction mixture was stirred at room temperature overnight. $H_2O$ was added and the reaction mixture was extracted with EtOAc. The organic phase was dried over $MgSO_4$, filtered and concentrated under reduced pressure. The residue was purified by flash chromatography on silica gel (15-40 μM, 40 g, heptane/EtOAc 80/20). The pure fractions were combined and the solvent was removed under reduced pressure to give ethyl 2-(2-(2-((tert-butyldimethylsilyl)oxy)ethoxy)-4-fluorophenyl)acetate 1c (17.7 g).

Synthesis of Intermediate 1d

To a 1M lithium bis(trimethylsilyl)amide solution in THF (28.05 mL, 28.05 mmol), cooled at −78° C., was added a solution of ethyl 2-(2-(2-((tert-butyldimethylsilyl)oxy)ethoxy)-4-fluorophenyl)acetate 1c (5 g, 14.03 mmol) in THF (30 mL). After stirring for 1 h at −78° C., chlorotrimethylsilane (2.85 mL, 22.4 mmol) was added. The reaction mixture was stirred at −78° C. for 15 min. N-Bromosuccinimide (3 g, 16.8 mmol) in THF (30 mL) was added and stirring was continued at −55° C. for 2 h. The reaction mixture was poured out into $H_2O$ and extracted twice with EtOAc. The organic phases were combined, dried over $MgSO_4$, filtered and concentrated under reduced pressure to give ethyl 2-bromo-2-(2-(2-((tert-butyldimethylsilyl)oxy)ethoxy)-4-fluorophenyl)acetate 1d (6.57 g) which was used in the next step without further purification.

Synthesis of Intermediate 1e

A mixture of ethyl 2-bromo-2-(2-(2-((tert-butyldimethylsilyl)oxy)ethoxy)-4-fluorophenyl)acetate 1d (3.1 g, 7.12 mmol), 3-methoxy-5-(1H-1,2,4-triazol-1-yl)aniline [CAS 1220630-56-7] (2.03 g, 10.7 mmol) and diisopropylethylamine (2.45 mL, 14.2 mmol) in $CH_3CN$ (60 mL) was stirred at 50° C. for 18 h. The reaction mixture was concentrated under reduced pressure. The residue was taken up with EtOAc and washed with 0.5N HCl, water and brine. The organic phase was dried over MgSO$_4$, filtered and concentrated under reduced pressure. The residue was purified by flash chromatography on silica gel (15-40 μm, 120 g, heptane/EtOAc gradient 80/20 to 60/40) to give ethyl 2-(2-(2-((tert-butyldimethylsilyl)oxy)ethoxy)-4-fluorophenyl)-2-((3-methoxy-5-(1H-1,2,4-triazol-1-yl)phenyl)amino)acetate 1e (2.5 g).

Synthesis of Intermediate 1f

A solution of lithium hydroxide monohydrate (226 mg, 5.397 mmol) in water (25 mL) was added portionwise to a solution of ethyl 2-(2-(2-((tert-butyldimethylsilyl)oxy)ethoxy)-4-fluorophenyl)-2-((3-methoxy-5-(1H-1,2,4-triazol-1-yl)phenyl)amino)acetate 1e (2.45 g, 4.498 mmol) in a solvent mixture of THF/CH$_3$OH (1/1) (50 mL) at 10° C. The reaction was stirred at room temperature for 6 h, diluted with water and cooled to 0° C. The solution was slowly acidified with 0.5N HCl to pH 6, and extracted with EtOAc. The organic layer was dried over MgSO$_4$, filtered and the solvent was concentrated under reduced pressure to give 2-(2-(2-((tert-butyldimethylsilyl)oxy)ethoxy)-4-fluorophenyl)-2-((3-methoxy-5-(1H-1,2,4-triazol-1-yl)phenyl)amino)acetic acid 1f (2.05 g). The compound was used directly in the next step without further purification.

Synthesis of Intermediate 1g

To a solution of 2-(2-(2-((tert-butyldimethylsilyl)oxy)ethoxy)-4-fluorophenyl)-2-((3-methoxy-5-(1H-1,2,4-triazol-1-yl)phenyl)amino)acetic acid 1f (1.58 g, 3.06 mmol) in DMF (20 mL) were added HATU (1.74 g, 4.60 mmol), diisopropylethylamine (1.5 mL, 9.17 mmol) and 6-(trifluoromethyl)indoline [CAS 181513-29-1] (572 mg, 3.06 mmol). The reaction mixture was stirred at room temperature for 2 h. The reaction mixture was diluted with water. The precipitate was filtered off, washed with water and taken up with EtOAc. The organic layer was washed with a 10% solution of K$_2$CO$_3$ in water, water, dried over MgSO$_4$, filtered and the solvent was concentrated under reduced pressure to give 2-(2-(2-tert-butyldimethylsilyl)oxy)ethoxy)-4-fluorophenyl)-2-((3-methoxy-5-(1H-1,2,4-triazol-1-yl)phenyl)amino)-1-(6-(trifluoromethyl)indolin-1-yl)ethanone 1g (2.1 g). The crude compound was used directly in the next step.

Synthesis of Compound 1 and Chiral Separation into Enantiomers 1A and 1B

Under a N$_2$ flow, at 5° C., 4M HCl in dioxane (7.65 mL, 30.6 mmol) was added dropwise to a solution of 2-(2-(2-((tert-butyldimethylsilyl)oxy)ethoxy)-4-fluorophenyl)-2-((3-methoxy-5-(1H-1,2,4-triazol-1-yl)phenyl)amino)-1-(6-(trifluoromethyl)indolin-1-yl)ethanone 1g (2.1 g, 3.06 mmol) in MeOH (40 mL). The reaction was stirred at room temperature for 1 h. The mixture was cooled to 0° C., basified with a 10% aqueous solution of K$_2$CO$_3$ and extracted with EtOAc. The organic phase was separated, dried over MgSO$_4$, filtered and the solvent was concentrated under reduced pressure. The residue was crystallized from CH$_3$CN/diisopropyl ether to give 2-(4-fluoro-2-(2-hydroxyethoxy)phenyl)-2-((3-methoxy-5-(1H-1,2,4-triazol-1-yl)phenyl)amino)-1-(6-(trifluoromethyl)indolin-1-yl)ethanone 1 (800 mg) as a racemate.

The enantiomers of Compound 1 (720 mg) were separated via Preparative Chiral SFC (Stationary phase: Chiralpak® IA 5 μm 250×20 mm, Mobile phase: 70% CO$_2$, 30% EtOH (+0.3% iPrNH$_2$)). The first eluted enantiomer (303 mg) was crystallized from Et$_2$O to give Enantiomer 1A (270 mg). The second eluted enantiomer (320 mg) was crystallized from Et$_2$O to give Enantiomer 1B (274 mg).

Compound 1:
$^1$H NMR (500 MHz, DMSO-d$_6$) δ ppm 3.15-3.30 (m, 2H) 3.73 (s, 3H) 3.74-3.85 (m, 2H) 4.06-4.17 (m, 3H) 4.45 (td, J=10.3, 6.1 Hz, 1H) 4.98 (t, J=5.4 Hz, 1H) 5.83 (d, J=8.5 Hz, 1H) 6.35 (s, 1H) 6.66 (t, J=1.9 Hz, 1H) 6.76-6.82 (m, 2H) 6.84 (s, 1H) 6.98 (dd, J=11.2, 2.4 Hz, 1H) 7.37-7.42 (m, 2H) 7.44-7.49 (m, 1H) 8.16 (s, 1H) 8.39 (s, 1H) 9.13 (s, 1H)
LC/MS (method LC-A): R$_t$ 3.06 min, MH$^+$ 572
Melting point: 151° C.

Enantiomer 1A:
$^1$H NMR (500 MHz, DMSO-d$_6$) δ ppm 3.15-3.29 (m, 2H) 3.73 (s, 3H) 3.74-3.86 (m, 2H) 4.06-4.19 (m, 3H) 4.45 (td, J=10.2, 6.3 Hz, 1H) 4.97 (t, J=5.5 Hz, 1H) 5.83 (d, J=8.8 Hz, 1H) 6.36 (s, 1H) 6.66 (t, J=1.9 Hz, 1H) 6.76-6.82 (m, 2H) 6.84 (s, 1H) 6.98 (dd, J=11.3, 2.5 Hz, 1H) 7.37-7.42 (m, 2H) 7.46 (d, J=7.9 Hz, 1H) 8.16 (s, 1H) 8.39 (s, 1H) 9.13 (s, 1H)
LC/MS (method LC-A): R$_t$ 3.06 min, MH$^+$ 572
[α]$_D^{20}$: −44.8° (c 0.2525, DMF)
Chiral SFC (method SFC-A): R$_t$ 2.59 min, MH$^+$ 572, chiral purity 100%.
Melting point: 163° C.

Enantiomer 1B:
$^1$H NMR (500 MHz, DMSO-d$_6$) δ ppm 3.15-3.30 (m, 2H) 3.73 (s, 3H) 3.74-3.85 (m, 2H) 4.06-4.19 (m, 3H) 4.45 (td, J=10.3, 6.1 Hz, 1H) 4.97 (t, J=5.5 Hz, 1H) 5.83 (d, J=8.5 Hz, 1H) 6.36 (s, 1H) 6.66 (t, J=1.9 Hz, 1H) 6.76-6.82 (m, 2H) 6.84 (s, 1H) 6.98 (dd, J=11.2, 2.4 Hz, 1H) 7.36-7.43 (m, 2H) 7.46 (d, J=7.9 Hz, 1H) 8.16 (s, 1H) 8.39 (s, 1H) 9.13 (s, 1H)
LC/MS (method LC-A): R$_t$ 3.06 min, MH$^+$ 572
[α]$_D^{20}$: +36.2° (c 0.2567, DMF)
Chiral SFC (method SFC-A): R$_t$ 3.15 min, MH$^+$ 572, chiral purity 98.07%.
Melting point: 162° C.

Example 2: Synthesis of 2-(4-fluoro-2-(2-hydroxyethoxy)phenyl)-2-((3-methoxy-5-(1H-1,2,4-triazol-1-yl)phenyl)amino)-1-(5-methoxy-6-(trifluoromethyl)indolin-1-yl)ethanone (Compound 2) and Chiral Separation into Enantiomers 2A and 2B

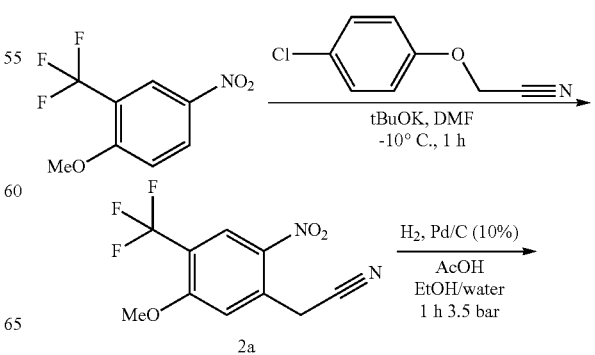

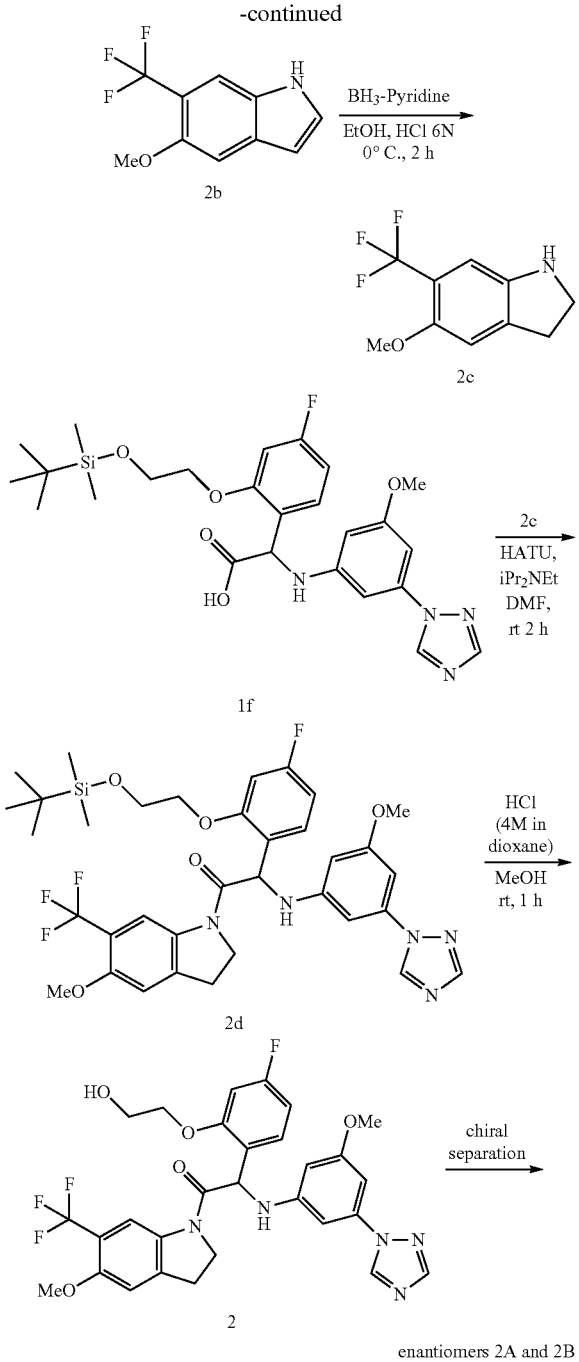

Synthesis of Intermediate 2b

A solution of 2-(5-methoxy-2-nitro-4-(trifluoromethyl)phenyl)acetonitrile 2a (26 g, 99.9 mmol) in ethanol/water (9/1) (500 mL) and AcOH (5.2 mL) was hydrogenated for 1 h at a pressure of 3.5 Bar with 10% Pd/C (15.3 g) as the catalyst. The reaction mixture was filtered through a pad of Celite® and the filter cake was washed with a solvent mixture of $CH_2Cl_2$ and $CH_3OH$. The filtrate was concentrated under reduced pressure. The residue was filtered through a glass filter charged with silica 60-200 μm using heptane/EtOAc 80/20 as the eluent. The fractions containing the expected compound were combined and the solvent was concentrated under reduced pressure to give 5-methoxy-6-(trifluoromethyl)-1H-indole 2b (15.6 g).

Synthesis of Intermediate 2c

At 0° C., $BH_3$-Pyridine (23.5 mL, 232.4 mmol) was added dropwise to a solution of 5-methoxy-6-(trifluoromethyl)-1H-indole 2b (10 g, 46.5 mmol) in EtOH (60 mL). 6N HCl (140 mL) was slowly added while maintaining the temperature below 10° C. The mixture was stirred at 0° C. for 2 h. Water (200 mL) was added and the mixture was basified to pH 8-9 with a concentrated aqueous solution of NaOH (the reaction temperature was kept below 20° C.). The precipitate was filtered off, washed with water (twice) and co-evaporated under reduced pressure with toluene to give 5-methoxy-6-(trifluoromethyl)indoline 2c (9 g).

Synthesis of Intermediate 2d

To a solution of 2-(2-(2-((tert-butyldimethylsilyl)oxy)ethoxy)-4-fluorophenyl)-2-((3-methoxy-5-(1H-1,2,4-triazol-1-yl)phenyl)amino)acetic acid 1f (1.02 g, 1.97 mmol) in DMF (10 mL) were added HATU (1.13 g, 2.96 mmol), diisopropylethylamine (979 μL, 5.92 mmol) and 5-methoxy-6-(trifluoromethyl)indoline 2c (429 mg, 1.97 mmol). The reaction mixture was stirred at room temperature for 2 h. The reaction mixture was diluted with water. The precipitate was filtered off, washed with water and taken up with EtOAc. The organic layer was washed with a 10% solution of $K_2CO_3$ in water, water, dried over $MgSO_4$, filtered and the solvent was concentrated under reduced pressure to give 2-(2-(2-((tert-butyldimethylsilyl)oxy)ethoxy)-4-fluorophenyl)-2-((3-methoxy-5-(1H-1,2,4-triazol-1-yl)phenyl)amino)-1-(5-methoxy-6-(trifluoromethyl)indolin-1-yl)ethanone 2d (1.36 g). The compound was used as such in the next reaction step.

Synthesis of Compound 2 and Chiral Separation into Enantiomers 2A and 2B

Under a $N_2$ flow, at 5° C., 4M HCl in dioxane (4.75 mL, 18.99 mmol) was added dropwise to a solution of 2-(2-(2-((tert-butyldimethylsilyl)oxy)ethoxy)-4-fluorophenyl)-2-((3-methoxy-5-(1H-1,2,4-triazol-1-yl)phenyl)amino)-1-(5-methoxy-6-(trifluoromethyl)indolin-1-yl)ethanone 2d (1.36 g, 1.9 mmol) in MeOH (25 mL). The reaction was stirred at room temperature for 1 h. The mixture was cooled to 0° C., basified with a 10% aqueous solution of $K_2CO_3$ and extracted with EtOAc. The organic phase was separated, dried over $MgSO_4$, filtered and the solvent was concentrated under reduced pressure. The residue was crystallized from MeOH to give 2-(4-fluoro-2-(2-hydroxyethoxy)phenyl)-2-

Synthesis of Intermediate 2a

A mixture of 1-methoxy-4-nitro-2-(trifluoromethyl)benzene [CAS 654-76-2] (24.5 g, 110.8 mmol) and 4-chlorophenoxyacetonitrile [CAS 3598-13-8] (20.4 g, 121.9 mmol) in DMF (100 mL) was added dropwise over 30 min to a stirred solution of tBuOK (27.35 g, 243.7 mmol) in DMF (100 mL) at −10° C. After addition, the purple solution was maintained at −10° C. for 1 h. 500 mL of ice-water and 500 mL of 6N HCl were added and the precipitate was filtered off, washed with water and dried under reduced pressure to afford 40.4 g of 2-(5-methoxy-2-nitro-4-(trifluoromethyl)phenyl)acetonitrile 2a (used as such in the next step).

((3-methoxy-5-(1H-1,2,4-triazol-1-yl)phenyl)amino)-1-(5-methoxy-6-(trifluoromethyl)indolin-1-yl)ethanone 2 (850 mg) as a racemate.

The enantiomers of Compound 2 (800 mg) were separated via Preparative Chiral SFC (Stationary phase: Chiralpak® IA 5 μm 250×20 mm, Mobile phase: 6% CH$_2$Cl$_2$, 70% CO$_2$, 24% EtOH (+0.3% iPrNH$_2$)). The first eluted enantiomer (370 mg) was solidified by trituration with diisopropyl ether to give Enantiomer 2A (329 mg). The second eluted enantiomer (400 mg) was further purified by flash chromatography on silica gel (15-40 μm, 24 g, CH$_2$Cl$_2$/MeOH 99/1). The pure fractions were combined and the solvent was concentrated under reduced pressure. The residue (320 mg) was solidified by trituration with diisopropyl ether to give Enantiomer 2B (262 mg).

Compound 2:

$^1$H NMR (500 MHz, DMSO-d$_6$) δ ppm 3.15-3.30 (m, 2H) 3.72 (s, 3H) 3.74-3.83 (m, 2H) 3.84 (s, 3H) 4.04-4.18 (m, 3H) 4.43 (td, J=10.4, 6.3 Hz, 1H) 4.99 (t, J=5.7 Hz, 1H) 5.81 (d, J=8.5 Hz, 1H) 6.35 (s, 1H) 6.65 (t, J=1.9 Hz, 1H) 6.75-6.81 (m, 2H) 6.83 (s, 1H) 6.98 (dd, J=11.2, 2.4 Hz, 1H) 7.24 (s, 1H) 7.39 (dd, J=8.5, 6.9 Hz, 1H) 8.16 (s, 1H) 8.35 (s, 1H) 9.13 (s, 1H)

LC/MS (method LC-A): R$_t$ 2.99 min, MH$^+$ 602

Melting point: 192° C.

Enantiomer 2A:

$^1$H NMR (400 MHz, DMSO-d$_6$) δ ppm 3.16-3.28 (m, 2H) 3.72 (s, 3H) 3.74-3.83 (m, 2H) 3.84 (s, 3H) 4.03-4.18 (m, 3H) 4.37-4.49 (m, 1H) 4.97 (t, J=5.6 Hz, 1H) 5.81 (d, J=8.1 Hz, 1H) 6.35 (s, 1H) 6.65 (s, 1H) 6.73-6.81 (m, 2H) 6.83 (s, 1H) 6.97 (dd, J=11.1, 2.0 Hz, 1H) 7.23 (s, 1H) 7.39 (t, J=7.6 Hz, 1H) 8.15 (s, 1H) 8.35 (s, 1H) 9.12 (s, 1H)

LC/MS (method LC-A): R$_t$ 2.97 min, MH$^+$ 602

$[α]_D^{20}$: −45.0° (c 0.2425, DMF)

Chiral SFC (method SFC-A): R$_t$ 4.14 min, MH$^+$ 602, chiral purity 100%.

Enantiomer 2B:

$^1$H NMR (400 MHz, DMSO-d$_6$) δ ppm 3.16-3.28 (m, 2H) 3.72 (s, 3H) 3.74-3.83 (m, 2H) 3.84 (s, 3H) 4.02-4.20 (m, 3H) 4.42 (td, J=10.2, 6.3 Hz, 1H) 4.97 (t, J=5.6 Hz, 1H) 5.81 (d, J=8.6 Hz, 1H) 6.35 (s, 1H) 6.65 (s, 1H) 6.73-6.81 (m, 2H) 6.83 (s, 1H) 6.97 (dd, J=11.4, 2.3 Hz, 1H) 7.23 (s, 1H) 7.36-7.43 (m, 1H) 8.15 (s, 1H) 8.35 (s, 1H) 9.12 (s, 1H)

LC/MS (method LC-A): R$_t$ 2.97 min, MH$^+$ 602

$[α]_D^{20}$: +43.4° (c 0.2007, DMF)

Chiral SFC (method SFC-A): R$_t$ 5.08 min, MH$^+$ 602, chiral purity 100%.

Example 3: Synthesis of 2-(4-fluoro-2-(2-hydroxyethoxy)phenyl)-2-((3-methoxy-5-(1H-1,2,4-triazol-1-yl)phenyl)amino)-1-(6-(trifluoromethoxy)indolin-1-yl)ethanone (Compound 3) and Chiral Separation into Enantiomers 3A and 3B

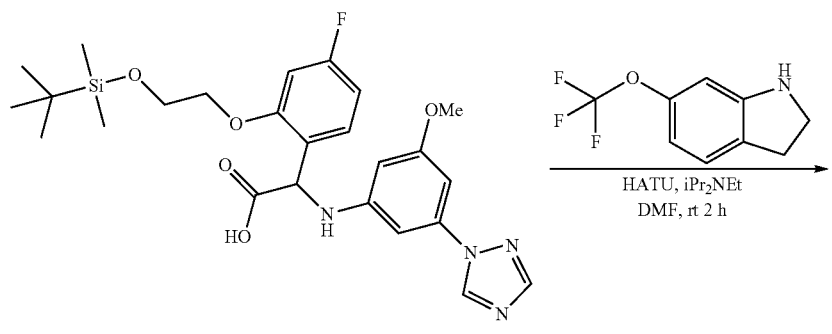

1f

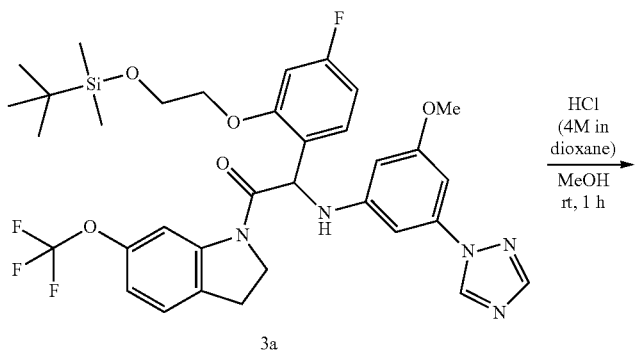

3a

-continued

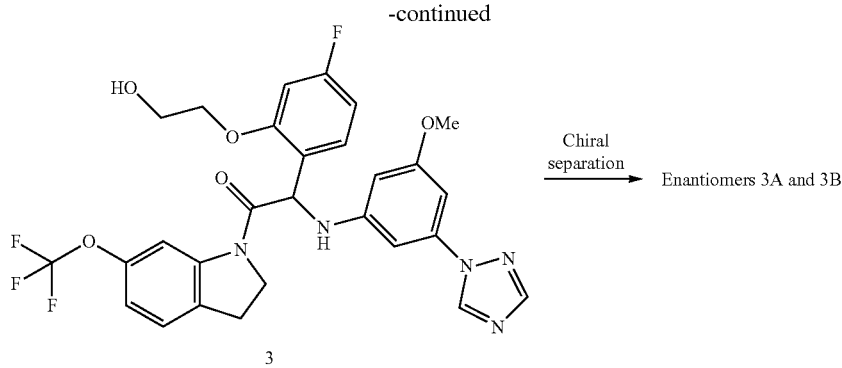

Chiral separation → Enantiomers 3A and 3B

Synthesis of Intermediate 3a

To a solution of 2-(2-(2-((tert-butyldimethylsilyl)oxy)ethoxy)-4-fluorophenyl)-2-((3-methoxy-5-(1H-1,2,4-triazol-1-yl)phenyl)amino)acetic acid 1f (1.02 g, 1.974 mmol) in DMF (10 mL) were added HATU (1.13 g, 2.96 mmol), diisopropylethylamine (979 µL, 5.92 mmol) and 6-(trifluoromethoxy)indoline [CAS 959235-95-1] (401 mg, 1.97 mmol). The reaction mixture was stirred at room temperature for 2 h. The reaction mixture was diluted with water. The precipitate was filtered off, washed with water and taken up with EtOAc. The organic layer was washed with a 10% solution of $K_2CO_3$ in water, water, dried over $MgSO_4$, filtered and the solvent was concentrated under reduced pressure to give 2-(2-(2-((tert-butyldimethylsilyl)-oxy)ethoxy)-4-fluorophenyl)-2-((3-methoxy-5-(1H-1,2,4-triazol-1-yl)phenyl)amino)-1-(6-(trifluoromethoxy)indolin-1-yl)ethanone 3a (1.34 g). The crude compound was used directly in the next reaction step.

Synthesis of Compound 3 and Chiral Separation into Enantiomers 3A and 3B

Under a $N_2$ flow, at 5° C., 4M HCl in dioxane (4.27 mL, 17.1 mmol) was added dropwise to a solution of 2-(2-(2-((tert-butyldimethylsilyl)oxy)ethoxy)-4-fluorophenyl)-2-((3-methoxy-5-(1H-1,2,4-triazol-1-yl)phenyl)amino)-1-(6-(trifluoromethoxy)indolin-1-yl)ethanone 3a (1.2 g, 1.71 mmol) in MeOH (25 mL). The reaction was stirred at room temperature for 1 h. The mixture was cooled to 0° C., basified with a 10% aqueous solution of $K_2CO_3$ and extracted with EtOAc. The organic phase was separated, dried over $MgSO_4$, filtered and the solvent was concentrated under reduced pressure. The residue was purified by flash chromatography on silica gel (15-40 µm, 40 g, $CH_2Cl_2$/MeOH gradient 99.5/0.5 to 99/1). The pure fractions were combined and concentrated to dryness under reduced pressure to give 2-(4-fluoro-2-(2-hydroxyethoxy)phenyl)-2-((3-methoxy-5-(1H-1,2,4-triazol-1-yl)phenyl)amino)-1-(6-(trifluoromethoxy)indolin-1-yl)ethanone 3 (550 mg) as a racemate. Part of this fraction was crystallized from MeOH to provide Compound 3 (36 mg).

The remaining material was used to separate the enantiomers of Compound 3 via Preparative Chiral SFC (Stationary phase: Chiralpak® AD-H 5 µm 250×20 mm, Mobile phase: 65% $CO_2$, 35% EtOH (+0.3% $iPrNH_2$)). The first eluted enantiomer (210 mg) was solidified by trituration with diisopropyl ether/heptane to give Enantiomer 3A (182 mg). The second eluted enantiomer (230 mg) was further purified by flash chromatography on silica gel (15-40 µm, 24 g, $CH_2Cl_2$/MeOH 99/1). The pure fractions were combined and the solvent was concentrated under reduced pressure. The residue (180 mg) was solidified by trituration with diisopropyl ether/heptane to give Enantiomer 3B (137 mg).

Compound 3:
$^1$H NMR (500 MHz, DMSO-$d_6$) δ ppm 3.06-3.25 (m, 2H) 3.73 (s, 3H) 3.75-3.86 (m, 2H) 4.06-4.17 (m, 3H) 4.38-4.50 (m, 1H) 4.95 (br s, 1H) 5.81 (d, J=8.6 Hz, 1H) 6.35 (s, 1H) 6.65 (s, 1H) 6.75-6.81 (m, 2H) 6.83 (s, 1H) 6.94-7.04 (m, 2H) 7.33 (d, J=8.6 Hz, 1H) 7.36-7.43 (m, 1H) 8.04 (s, 1H) 8.15 (s, 1H) 9.11 (s, 1H)

LC/MS (method LC-A): $R_t$ 3.13 min, MH$^+$ 588

Melting point: 178° C.

Enantiomer 3A:
$^1$H NMR (400 MHz, DMSO-$d_6$) δ ppm 3.06-3.26 (m, 2H) 3.72 (s, 3H) 3.74-3.86 (m, 2H) 4.05-4.18 (m, 3H) 4.38-4.50 (m, 1H) 4.97 (t, J=5.3 Hz, 1H) 5.82 (d, J=8.6 Hz, 1H) 6.35 (s, 1H) 6.65 (s, 1H) 6.74-6.86 (m, 3H) 6.94-7.04 (m, 2H) 7.34 (d, J=8.1 Hz, 1H) 7.36-7.42 (m, 1H) 8.04 (s, 1H) 8.15 (s, 1H) 9.12 (s, 1H)

LC/MS (method LC-A): $R_t$ 3.11 min, MH$^+$ 588

$[α]_D^{20}$: −38.2° (c 0.28, DMF)

Chiral SFC (method SFC-B): $R_t$ 3.38 min, MH$^+$ 588, chiral purity 100%.

Enantiomer 3B:
$^1$H NMR (400 MHz, DMSO-$d_6$) δ ppm 3.07-3.26 (m, 2H) 3.72 (s, 3H) 3.74-3.86 (m, 2H) 4.04-4.20 (m, 3H) 4.38-4.50 (m, 1H) 4.97 (t, J=5.6 Hz, 1H) 5.81 (d, J=8.6 Hz, 1H) 6.35 (s, 1H) 6.65 (s, 1H) 6.74-6.87 (m, 3H) 6.94-7.03 (m, 2H) 7.34 (d, J=8.1 Hz, 1H) 7.36-7.42 (m, 1H) 8.04 (s, 1H) 8.15 (s, 1H) 9.12 (s, 1H)

LC/MS (method LC-A): $R_t$ 3.11 min, MH$^+$ 588

$[α]_D^{20}$: +40.9° (c 0.23, DMF)

Chiral SFC (method SFC-B): $R_t$ 5.31 min, MH$^+$ 588, chiral purity 100%.

Example 4: Synthesis of 2-(4-chloro-2-(2-hydroxyethoxy)phenyl)-2-((3-methoxy-5-(1H-1,2,4-triazol-1-yl)phenyl)amino)-1-(6-(trifluoromethyl)indolin-1-yl)ethanone (Compound 4) and Chiral Separation into Enantiomers 4A and 4B

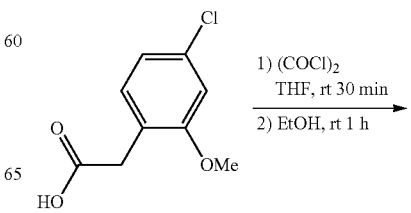

1) $(COCl)_2$
THF, rt 30 min
2) EtOH, rt 1 h

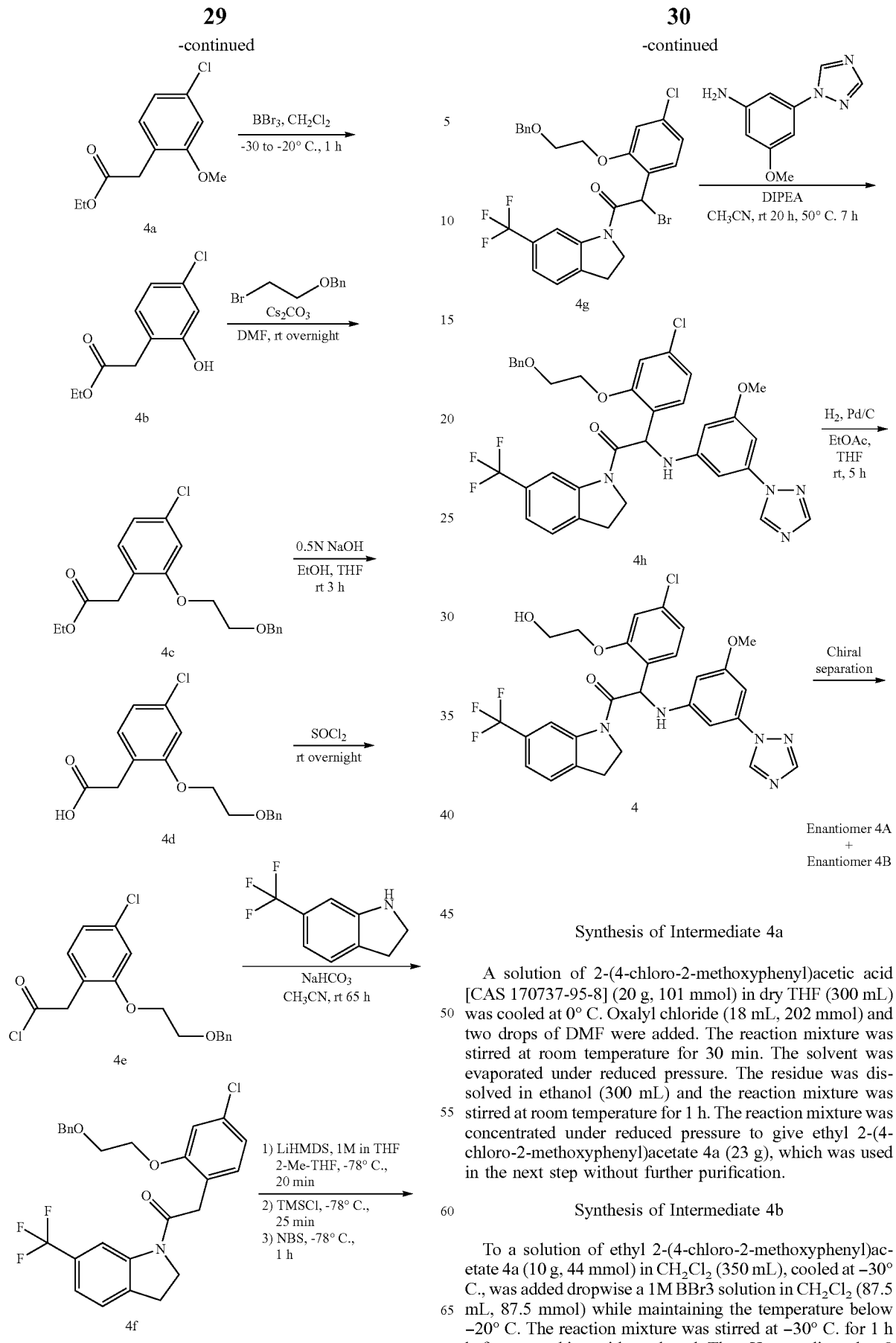

Synthesis of Intermediate 4a

A solution of 2-(4-chloro-2-methoxyphenyl)acetic acid [CAS 170737-95-8] (20 g, 101 mmol) in dry THF (300 mL) was cooled at 0° C. Oxalyl chloride (18 mL, 202 mmol) and two drops of DMF were added. The reaction mixture was stirred at room temperature for 30 min. The solvent was evaporated under reduced pressure. The residue was dissolved in ethanol (300 mL) and the reaction mixture was stirred at room temperature for 1 h. The reaction mixture was concentrated under reduced pressure to give ethyl 2-(4-chloro-2-methoxyphenyl)acetate 4a (23 g), which was used in the next step without further purification.

Synthesis of Intermediate 4b

To a solution of ethyl 2-(4-chloro-2-methoxyphenyl)acetate 4a (10 g, 44 mmol) in $CH_2Cl_2$ (350 mL), cooled at −30° C., was added dropwise a 1M BBr3 solution in $CH_2Cl_2$ (87.5 mL, 87.5 mmol) while maintaining the temperature below −20° C. The reaction mixture was stirred at −30° C. for 1 h before quenching with methanol. The pH was adjusted to 8 by addition of an aqueous saturated solution of NaHCO$_3$. The phases were separated. The aqueous phase was extracted with CH$_2$Cl$_2$. The organic phases were combined, dried over MgSO$_4$, filtered and concentrated under reduced pressure to afford ethyl 2-(4-chloro-2-hydroxyphenyl)acetate 4b (9.5 g), which was used in the next step without further purification.

Synthesis of Intermediate 4c

To a mixture of ethyl 2-(4-chloro-2-hydroxyphenyl)acetate 4b [CAS 1261826-30-5] (2.82 g, 13.1 mmol) and cesium carbonate (8.56 g, 26.3 mmol) in DMF (50 mL) was added benzyl 2-bromoethyl ether [CAS 1462-37-9] (2.29 g, 14.5 mmol). The reaction mixture was stirred at room temperature for 24 h. H$_2$O was added and the reaction mixture was extracted with EtOAc. The organic phase was dried over Na$_2$SO$_4$, filtered and concentrated under reduced pressure. The residue was purified by flash chromatography on silica gel using a gradient of EtOAc (2% to 20%) in heptane to give ethyl 2-(2-(2-(benzyloxy)ethoxy)-4-chlorophenyl)acetate 4c (4.17 g).

Synthesis of Intermediate 4d

To a solution of ethyl 2-(2-(2-(benzyloxy)ethoxy)-4-chlorophenyl)acetate 4c (4.17 g, 12.0 mmol) in a mixture of EtOH (80 mL) and THF (40 mL) was added 0.5N NaOH (72 mL, 36.0 mmol). The reaction mixture was stirred at room temperature for 3 h. The reaction mixture was partially concentrated under reduced pressure to remove the organic solvents. The residue was acidified to pH 2-3 with 1N HCl and the mixture was extracted with EtOAc. The organic phase was dried over MgSO$_4$, filtered and concentrated under reduced pressure to give 2-(2-(2-(benzyloxy)ethoxy)-4-chlorophenyl)acetic acid 4d (3.83 g).

Synthesis of Intermediate 4e

A solution of 2-(2-(2-(benzyloxy)ethoxy)-4-chlorophenyl)acetic acid 4d (7.12 g, 22.2 mmol) in thionyl chloride (50 mL, 689 mmol) was stirred at room temperature for 18 h. The reaction mixture was concentrated under reduced pressure and co-evaporated with toluene to give 2-(2-(2-(benzyloxy)ethoxy)-4-chlorophenyl)acetyl chloride 4e (7.53 g) which was used in the next step without further purification.

Synthesis of Intermediate 4f

A solution of 2-(2-(2-(benzyloxy)ethoxy)-4-chlorophenyl)acetyl chloride 4e (5.29 g, 15.6 mmol) in CH$_3$CN (50 mL) was added dropwise under N$_2$-atm to a stirring mixture of 6-(trifluoromethyl)indoline [CAS 181513-29-1] (2.92 g, 15.6 mmol) and sodium bicarbonate (1.44 g, 17.1 mmol) in CH$_3$CN (50 mL). The reaction mixture was stirred at room temperature for 65 h and poured out into water (500 mL). The product was extracted (2×) with Et$_2$O. The combined organic layers were washed with brine, dried over MgSO$_4$, filtered and evaporated under reduced pressure. The residue solidified upon standing. The product was stirred up in diisopropyl ether (25 mL), filtered off, washed (3×) with diisopropyl ether, and dried under vacuum at 45° C. to provide 2-(2-(2-(benzyloxy)ethoxy)-4-chlorophenyl)-1-(6-(trifluoromethyl)indolin-1-yl)ethanone 4f (6.97 g).

Synthesis of Intermediate 4g

A solution of 2-(2-(2-(benzyloxy)ethoxy)-4-chlorophenyl)-1-(6-(trifluoromethyl)indolin-1-yl)ethanone 4f (1.5 g, 3.06 mmol) in 2-Me-THF (125 mL) was stirred under N$_2$-flow and cooled to −78° C. A solution of 1M lithium bis(trimethylsilyl)amide in THF (6.12 mL, 6.12 mmol) was added dropwise and the resulting mixture was stirred at −78° C. for 20 minutes. Chlorotrimethylsilane (626 µL, 4.90 mmol) was added dropwise and the mixture was stirred at −78° C. for 25 min. A solution of N-bromosuccinimide (599 mg, 3.37 mmol) in 2-Me-THF (50 mL) was added dropwise and the reaction mixture was stirred at −78° C. for 1 h. An aqueous saturated solution of NH$_4$Cl (60 mL) was added at once, and the resulting mixture was stirred without cooling until the temperature reached 0° C. Water (20 mL) was added and, after stirring for 30 min, the layers were separated. The organic layer was dried over MgSO$_4$, filtered, evaporated under reduced pressure, and co-evaporated with CH$_3$CN to provide 2-(2-(2-(benzyloxy)ethoxy)-4-chlorophenyl)-2-bromo-1-(6-(trifluoromethyl)indolin-1-yl)ethanone 4g (1.16 g). The product was used without further purification in the next step.

Synthesis of Intermediate 4h

To a stirred solution of 2-(2-(2-(benzyloxy)ethoxy)-4-chlorophenyl)-2-bromo-1-(6-(trifluoromethyl)indolin-1-yl) ethanone 4g (1.74 g, 3.06 mmol) in CH$_3$CN (100 mL) under N$_2$-atm were added 3-methoxy-5-(1H-1,2,4-triazol-1-yl)aniline [CAS 1220630-56-7] (874 mg, 4.59 mmol), and diisopropylethylamine (1.06 mL, 6.12 mmol) and the reaction mixture was stirred at room temperature for 20 h and then at 50° C. for 7 h. The mixture was cooled to room temperature and poured out into stirring H$_2$O (400 mL). The product was extracted (2×) with Et$_2$O. The combined organic layers were dried over MgSO$_4$, filtered, and evaporated under reduced pressure. The residue was purified by flash chromatography on silica gel (40 g) using a gradient of heptane/EtOAc/EtOH 100/0/0 to 40/45/15. The desired fractions were combined and the solvent was evaporated under reduced pressure and co-evaporated with toluene. The residue was dried under vacuum at 50° C. to provide 2-(2-(2-(benzyloxy)ethoxy)-4-chlorophenyl)-2-((3-methoxy-5-(1H-1,2,4-triazol-1-yl)phenyl)amino)-1-(6-(trifluoromethyl)indolin-1-yl)ethanone 4h (1.43 g).

Synthesis of Compound 4 and Chiral Separation into Enantiomers 4A and 4B

A solution of 2-(2-(2-(benzyloxy)ethoxy)-4-chlorophenyl)-2-((3-methoxy-5-(1H-1,2,4-triazol-1-yl)phenyl) amino)-1-(6-(trifluoromethyl)indolin-1-yl)ethanone 4h (1.43 g, 2.11 mmol) in a solvent mixture of THF (15 mL) in EtOAc (75 mL) was hydrogenated for 5 h at room temperature under atmospheric pressure of H$_2$ using Pd/C (0.5 g) as the catalyst. The catalyst was removed by filtration over Dicalite®. The filter cake was washed several times with THF, and the combined filtrates were evaporated under reduced pressure. The solid residue was stirred up in a solvent mixture CH$_2$Cl$_2$/EtOAc/MeOH 1/2/1. The precipitate was filtered off, washed (2×) with EtOAc, and dried under vacuum at 45° C. to provide racemic 2-(4-chloro-2-(2-hydroxyethoxy)phenyl)-2-((3-methoxy-5-(1H-1,2,4-triazol-1-yl)phenyl)amino)-1-(6-(trifluoromethyl)indolin-1-yl)ethanone (Compound 4, 600 mg).

The enantiomers of Compound 4 (700 mg) were separated via Preparative Chiral SFC (Stationary phase: Chiralpak® Diacel AD 20×250 mm, Mobile phase: CO$_2$, MeOH/iPrOH (50/50)+0.4% iPrNH$_2$). The product fractions were combined and evaporated under reduced pressure to provide Enantiomer 4A as the first eluted product and Enantiomer 4B as the second eluted product. Both enantiomers were further purified by flash chromatography on silica gel (4 g) using a gradient heptane/EtOAc/EtOH 100/0/0 to 40/45/15. The desired fractions were combined and evaporated under reduced pressure. The residue was stirred in water (3 mL) and MeOH (0.75 mL). The solids were filtered off, washed (3×) with water, and dried under vacuum at 50° C. to provide Enantiomer 4A (81 mg) and Enantiomer 4B (132 mg).

Enantiomer 4A:

$^1$H NMR (400 MHz, DMSO-$d_6$) δ ppm 3.18-3.28 (m, 2H) 3.73 (s, 3H) 3.74-3.84 (m, 2H) 4.08-4.19 (m, 3H) 4.44 (td, J=10.2, 6.7 Hz, 1H) 4.96 (t, J=5.6 Hz, 1H) 5.84 (d, J=8.6 Hz, 1H) 6.35 (t, J=2.1 Hz, 1H) 6.66 (t, J=1.7 Hz, 1H) 6.79-6.87 (m, 2H) 7.02 (dd, J=8.3, 1.9 Hz, 1H) 7.15 (d, J=1.8 Hz, 1H) 7.34-7.43 (m, 2H) 7.43-7.51 (m, 1H) 8.15 (s, 1H) 8.38 (br s, 1H) 9.12 (s, 1H)

LC/MS (method LC-C): $R_t$ 1.16 min, MH$^+$ 588

$[α]_D^{20}$: −42.9° (c 0.515, DMF)

Chiral SFC (method SFC-K): $R_t$ 2.91 min, MH$^+$ 588, chiral purity 100%.

Enantiomer 4B:

$^1$H NMR (400 MHz, DMSO-$d_6$) δ ppm 3.15-3.28 (m, 2H) 3.73 (s, 3H) 3.74-3.84 (m, 2H) 4.07-4.22 (m, 3H) 4.44 (td, J=10.1, 6.6 Hz, 1H) 4.96 (t, J=5.5 Hz, 1H) 5.84 (d, J=8.6 Hz, 1H) 6.35 (t, J=2.0 Hz, 1H) 6.67 (t, J=1.9 Hz, 1H) 6.79-6.87 (m, 2H) 7.03 (dd, J=8.1, 2.0 Hz, 1H) 7.15 (d, J=2.0 Hz, 1H) 7.34-7.42 (m, 2H) 7.43-7.49 (m, 1H) 8.16 (s, 1H) 8.38 (br s, 1H) 9.13 (s, 1H)

LC/MS (method LC-C): $R_t$ 1.15 min, MH$^+$ 588

$[α]_D^{20}$: −39.5° (c 0.595, DMF)

Chiral SFC (method SFC-K): $R_t$ 2.78 min, MH$^+$ 588, chiral purity 100%.

Example 5: Synthesis of 2-(4-chloro-2-(2-hydroxyethoxy)phenyl)-2-((3-methoxy-5-(1H-1,2,4-triazol-1-yl)phenyl)amino)-1-(5-methoxy-6-(trifluoromethyl)indolin-1-yl)ethanone (Compound 5) and Chiral Separation into Enantiomers 5A and 5B

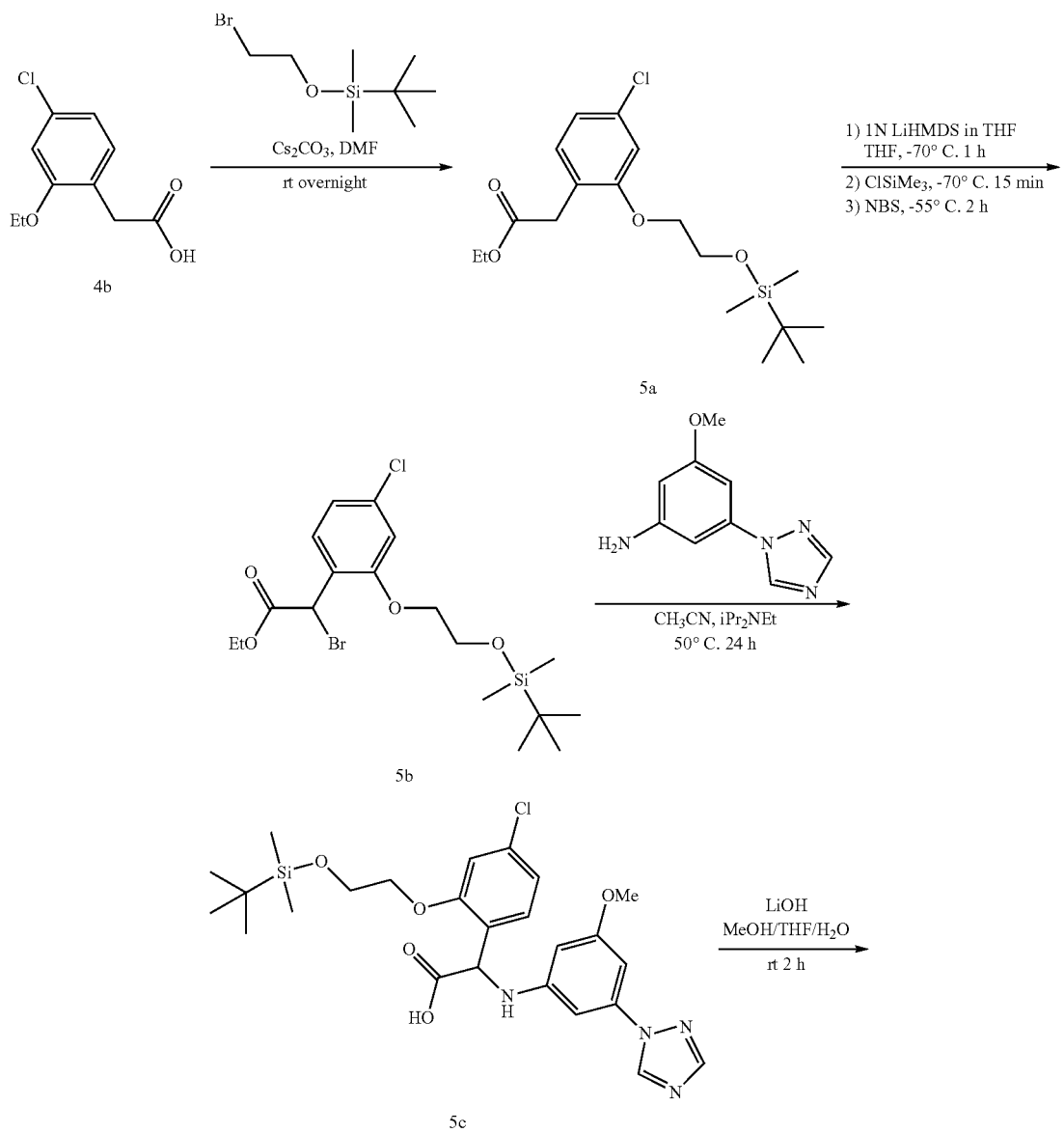

-continued

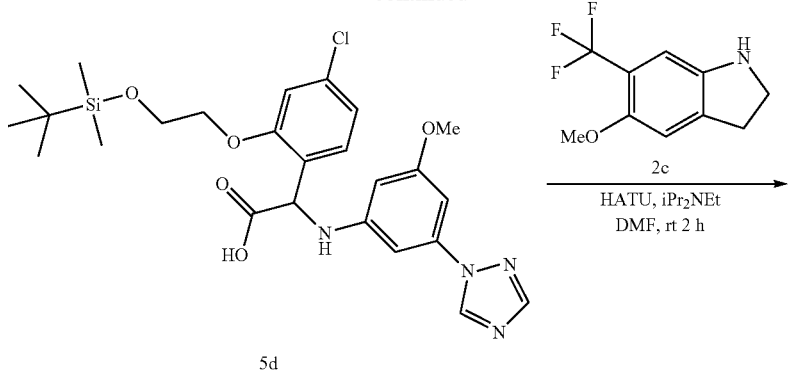

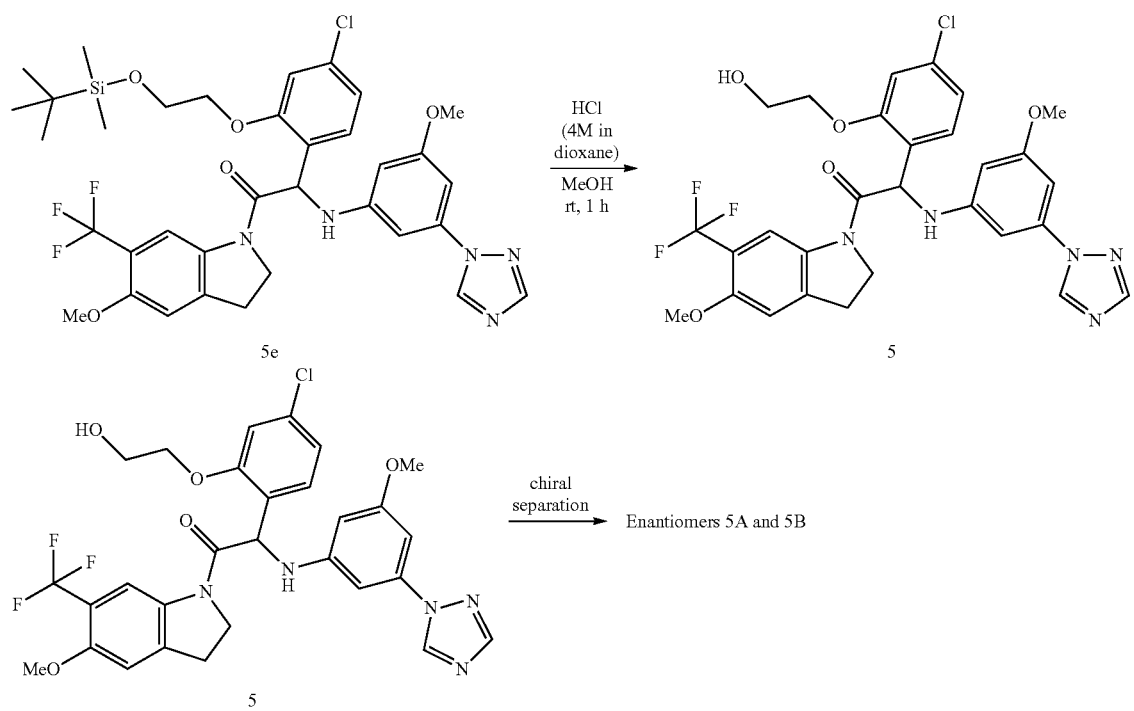

Synthesis of Intermediate 5a

To a mixture of ethyl 2-(4-chloro-2-hydroxyphenyl)acetate 4b (5.2 g, 24.2 mmol) and cesium carbonate (15.8 g, 48.5 mmol) in DMF (90 mL) at 10° C. was added (2-bromoethoxy)(tert-butyl)dimethylsilane [CAS 86864-60-0] (6.26 mL, 29.1 mmol). The reaction mixture was stirred at room temperature overnight. H$_2$O was added and the reaction mixture was extracted with EtOAc. The organic phase was dried over MgSO$_4$, filtered and concentrated under reduced pressure. The residue was purified by flash chromatography on silica gel (15-40 μm, 80 g, heptane/EtOAc 80/20). The pure fractions were combined and the solvent was removed under reduced pressure to give ethyl 2-(2-(2-((tert-butyldimethylsilyl)oxy)ethoxy)-4-chlorophenyl)acetate 5a (7.8 g).

Synthesis of Intermediate 5b

To a 1M lithium bis(trimethylsilyl)amide solution in THF (41.8 mL, 41.8 mmol), cooled to −70° C. was added a solution of ethyl 2-(2-(2-((tert-butyldimethylsilyl)oxy)ethoxy)-4-chlorophenyl)acetate 5a (7.8 g, 20.9 mmol) in THF (45 mL). After 1 h at −70° C., chlorotrimethylsilane (4.24 mL, 33.5 mmol) was added. The reaction mixture was stirred at −70° C. for 15 min. N-Bromosuccinimide (4.46 g, 25.1 mmol) in THF (45 mL) was added and stirring was continued at −55° C. for 2 h. The reaction mixture was poured out into H$_2$O and extracted twice with EtOAc. The organic phases were combined, dried over MgSO$_4$, filtered and concentrated under reduced pressure to give ethyl 2-bromo-2-(2-(2-((tert-butyldimethylsilyl)oxy)ethoxy)-4-chlorophenyl)acetate 5b (10.1 g) which was used in the next step without further purification.

Synthesis of Intermediate 5c

A mixture of ethyl 2-bromo-2-(2-(2-((tert-butyldimethylsilyl)oxy)ethoxy)-4-chlorophenyl)acetate 5b (4.75 g, 10.5 mmol), 3-methoxy-5-(1H-1,2,4-triazol-1-yl)aniline [CAS 1220630-56-7] (3 g, 15.8 mmol) and diisopropylethylamine (3.62 mL, 21.0 mmol) in CH$_3$CN (90 mL) was stirred at 50° C. for 24 h. The reaction mixture was concentrated under reduced pressure. The residue was taken up with EtOAc and washed with 0.5N HCl, water and brine. The organic phase was dried over MgSO$_4$, filtered and concentrated under reduced pressure. The residue was purified by flash chromatography on silica gel (15-40 µm, 120 g, heptane/EtOAc gradient 80/20 to 70/30) to give ethyl 2-(2-(2-((tert-butyldimethylsilyl)oxy)ethoxy)-4-chlorophenyl)-2-((3-methoxy-5-(1H-1,2,4-triazol-1-yl)phenyl)amino)acetate 5c (3.7 g).

Synthesis of Intermediate 5d

Lithium hydroxide monohydrate (523 mg, 12.5 mmol) in water (25 mL) was added portionwise to a solution of ethyl 2-(2-(2-((tert-butyldimethylsilyl)oxy)ethoxy)-4-chlorophenyl)-2-((3-methoxy-5-(1H-1,2,4-triazol-1-yl)phenyl)amino)acetate 5c (3.5 g, 6.24 mmol) in THF/CH$_3$OH (1/1) (50 mL) at 10° C. The reaction was stirred at room temperature for 2 h, diluted with water and cooled down to 0° C. The solution was slowly acidified with 0.5N HCl to pH 6 and extracted with EtOAc. The organic layer was dried over MgSO$_4$, filtered and the solvent was concentrated under reduced pressure to give 2-(2-(2-((tert-butyldimethylsilyl)oxy)ethoxy)-4-chlorophenyl)-2-((3-methoxy-5-(1H-1,2,4-triazol-1-yl)phenyl)amino)acetic acid 5d (3.1 g). The compound was used as such in the next step.

Synthesis of Intermediate 5e

A mixture of 5-methoxy-6-(trifluoromethyl)indoline 2c (400 mg, 1.84 mmol), 2-(2-(2-((tert-butyldimethylsilyl)oxy)ethoxy)-4-chlorophenyl)-2-((3-methoxy-5-(1H-1,2,4-triazol-1-yl)phenyl)amino)acetic acid 5d (982 mg, 1.84 mmol), HATU (1.05 g, 2.76 mmol) and diisopropylethylamine (913 µL, 5.53 mmol) in DMF (10 mL) was stirred at room temperature for 2 h. The mixture was diluted with water. The precipitate was filtered off and washed with water. The precipitate was taken up with EtOAc, washed with a solution of K$_2$CO$_3$ 10% in water, water, dried over MgSO$_4$, filtered and the solvent was concentrated under reduced pressure to give 2-(2-(2-((tert-butyldimethylsilyl)oxy)ethoxy)-4-chlorophenyl)-2-((3-methoxy-5-(1H-1,2,4-triazol-1-yl)phenyl)amino)-1-(5-methoxy-6-(trifluoromethyl)indolin-1-yl)ethanone 5e (1.35 g). The compound was used as such in the next reaction step.

Synthesis of Compound 5 and Chiral Separation into Enantiomers 5A and 5B

Under a N$_2$ flow, at 5° C., 4M HCl in dioxane (4.6 mL, 18.4 mmol) was added dropwise to a solution of 2-(2-(2-((tert-butyldimethylsilyl)oxy)ethoxy)-4-chlorophenyl)-2-((3-methoxy-5-(1H-1,2,4-triazol-1-yl)phenyl)amino)-1-(5-methoxy-6-(trifluoromethyl)indolin-1-yl)ethanone 5e (1.35 g, 1.84 mmol) in MeOH (25 mL). The reaction was stirred at room temperature for 1 h. The mixture was cooled to 0° C., basified with a 10% aqueous solution of K$_2$CO$_3$ and extracted with EtOAc. The organic phase was separated, dried over MgSO$_4$, filtered and the solvent was concentrated under reduced pressure. The residue was purified by flash chromatography on silica gel (15-40 µm, 40 g, CH$_2$Cl$_2$/MeOH 98.5/1.5). The pure fractions were combined and concentrated to dryness under reduced pressure. The residue (980 mg) was crystallized from MeOH to afford 2-(4-chloro-2-(2-hydroxyethoxy)phenyl)-2-((3-methoxy-5-(1H-1,2,4-triazol-1-yl)phenyl)amino)-1-(5-methoxy-6-(trifluoromethyl)indolin-1-yl)ethanone 5 (805 mg) as a racemate.

The enantiomers of Compound 5 (771 mg) were separated via Preparative Chiral SFC (Stationary phase: Chiralpak® IA 5 µm 250×20 mm, Mobile phase: 6% CH$_2$Cl$_2$, 70% CO$_2$, 24% EtOH (+0.3% iPrNH$_2$)). The first eluted enantiomer (375 mg) was solidified by trituration with diisopropyl ether to give Enantiomer 5A (308 mg). The second eluted enantiomer (400 mg) was further purified by flash chromatography on silica gel (15-40 µm, 24 g, CH$_2$Cl$_2$/MeOH 99/1). The pure fractions were combined and the solvent was concentrated under reduced pressure. The residue (340 mg) was solidified by trituration with diisopropyl ether to give Enantiomer 5B (291 mg).

Compound 5:

$^1$H NMR (500 MHz, DMSO-d$_6$) δ ppm 3.15-3.30 (m, 2H) 3.72 (s, 3H) 3.74-3.83 (m, 2H) 3.85 (s, 3H) 4.06-4.20 (m, 3H) 4.41 (td, J=10.2, 6.3 Hz, 1H) 4.99 (t, J=5.5 Hz, 1H) 5.82 (d, J=8.5 Hz, 1H) 6.35 (s, 1H) 6.65 (t, J=1.9 Hz, 1H) 6.80-6.85 (m, 2H) 7.02 (dd, J=8.2, 1.9 Hz, 1H) 7.15 (d, J=2.2 Hz, 1H) 7.24 (s, 1H) 7.37 (d, J=8.5 Hz, 1H) 8.16 (s, 1H) 8.34 (s, 1H) 9.13 (s, 1H)

LC/MS (method LC-A): R$_t$ 3.13 min, MH$^+$ 618

Melting point: 228° C.

Enantiomer 5A:

$^1$H NMR (400 MHz, DMSO-d$_6$) δ ppm 3.16-3.28 (m, 2H) 3.72 (s, 3H) 3.74-3.83 (m, 2H) 3.84 (s, 3H) 4.06-4.21 (m, 3H) 4.35-4.46 (m, 1H) 4.97 (t, J=5.6 Hz, 1H) 5.81 (d, J=8.6 Hz, 1H) 6.35 (s, 1H) 6.65 (s, 1H) 6.77-6.86 (m, 2H) 7.02 (dd, J=8.3, 1.8 Hz, 1H) 7.14 (d, J=1.5 Hz, 1H) 7.24 (s, 1H) 7.38 (d, J=8.6 Hz, 1H) 8.15 (s, 1H) 8.34 (s, 1H) 9.12 (s, 1H)

LC/MS (method LC-A): R$_t$ 3.11 min, MH$^+$ 618

$[α]_D^{20}$: −40.3° (c 0.2383, DMF)

Chiral SFC (method SFC-C): R$_t$ 2.75 min, MH$^+$ 618, chiral purity 100%.

Enantiomer 5B:

$^1$H NMR (400 MHz, DMSO-d$_6$) δ ppm 3.16-3.28 (m, 2H) 3.72 (s, 3H) 3.74-3.83 (m, 2H) 3.84 (s, 3H) 4.06-4.20 (m, 3H) 4.36-4.46 (m, 1H) 4.97 (t, J=5.6 Hz, 1H) 5.81 (d, J=8.6 Hz, 1H) 6.35 (s, 1H) 6.65 (s, 1H) 6.78-6.85 (m, 2H) 7.01 (dd, J=8.3, 1.8 Hz, 1H) 7.14 (d, J=1.5 Hz, 1H) 7.24 (s, 1H) 7.38 (d, J=8.1 Hz, 1H) 8.15 (s, 1H) 8.34 (s, 1H) 9.12 (s, 1H)

LC/MS (method LC-A): R$_t$ 3.11 min, MH$^+$ 618

$[α]_D^{20}$: +40.0° (c 0.22, DMF)

Chiral SFC (method SFC-C): R$_t$ 3.60 min, MH$^+$ 618, chiral purity 98.47%.

Example 6 (Method 1): Synthesis of 2-(4-chloro-2-(2-hydroxyethoxy)phenyl)-2-((3-methoxy-5-(1H-1,2,4-triazol-1-yl)phenyl)amino)-1-(6-(trifluoromethoxy)indolin-1-yl)ethanone (Compound 6) and Chiral Separation into Enantiomers 6A and 6B

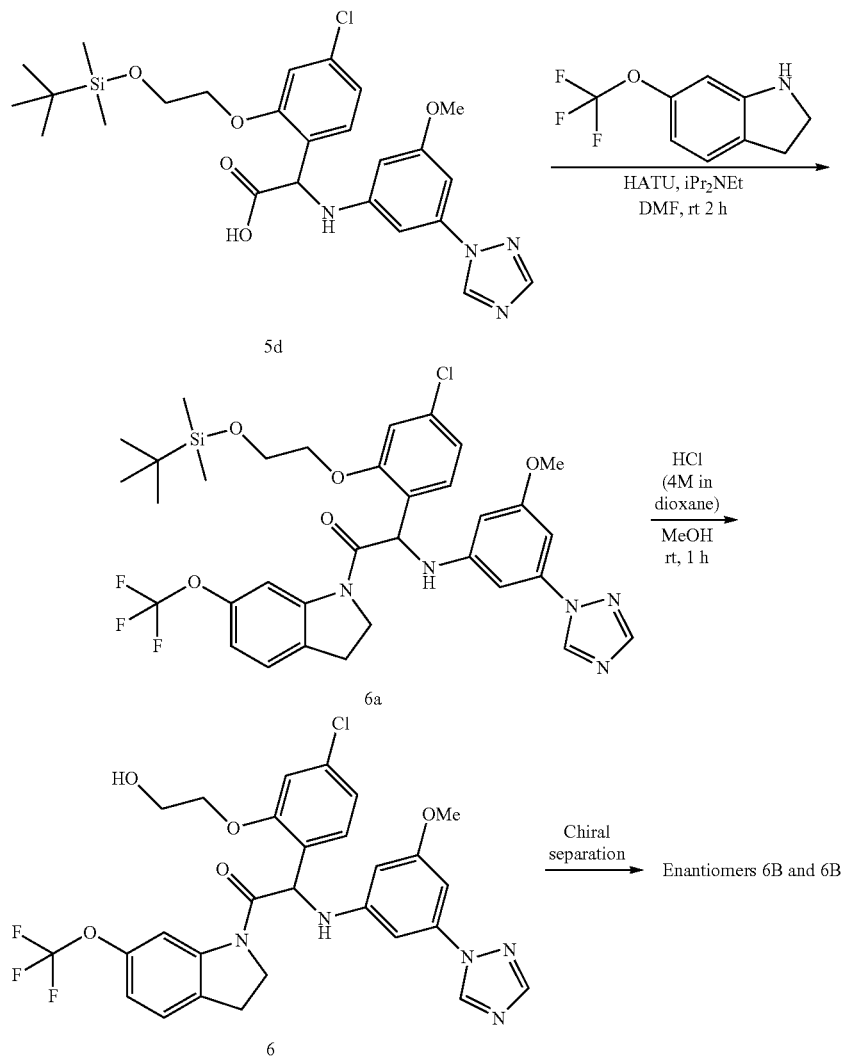

Synthesis of Intermediate 6a

A mixture of 6-(trifluoromethoxy)indoline [CAS 959235-95-1] (837 mg, 4.12 mmol), 2-(2-(2-((tert-butyldimethylsilyl)oxy)ethoxy)-4-chlorophenyl)-2-((3-methoxy-5-(1H-1,2,4-triazol-1-yl)phenyl)amino)acetic acid 5d (2.196 g, 4.12 mmol), HATU (2.35 g, 6.18 mmol) and diisopropylethylamine (2 mL, 12.36 mmol) in DMF (20 mL) was stirred at room temperature for 2 h. The mixture was diluted with water. The resulting gummy material was taken up with EtOAc, washed with a solution of K$_2$CO$_3$ 10% in water, water, dried over MgSO$_4$, filtered and the solvent was concentrated under reduced pressure. The residue was purified by flash chromatography on silica gel (15-40 μm, 80 g, heptane/EtOAc gradient 70/30 to 60/40). The pure fractions were combined and the solvent was concentrated under reduced pressure to give 2-(2-(2-((tert-butyldimethylsilyl)oxy)ethoxy)-4-chlorophenyl)-2-((3-methoxy-5-(1H-1,2,4-triazol-1-yl)phenyl)amino)-1-(6-(trifluoromethoxy)indolin-1-yl)ethanone 6a (1.65 g).

Synthesis of Compound 6 and Chiral Separation into Enantiomers 6A and 6B

Under a N$_2$ flow, at 5° C., 4M HCl in dioxane (6.5 mL, 21.6 mmol) was added dropwise to a solution of 2-(2-(2-((tert-butyldimethylsilyl)oxy)ethoxy)-4-chlorophenyl)-2-((3-methoxy-5-(1H-1,2,4-triazol-1-yl)phenyl)amino)-1-(6-(trifluoromethoxy)indolin-1-yl)ethanone 6a (1.85 g, 2.58 mmol) in MeOH (40 mL). The reaction was stirred at room temperature for 1 h. The mixture was cooled to 0° C., basified with a 10% aqueous solution of K$_2$CO$_3$ and extracted with EtOAc. The organic phase was separated, dried over MgSO$_4$, filtered and the solvent was concentrated under reduced pressure. The compound was crystallized from CH$_2$Cl$_2$ to afford 2-(4-chloro-2-(2-hydroxyethoxy)phenyl)-2-((3-methoxy-5-(1H-1,2,4-triazol-1-yl)phenyl)amino)-1-(6-(trifluoromethoxy)indolin-1-yl)ethanone 6 (1.47 g) as a racemate.

The enantiomers of Compound 6 were separated via Preparative Chiral SFC (Stationary phase: Chiralpak® IC 5 µm 250×30 mm, Mobile phase: 70% CO$_2$, 30% iPrOH (+0.3% iPrNH$_2$)). The first eluted enantiomer (585 mg) was further purified by flash chromatography on silica gel (15-40 µm, 24 g, CH$_2$Cl$_2$/MeOH 99/1) to give, after solidification in MeOH/diisopropyl ether/heptane, Enantiomer 6A (491 mg).

The second eluted enantiomer (400 mg) was further purified by flash chromatography on silica gel (15-40 µm, 24 g, CH$_2$Cl$_2$/MeOH 99/1) to give, after solidification in MeOH/diisopropyl ether/heptane, Enantiomer 6B (467 mg).

Compound 6:
$^1$H NMR (400 MHz, DMSO-d$_6$) δ ppm 3.08-3.23 (m, 2H) 3.73 (s, 3H) 3.75-3.84 (m, 2H) 4.07-4.22 (m, 3H) 4.37-4.49 (m, 1H) 4.94 (br s, 1H) 5.82 (d, J=8.6 Hz, 1H) 6.35 (s, 1H) 6.64-6.68 (m, 1H) 6.79-6.86 (m, 2H) 6.98-7.05 (m, 2H) 7.15 (d, J=2.0 Hz, 1H) 7.34 (d, J=8.6 Hz, 1H) 7.37 (d, J=8.1 Hz, 1H) 8.04 (s, 1H) 8.15 (s, 1H) 9.11 (s, 1H)

LC/MS (method LC-A): R$_t$ 3.27 min, MH$^+$ 604
Melting point: 161° C.

Enantiomer 6A:
$^1$H NMR (500 MHz, DMSO-d$_6$) δ ppm 3.10-3.25 (m, 2H) 3.73 (s, 3H) 3.74-3.84 (m, 2H) 4.06-4.23 (m, 3H) 4.39-4.48 (m, 1H) 4.99 (br t, J=5.4 Hz, 1H) 5.83 (br d, J=8.5 Hz, 1H) 6.36 (br s, 1H) 6.67 (s, 1H) 6.84 (s, 1H) 6.88 (br d, J=8.5 Hz, 1H) 7.03 (br t, J=7.6 Hz, 2H) 7.16 (s, 1H) 7.36 (dd, J=11.8, 8.4 Hz, 2H) 8.04 (br s, 1H) 8.17 (s, 1H) 9.14 (s, 1H)

LC/MS (method LC-A): R$_t$ 3.25 min, MH$^+$ 604
$[α]_D^{20}$: +45.9° (c 0.29, DMF)
Chiral SFC (method SFC-D): R$_t$ 4.20 min, MH$^+$ 604, chiral purity 100%.

Enantiomer 6B:
$^1$H NMR (500 MHz, DMSO-d$_6$) δ ppm 3.09-3.25 (m, 2H) 3.73 (s, 3H) 3.74-3.83 (m, 2H) 4.06-4.21 (m, 3H) 4.43 (td, J=10.2, 6.6 Hz, 1H) 4.98 (t, J=5.4 Hz, 1H) 5.83 (d, J=8.5 Hz, 1H) 6.35 (s, 1H) 6.66 (s, 1H) 6.83 (s, 1H) 6.88 (d, J=8.8 Hz, 1H) 6.99-7.06 (m, 2H) 7.15 (d, J=1.6 Hz, 1H) 7.36 (dd, J=12.6, 8.2 Hz, 2H) 8.04 (s, 1H) 8.16 (s, 1H) 9.14 (s, 1H)

LC/MS (method LC-A): R$_t$ 3.31 min, MH$^+$ 604
$[α]_D^{20}$: −46.3° (c 0.3, DMF)
Chiral SFC (method SFC-D): R$_t$ 5.30 min, MH$^+$ 604, chiral purity 100%.

Example 6 (Method 2): Synthesis of 2-(4-chloro-2-(2-hydroxyethoxy)phenyl)-2-((3-methoxy-5-(1H-1,2,4-triazol-1-yl)phenyl)amino)-1-(6-(trifluoromethoxy)indolin-1-yl)ethanone (Compound 6)

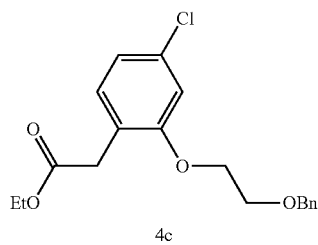
4c

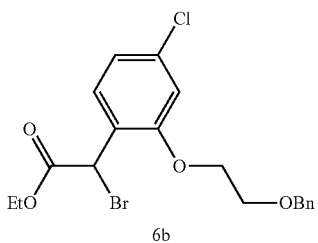
6b

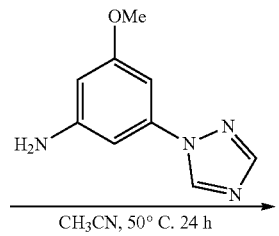

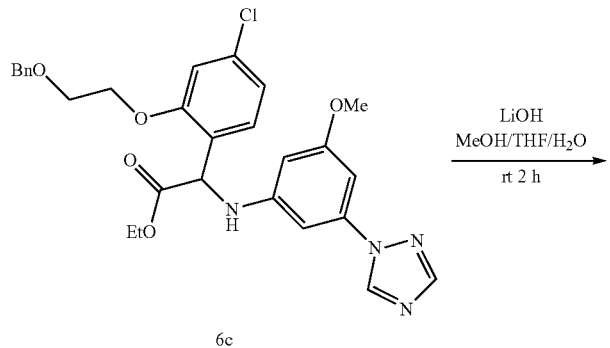
6c

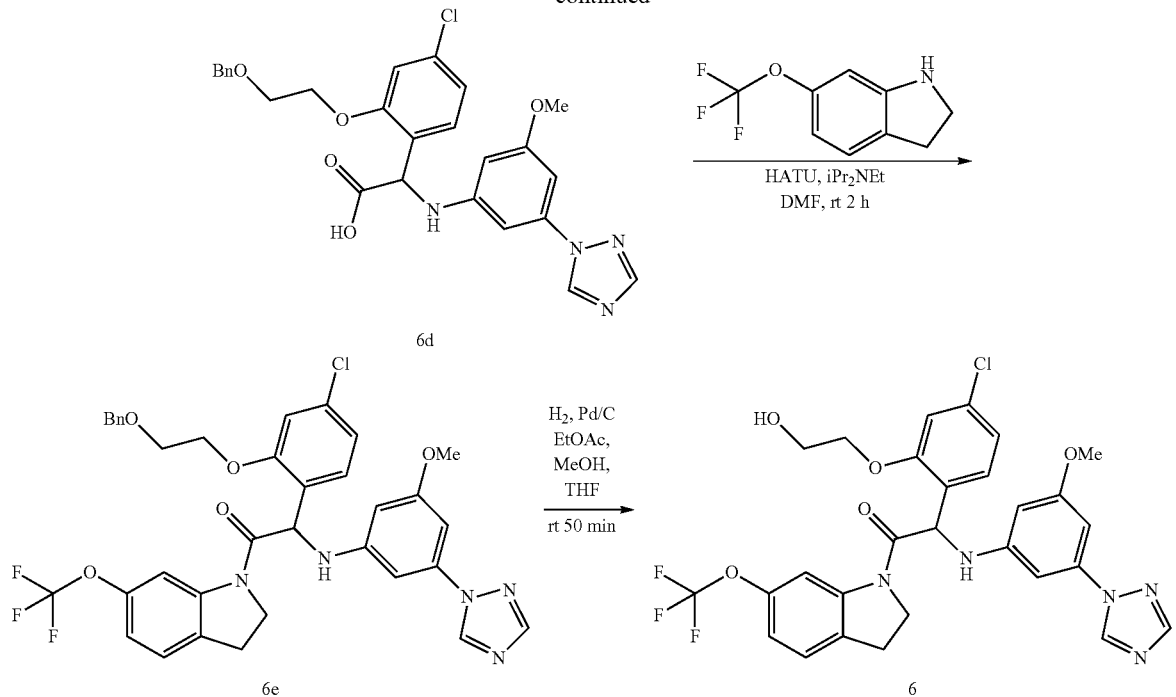

Synthesis of Intermediate 6b

To a 1.5M lithium bis(trimethylsilyl)amide solution in THF (23 mL, 34.4 mmol) cooled at −70° C. under a $N_2$ flow was added a solution of ethyl 2-(4-chloro-2-hydroxyphenyl) acetate 4c (6 g, 17.2 mmol) in THF (35 mL). After 1 h at −70° C., chlorotrimethylsilane (3.5 mL, 27.5 mmol) was added. The reaction mixture was stirred at −70° C. for 15 min. N-Bromosuccinimide (3.7 g, 20.6 mmol) in THF (35 mL) was added and stirring was continued at −70° C. for 2 h. The reaction mixture was poured out into $H_2O$ and extracted with EtOAc. The organic phases were combined, dried over $MgSO_4$, filtered and concentrated under reduced pressure to give ethyl 2-(2-(2-(benzyloxy)ethoxy)-4-chlorophenyl)-2-bromoacetate 6b (8.2 g) which was used in the next step without further purification.

Synthesis of Intermediate 6c

A mixture of 2-(2-(2-(benzyloxy)ethoxy)-4-chlorophenyl)-2-bromoacetate 6b (6.5 g, 15.2 mmol), 3-methoxy-5-(1H-1,2,4-triazol-1-yl)aniline [CAS 1220630-56-7] (4.6 g, 24.1 mmol) and diisopropylethylamine (5.3 mL, 30.4 mmol) in $CH_3CN$ (130 mL) was stirred at 50° C. for 24 h. The solvent was concentrated under reduced pressure. The residue was diluted with EtOAc. The solution was filtered to remove solid particles (residual aniline). The organic layer was concentrated under reduced pressure. The residue was purified by flash chromatography on silica gel (15-40 μm, 120 g, heptane/EtOAc gradient 80/20 to 70/30). The pure fractions were combined and the solvent was removed under reduced pressure to give ethyl 2-(2-(2-(benzyloxy)ethoxy)-4-chlorophenyl)-2-((3-methoxy-5-(1H-1,2,4-triazol-1-yl)phenyl)amino)acetate 6c (4.8 g).

Synthesis of Intermediate 6d

At 10° C., Lithium hydroxide monohydrate (500 mg, 11.9 mmol) was added to a solution of ethyl 2-(2-(2-(benzyloxy) ethoxy)-4-chlorophenyl)-2-((3-methoxy-5-(1H-1,2,4-triazol-1-yl)phenyl)amino)acetate 6c (3.2 g, 5.96 mmol) in MeOH/THF/water (1/1/1) (50 mL). The mixture was stirred at room temperature for 2 h. The mixture was diluted with ice water and cooled to 0° C. The resulting mixture was acidified up to pH 6-7 with 0.5N HCl and extracted with EtOAc. The organic layers were combined, dried over $MgSO_4$, filtered and the solvent was concentrated under reduced pressure to give 2-(2-(2-(benzyloxy)ethoxy)-4-chlorophenyl)-2-((3-methoxy-5-(1H-1,2,4-triazol-1-yl)phenyl)amino)acetic acid 6d (2.75 g). The compound was used in the next reaction step without further purification.

Synthesis of Intermediate 6e

A mixture of 6-(trifluoromethoxy)indoline [CAS 959235-95-1] (1.2 g, 5.89 mmol), 2-(2-(2-(benzyloxy)ethoxy)-4-chlorophenyl)-2-((3-methoxy-5-(1H-1,2,4-triazol-1-yl)phenyl)amino)acetic acid 6d (2.5 g, 4.91 mmol), HATU (2.29 g, 6.01 mmol) and diisopropylethylamine (1.99 mL, 12.0 mmol) in DMF (18 mL) was stirred at room temperature for 2 h. The mixture was diluted with water. The precipitate was filtered off and washed with water. The precipitate was taken up with EtOAc, washed with a solution of $K_2CO_3$ 10% in water, water, dried over $MgSO_4$, filtered and the solvent was concentrated under reduced pressure. The compound was purified by flash chromatography on silica gel (15-40 μm, 220 g, heptane/EtOAc 50/50). The pure fractions were combined and the solvent was concentrated under reduced pressure to give 2-(2-(2-(benzyloxy)ethoxy)-4-chlorophenyl)-2-((3-methoxy-5-(1H-1,2,4-triazol-1-yl)phenyl) amino)-1-(6-(trifluoromethoxy)indolin-1-yl)ethanone 6e (2.5 g).

Synthesis of Compound 6

A mixture of 2-(2-(2-(benzyloxy)ethoxy)-4-chlorophenyl)-2-((3-methoxy-5-(1H-1,2,4-triazol-1-yl)phenyl)

amino)-1-(6-(trifluoromethoxy)indolin-1-yl)ethanone 6e (2 g, 2.88 mmol) in EtOAc/MeOH/THF (1/1/1) (100 mL) was hydrogenated for 50 min under atmospheric pressure of H$_2$ with Pd/C (10%) (3.07 g, 2.88 mmol) as the catalyst. The reaction was diluted with MeOH and filtered through a pad of Celite®. The filtrate was concentrated under reduced pressure. The residue (1.42 g) was combined with another batch (total amount: 1.65 g) and purified via achiral SFC (stationary phase: NH$_2$ 5 μm 150×30 mm, mobile phase: 70% CO$_2$, 30% iPrOH (+0.3% iPrNH$_2$)). The pure fractions were combined and the solvent was concentrated under reduced pressure to give 2-(4-chloro-2-(2-hydroxyethoxy)phenyl)-2-((3-methoxy-5-(1H-1,2,4-triazol-1-yl)phenyl)amino)-1-(6-(trifluoromethoxy)indolin-1-yl)ethanone 6 (1.36 g) as a racemate.

Example 7: Synthesis of 2-(4-chloro-2-(2-hydroxyethoxy)phenyl)-1-(5-fluoro-6-(trifluoromethyl)indolin-1-yl)-2-((3-methoxy-5-(1H-1,2,4-triazol-1-yl)phenyl)amino)ethanone (Compound 7) and Chiral Separation into Enantiomers 7A and 7B

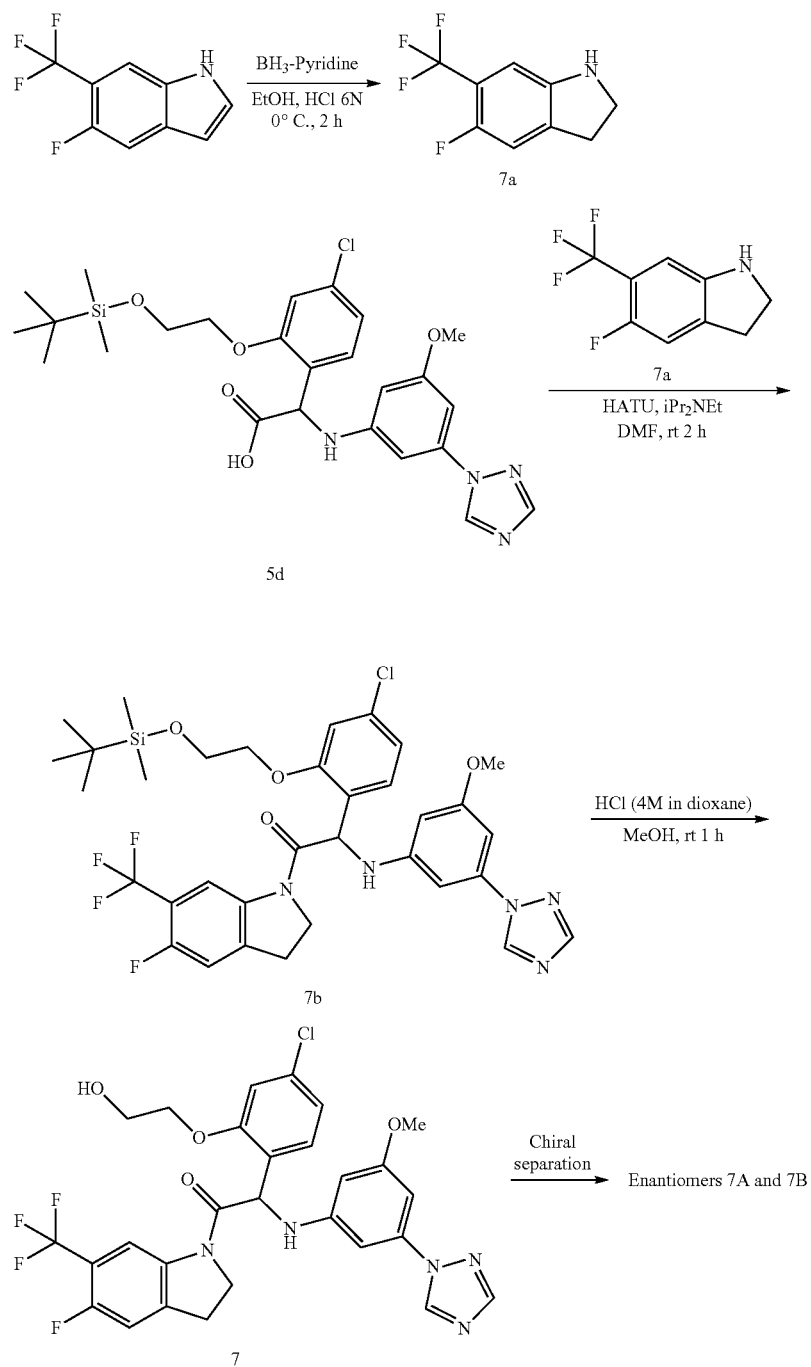

Synthesis of Intermediate 7a

At 0° C., BH$_3$-Pyridine (10.45 mL, 103.4 mmol) was added dropwise to a solution of 5-fluoro-6-(trifluoromethyl)-1H-indole [CAS 1493800-10-4] (7 g, 34.5 mmol) in EtOH (45 mL). 6N HCl (105 mL) was slowly added while maintaining the temperature below 10° C. The mixture was stirred at 0° C. for 2 h. Water (210 mL) was added and the mixture was basified to pH 8-9 with a concentrated aqueous solution of NaOH (the reaction temperature was kept below 20° C.). EtOAc was added. The organic layer was separated, washed with water, dried over MgSO$_4$, filtered and the solvent was concentrated under reduced pressure. The residue was co-evaporated under reduced pressure with toluene. The crude was purified by flash chromatography on silica gel (20-45 μm, 120 g, CH$_2$Cl$_2$/MeOH 98.5/1.5). The pure fractions were combined and the solvent was removed under reduced pressure to give 5-fluoro-6-(trifluoromethyl)indoline 7a (3.5 g).

Synthesis of Intermediate 7b

A mixture of 5-fluoro-6-(trifluoromethyl)indoline 7a (385 mg, 1.88 mmol), 24242-((tert-butyldimethylsilyl)oxy)ethoxy)-4-chlorophenyl)-2-((3-methoxy-5-(1H-1,2,4-triazol-1-yl)phenyl)amino)acetic acid 5d (1 g, 1.88 mmol), HATU (1.07 g, 2.814 mmol) and diisopropylethylamine (930 μL, 5.63 mmol) in DMF (10 mL) was stirred at room temperature for 2 h. The mixture was diluted with water. The resulting gummy material was taken up with EtOAc. The organic layer was washed with a solution of K$_2$CO$_3$ 10% in water, water, dried over MgSO$_4$, filtered and the solvent was concentrated under reduced pressure to give 2-(2-(2-((tert-butyldimethylsilyl)oxy)ethoxy)-4-chlorophenyl)-1-(5-fluoro-6-(trifluoromethyl)indolin-1-yl)-2-((3-methoxy-5-(1H-1,2,4-triazol-1-yl)phenyl)amino)ethanone 7b (1.4 g).

Synthesis of Compound 7 and Chiral Separation into Enantiomers 7A and 7B

Under a N$_2$ flow, at 5° C., 4M HCl in dioxane (4.9 mL, 19.4 mmol) was added dropwise to a solution of 2-(2-(2-((tert-butyldimethylsilyl)oxy)ethoxy)-4-chlorophenyl)-1-(5-fluoro-6-(trifluoromethyl)indolin-1-yl)-2-((3-methoxy-5-(1H-1,2,4-triazol-1-yl)phenyl)amino)ethanone 7b (1.4 g, 1.94 mmol) in MeOH (25 mL). The reaction was stirred at room temperature for 1 h. The mixture was cooled to 0° C., basified with a 10% aqueous solution of K$_2$CO$_3$ and extracted with EtOAc. The organic layer was separated, dried over MgSO$_4$, filtered and the solvent was concentrated under reduced pressure. The residue was purified by flash chromatography on silica gel (15-40 μm, 40 g, CH$_2$Cl$_2$/MeOH 98/2). The pure fractions were combined and the solvent was concentrated under reduced pressure to give 2-(4-chloro-2-(2-hydroxyethoxy)phenyl)-1-(5-fluoro-6-(trifluoromethyl)indolin-1-yl)-2-((3-methoxy-5-(1H-1,2,4-triazol-1-yl)phenyl)amino)ethanone 7 (737 mg) as a racemate.

The enantiomers of Compound 7 were separated via Preparative Chiral SFC (Stationary phase: Chiralpak® AD-H 5 μm 250×30 mm, Mobile phase: 60% CO$_2$, 40% EtOH (+0.3% iPrNH$_2$)). The first eluted enantiomer (325 mg) was crystallized from diisopropyl ether/petroleum ether to give Enantiomer 7A (244 mg). The second eluted enantiomer (310 mg) was crystallized from diisopropyl ether/petroleum ether to give Enantiomer 7B (220 mg).

Compound 7:
$^1$H NMR (500 MHz, DMSO-d$_6$) δ ppm 3.19-3.30 (m, 2H) 3.63-3.87 (m, 5H) 4.05-4.24 (m, 3H) 4.40-4.49 (m, 1H) 4.97 (br s, 1H) 5.83 (br d, J=6.9 Hz, 1H) 6.35 (br s, 1H) 6.67 (br s, 1H) 6.80-6.89 (m, 2H) 7.03 (br d, J=7.3 Hz, 1H) 7.15 (br s, 1H) 7.37 (br d, J=7.6 Hz, 1H) 7.47 (br d, J=9.5 Hz, 1H) 8.16 (br s, 1H) 8.39 (br d, J=4.4 Hz, 1H) 9.14 (br s, 1H)

LC/MS (method LC-B): R$_t$ 3.14 min, MH$^+$ 606

Melting point: 140° C.

Enantiomer 7A:
$^1$H NMR (500 MHz, DMSO-d$_6$) δ ppm 3.20-3.30 (m, 2H) 3.69-3.86 (m, 5H) 4.06-4.23 (m, 3H) 4.40-4.50 (m, 1H) 4.98 (br t, J=5.2 Hz, 1H) 5.83 (br d, J=8.8 Hz, 1H) 6.35 (br s, 1H) 6.67 (s, 1H) 6.82-6.89 (m, 2H) 7.03 (br d, J=8.2 Hz, 1H) 7.16 (s, 1H) 7.37 (d, J=8.2 Hz, 1H) 7.47 (br d, J=10.1 Hz, 1H) 8.17 (s, 1H) 8.39 (br d, J=6.3 Hz, 1H) 9.14 (s, 1H)

LC/MS (method LC-A): R$_t$ 3.27 min, MH$^+$ 606

[α]$_D^{20}$: −44.3° (c 0.282, DMF)

Chiral SFC (method SFC-B): R$_t$ 2.89 min, MH$^+$ 606, chiral purity 100%.

Melting point: 166° C.

Enantiomer 7B:
$^1$H NMR (500 MHz, DMSO-d$_6$) δ ppm 3.18-3.30 (m, 2H) 3.69-3.86 (m, 5H) 4.07-4.22 (m, 3H) 4.40-4.50 (m, 1H) 4.97 (br t, J=5.2 Hz, 1H) 5.83 (br d, J=8.8 Hz, 1H) 6.35 (br s, 1H) 6.67 (s, 1H) 6.81-6.89 (m, 2H) 7.03 (br d, J=8.2 Hz, 1H) 7.16 (s, 1H) 7.37 (br d, J=8.2 Hz, 1H) 7.47 (br d, J=10.1 Hz, 1H) 8.17 (s, 1H) 8.39 (br d, J=6.3 Hz, 1H) 9.14 (s, 1H)

LC/MS (method LC-A): R$_t$ 3.27 min, MH$^+$ 606

[α]$_D^{20}$: +35.6° (c 0.281, DMF)

Chiral SFC (method SFC-B): R$_t$ 4.92 min, MH$^+$ 606, chiral purity 100%.

Melting point: 100° C.

Example 8: Synthesis of 2-(4-chloro-2-(2-hydroxyethoxy)phenyl)-2-((3-methoxy-5-(1H-1,2,4-triazol-1-yl)phenyl)amino)-1-(5-methoxy-6-(trifluoromethoxy)indolin-1-yl)ethanone (Compound 8) and Chiral Separation into Enantiomers 8A and 8B

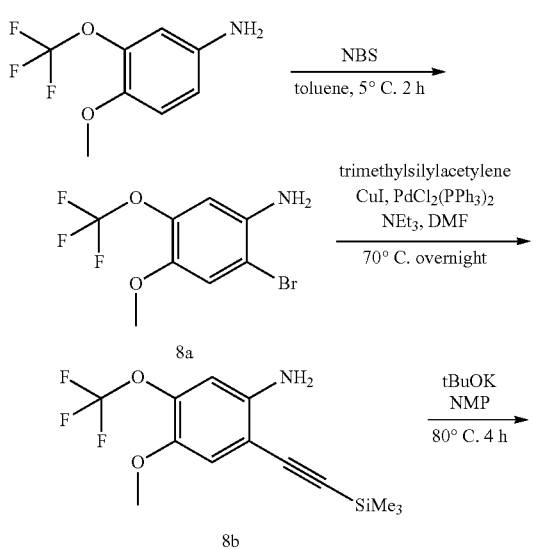

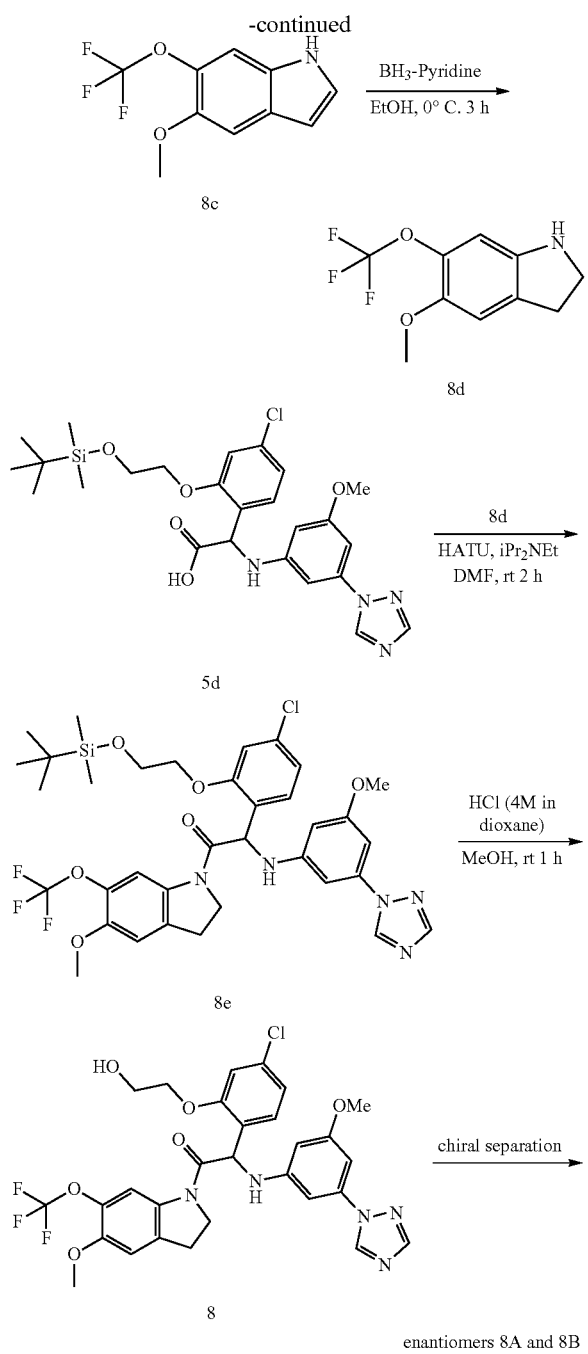

Synthesis of Intermediate 8b

A solution of 2-bromo-4-methoxy-5-(trifluoromethoxy) aniline 8a (2.72 g, 9.51 mmol) in DMF (30 mL) was degassed with $N_2$ for 15 min. Dichlorobis(triphenylphosphine)palladium(II) (667 mg, 0.95 mmol), copper(I) iodide (362 mg, 1.90 mmol), triethylamine (3.96 mL, 28.53 mmol) and trimethylsilylacetylene (3.95 mL, 28.5 mmol) were added. The reaction mixture was heated at 70° C. for 12 h under a $N_2$ flow. After cooling to room temperature, the reaction mixture was diluted with $H_2O$ and extracted with EtOAc. The organic phases were combined, dried over $MgSO_4$, filtered and concentrated under reduced pressure. The residue was purified by flash chromatography on silica gel (15-40 µm, 80 g, heptane/EtOAc 85/15). The pure fractions were combined and evaporated to dryness to give 4-methoxy-5-(trifluoromethoxy)-2-((trimethylsilyl)ethynyl) aniline 8b (1.4 g).

Synthesis of Intermediate 8c

To a solution of 4-methoxy-5-(trifluoromethoxy)-2-((trimethylsilyl)ethynyl)aniline 8b (1.2 g, 3.96 mmol) in NMP (11 mL) under a $N_2$ flow, was added tBuOK (1.33 g, 11.9 mmol) in one portion. The reaction mixture was heated at 80° C. for 4 h, poured out into ice/water and acidified with 3N HCl to pH 4-5. The reaction mixture was extracted with EtOAc. The organic phases were combined, washed with $H_2O$, dried over $MgSO_4$, filtered and concentrated under reduced pressure. The residue was purified by flash chromatography on silica gel (15-40 µm, 40 g, heptane/EtOAc 85/15). The pure fractions were combined and evaporated to dryness to give 5-methoxy-6-(trifluoromethoxy)-1H-indole 8c (490 mg).

Synthesis of Intermediate 8d

At 0° C., $BH_3$-Pyridine (10.5 mL, 103.8 mmol) was added dropwise to a solution of 5-methoxy-6-(trifluoromethoxy)-1H-indole 8c (8 g, 34.6 mmol) in EtOH (45 mL). 6N HCl (6 mL) was added dropwise while maintaining the temperature below 10° C. The mixture was stirred at 0° C. for 3 h. Water (210 mL) was added and the mixture was basified to pH 8-9 with a concentrated solution of NaOH in water (the reaction temperature was kept below 20° C.). The mixture was extracted with EtOAc. The organic layer was washed with water, dried over $MgSO_4$, filtered and the solvent was evaporated under reduced pressure. Toluene was added and the solution was concentrated under reduced pressure to give 5-methoxy-6-(trifluoromethoxy)indoline 8d (7.5 g).

Synthesis of Intermediate 8e

A mixture of 5-methoxy-6-(trifluoromethoxy)indoline 8d (437 mg, 1.88 mmol), 2-(2-(2-((tert-butyldimethylsilyl)oxy) ethoxy)-4-chlorophenyl)-2-((3-methoxy-5-(1H-1,2,4-triazol-1-yl)phenyl)amino)acetic acid 5d (1 g, 1.88 mmol), HATU (1.07 g, 2.81 mmol) and diisopropylethylamine (930 µL, 5.63 mmol) in DMF (10 mL) was stirred at room temperature for 2 h. The mixture was diluted with water. The resulting gummy material was taken up with EtOAc. The organic solution was washed with a solution of $K_2CO_3$ 10% in water, water, dried over $MgSO_4$, filtered and the solvent was concentrated under reduced pressure to give 2-(2-(2-((tert-butyldimethylsilyl)oxy)ethoxy)-4-chlorophenyl)-2-((3-methoxy-5-(1H-1,2,4-triazol-1-yl)phenyl)amino)-1-(5-

Synthesis of Intermediate 8a

A solution of 4-methoxy-3-(trifluoromethoxy)aniline [CAS 647855-21-8] (3.1 g, 15.0 mmol) in toluene (50 mL) was treated with N-bromosuccinimide (2.8 g, 15.7 mmol) at 5° C. and the resulting mixture was stirred at 5-10° C. for 2 h. The mixture was diluted with water and extracted with EtOAc. The combined extracts were dried over $MgSO_4$, filtered and evaporated under reduced pressure. Purification was performed by flash chromatography on silica gel (15-40 µm, 24 g, heptane/EtOAc gradient 95/5 to 90/10) The pure fractions were combined and evaporated to dryness to give 2-bromo-4-methoxy-5-(trifluoromethoxy)aniline 8a (2.5 g).

methoxy-6-(trifluoromethoxy)indolin-1-yl)ethanone 8e (1.5 g). The compound was used as such in the next reaction step.

Synthesis of Compound 8 and Chiral Separation into Enantiomers 8A and 8B

Under a $N_2$ flow, at 5° C., 4M HCl in dioxane (4.9 mL, 19.4 mmol) was added dropwise to a solution of 2-(2-(2-((tert-butyldimethylsilyl)oxy)ethoxy)-4-chlorophenyl)-2-((3-methoxy-5-(1H-1,2,4-triazol-1-yl)phenyl)amino)-1-(5-methoxy-6-(trifluoromethoxy)indolin-1-yl)ethanone 8e (1.4 g, 1.94 mmol) in MeOH (25 mL). The reaction was stirred at room temperature for 1 h. The mixture was cooled to 0° C., basified with a 10% aqueous solution of $K_2CO_3$ and extracted with EtOAc. The organic layer was separated, dried over $MgSO_4$, filtered and the solvent was concentrated under reduced pressure. The residue was purified by flash chromatography on silica gel (15-40 μm, 40 g, $CH_2Cl_2$/MeOH/$NH_4OH$ 98.4/1.5/0.1).

The pure fractions were combined and the solvent was concentrated under reduced pressure to give, after crystallization from $CH_2Cl_2$, 2-(4-chloro-2-(2-hydroxyethoxy)phenyl)-2-((3-methoxy-5-(1H-1,2,4-triazol-1-yl)phenyl)amino)-1-(5-methoxy-6-(trifluoromethoxy)indolin-1-yl)ethanone 8 (850 mg) as a racemate.

The enantiomers of Compound 8 were separated via Preparative Chiral SFC (Stationary phase: Chiralpak® IC 5 μm 250×30 mm, Mobile phase: 60% $CO_2$, 40% iPrOH). The first eluted enantiomer (410 mg) was solidified by trituration with diisopropyl ether to give Enantiomer 8A (314 mg). The second eluted enantiomer (388 mg) was solidified by trituration with diisopropyl ether to give Enantiomer 8B (300 mg).

Compound 8:
$^1$H NMR (400 MHz, DMSO-$d_6$) δ ppm 3.07-3.27 (m, 2H) 3.70-3.85 (m, 8H) 4.07-4.19 (m, 3H) 4.35-4.45 (m, 1H) 4.97 (t, J=5.6 Hz, 1H) 5.80 (d, J=8.6 Hz, 1H) 6.34 (s, 1H) 6.63-6.67 (m, 1H) 6.80-6.87 (m, 2H) 7.02 (dd, J=8.1, 2.0 Hz, 1H) 7.14 (d, J=2.0 Hz, 1H) 7.20 (s, 1H) 7.37 (d, J=8.6 Hz, 1H) 8.06 (s, 1H) 8.15 (s, 1H) 9.12 (s, 1H)

LC/MS (method LC-A): $R_t$ 3.20 min, MH$^+$ 634

Melting point: 181° C.

Enantiomer 8A:
$^1$H NMR (500 MHz, DMSO-$d_6$) δ ppm 3.09-3.26 (m, 2H) 3.70-3.85 (m, 8H) 4.08-4.20 (m, 3H) 4.40 (td, J=10.3, 6.5 Hz, 1H) 4.99 (br t, J=5.4 Hz, 1H) 5.81 (d, J=8.5 Hz, 1H) 6.35 (s, 1H) 6.66 (s, 1H) 6.83 (s, 1H) 6.86 (d, J=8.8 Hz, 1H) 7.03 (dd, J=8.2, 1.3 Hz, 1H) 7.15 (d, J=1.6 Hz, 1H) 7.21 (s, 1H) 7.38 (d, J=8.2 Hz, 1H) 8.07 (s, 1H) 8.16 (s, 1H) 9.13 (s, 1H)

LC/MS (method LC-B): $R_t$ 3.09 min, MH$^+$ 634

$[\alpha]_D^{20}$: −39.3° (c 0.3, DMF)

Chiral SFC (method SFC-E): $R_t$ 3.39 min, MH$^+$ 634, chiral purity 100%.

Enantiomer 8B:
$^1$H NMR (500 MHz, DMSO-$d_6$) δ ppm 3.09-3.27 (m, 2H) 3.70-3.85 (m, 8H) 4.06-4.19 (m, 3H) 4.40 (td, J=10.2, 6.6 Hz, 1H) 4.99 (br t, J=5.2 Hz, 1H) 5.81 (d, J=8.5 Hz, 1H) 6.35 (s, 1H) 6.66 (s, 1H) 6.83 (s, 1H) 6.86 (d, J=8.8 Hz, 1H) 7.03 (dd, J=8.2, 1.6 Hz, 1H) 7.15 (d, J=1.6 Hz, 1H) 7.21 (s, 1H) 7.38 (d, J=8.2 Hz, 1H) 8.07 (s, 1H) 8.16 (s, 1H) 9.13 (s, 1H)

LC/MS (method LC-A): $R_t$ 3.07 min, MH$^+$ 634

$[\alpha]_D^{20}$: −44.4° (c 0.295, DMF)

Chiral SFC (method SFC-E): $R_t$ 5.69 min, MH$^+$ 634, chiral purity 100%.

Example 9: Synthesis of 2-(4-chloro-2-(2-hydroxyethoxy)phenyl)-1-(5-fluoro-6-(trifluoromethoxy)indolin-1-yl)-2-((3-methoxy-5-(1H-1,2,4-triazol-1-yl)phenyl)amino)ethanone (Compound 9) and Chiral Separation into Enantiomers 9A and 9B

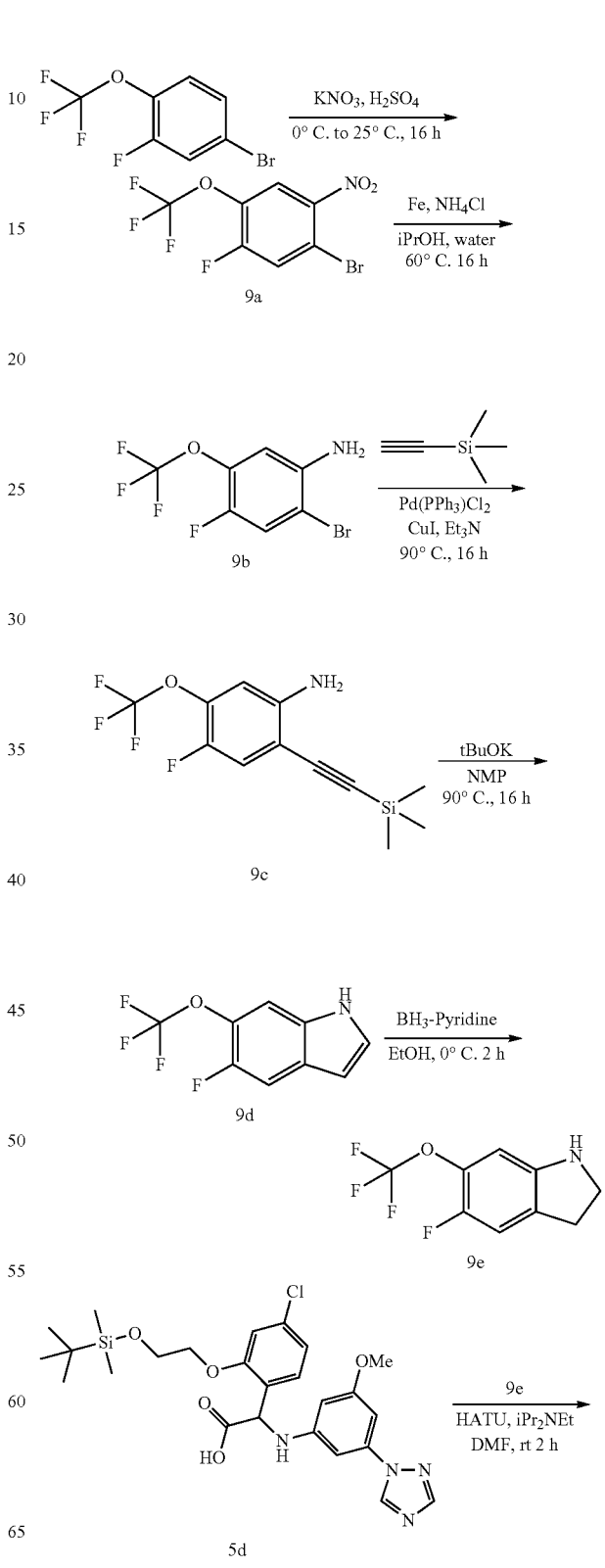

-continued

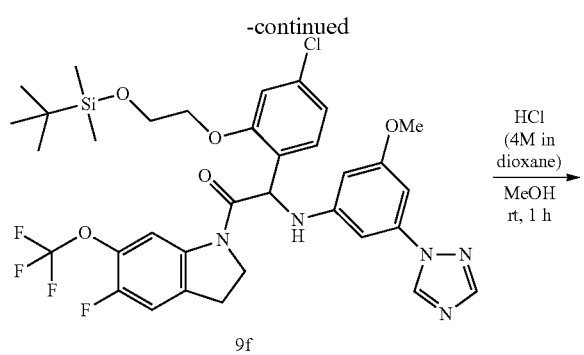

9f

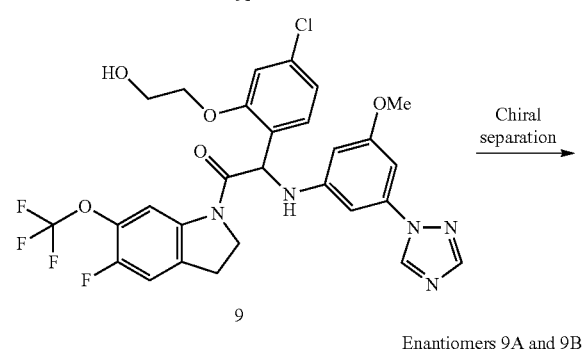

9

Enantiomers 9A and 9B

Synthesis of Intermediate 9a

A solution of 4-bromo-2-fluoro-1-(trifluoromethoxy)benzene [CAS 105529-58-6] (98.7 g, 381.1 mmol) in concentrated $H_2SO_4$ (98%, 200 mL), was cooled to 0° C. with an ice-bath. $KNO_3$ (43.0 g, 425.3 mmol) was added portionwise. After addition, the ice-bath was removed and the mixture was stirred at room temperature for 16 h. The reaction mixture was poured out into ice-water (2 L) while stirring. The mixture was extracted with $CH_2Cl_2$ (3×500 mL). The combined organic layers were washed with a saturated aqueous $NaHCO_3$ solution (2×500 mL), brine (500 mL), dried over $MgSO_4$, filtered and concentrated under reduced pressure to afford 1-bromo-5-fluoro-2-nitro-4-(trifluoromethoxy)benzene 9a (117.2 g), which was used in the next step without further purification.

Synthesis of Intermediate 9b

To a stirred suspension of 1-bromo-5-fluoro-2-nitro-4-(trifluoromethoxy)benzene 9a (70.0 g, 230 mmol) and $NH_4Cl$ (123.2 g, 2.30 mol) in iPrOH (1 L) and water (330 mL) was added reductive iron powder (64.3 g, 1.15 mol) under $N_2$-atmosphere. The reaction mixture was stirred at 60° C. for 16 h. The reaction mixture was diluted with EtOAc (1 L) and filtered through Celite®. The filtrate was concentrated under reduced pressure. The residue was partitioned between EtOAc (1 L) and water (800 mL). The layers were separated and the organic phase was washed with brine (1 L), dried over $MgSO_4$, filtered and concentrated under reduced pressure. The residue was purified by distillation under reduced pressure (oil pump, b.p. 60-64° C.). 2-Bromo-4-fluoro-5-(trifluoromethoxy)aniline 9b (47.3 g) was obtained as a yellow oil.

Synthesis of Intermediate 9c

To a mixture of 2-bromo-4-fluoro-5-(trifluoromethoxy) aniline 9b (18.4 g, 67.2 mmol), ethynyl(trimethyl)silane (19.9 g, 202.4 mmol, 28.00 mL) in $Et_3N$ (300 mL) was added CuI (1.28 g, 6.72 mmol) and $Pd(PPh_3)_2Cl_2$ (2.40 g, 3.42 mmol). The reaction mixture was heated under $N_2$-atmosphere at 90° C. for 16 h. After cooling to room temperature, the mixture was diluted with MTBE (300 mL) and filtered through Celite®. The filtrate was concentrated under reduced pressure. The residue was purified by flash chromatography on silica gel (ISCO®, 220 g SepaFlash® Silica Flash Column, eluent: gradient of 0 to 5% EtOAc in Petroleum ether @100 mL/min). 4-Fluoro-5-(trifluoromethoxy)-2-((trimethylsilyl)ethynyl)aniline 9c (16.1 g, 90% purity) was obtained as a brown oil.

Synthesis of Intermediate 9d

A mixture of 4-fluoro-5-(trifluoromethoxy)-2-((trimethylsilyl)ethynyl)aniline 9c (16.1 g, 55.3 mmol) and tBuOK (18.6 g, 165.8 mmol) in NMP (220.00 mL) was heated at 90° C. for 16 h under $N_2$-atmosphere. After cooling to room temperature, the reaction mixture was poured out into ice-water (1 L) and extracted with MTBE (3×300 mL). The combined organic phases were washed with water (2×200 mL), brine (300 mL), dried over $MgSO_4$, filtered and concentrated under reduced pressure. The residue was purified by flash chromatography on silica gel (ISCO®, 120 g SepaFlash® Silica Flash Column, eluent: gradient of 0 to 5% EtOAc in Petroleum ether @ 85 mL/min) to afford 5-fluoro-6-(trifluoromethoxy)-1H-indole 9d (11 g) product as a dark-green oil. The residue was combined with another fraction (total amount=17.2 g) and further purified by distillation under reduced pressure (oil pump, b.p. 60-64° C.) to provide 5-fluoro-6-(trifluoromethoxy)-1H-indole 9d (14.7 g, 95% purity) as a colorless oil.

Synthesis of Intermediate 9e

At 0° C., $BH_3$-Pyridine (13.8 mL, 136.9 mmol) was added dropwise to a solution of 5-fluoro-6-(trifluoromethoxy)-1H-indole 9d (6 g, 27.4 mmol) in EtOH (40 mL). 6N HCl (90 mL) was added dropwise while maintaining the temperature below 10° C. The mixture was stirred at 0° C. for 2 h. Water (100 mL) was added and the mixture was basified until pH 8-9 with a concentrated solution of NaOH in water (the reaction temperature was kept below 20° C.). The mixture was extracted with $CH_2Cl_2$. The organic layer was washed with water, dried over $MgSO_4$, filtered and the solvent was evaporated under reduced pressure. Toluene was added and the solution was concentrated under reduced pressure to give 5.52 g of 5-fluoro-6-(trifluoromethoxy)indoline 9e. The compound was used in the next reaction step without further purification.

Synthesis of Intermediate 9f

A mixture of 5-fluoro-6-(trifluoromethoxy)indoline 9e (169 mg, 0.76 mmol), 24242-((tert-butyldimethylsilyl)oxy) ethoxy)-4-chlorophenyl)-2-((3-methoxy-5-(1H-1,2,4-triazol-1-yl)phenyl)amino)acetic acid 5d (407 mg, 0.76 mmol), HATU (435 mg, 1.15 mmol) and diisopropylethylamine (379 μL, 2.29 mmol) in DMF (3.9 mL) was stirred at room temperature for 2 h. The mixture was diluted with water. The resulting gummy material was taken up with EtOAc. The organic solution was washed with a solution of $K_2CO_3$ 10% in water, water, dried over $MgSO_4$, filtered and the solvent was concentrated under reduced pressure. The residue was purified by flash chromatography on silica gel (15-40 μm, 24 g, heptane/EtOAc 70/30). The pure fractions were combined and the solvent concentrated under reduced pressure to give 2-(2-(2-((tert-butyldimethylsilyl)oxy)ethoxy)-4-chlorophenyl)-1-(5-fluoro-6-(trifluoromethoxy)indolin-1-yl)-2-((3-methoxy-5-(1H-1,2,4-triazol-1-yl)phenyl)amino)ethanone 9f (257 mg).

Synthesis of Compound 9 and Chiral Separation into Enantiomers 9A and 9B

Under a $N_2$ flow, at 5° C., 4M HCl in dioxane (873 μL, 3.49 mmol) was added dropwise to a solution of 2-(2-(2-((tert-butyldimethylsilyl)oxy)ethoxy)-4-chlorophenyl)-1-(5-fluoro-6-(trifluoromethoxy)indolin-1-yl)-2-((3-methoxy-5-(1H-1,2,4-triazol-1-yl)phenyl)amino)ethanone 9f (257 mg, 0.35 mmol) in MeOH (4 mL). The reaction was stirred at room temperature for 1 h. The mixture was cooled to 0° C., basified with a 10% aqueous solution of $K_2CO_3$ and extracted with EtOAc. The organic layer was separated, washed with water, dried over $MgSO_4$, filtered and the solvent was concentrated under reduced pressure. The residue was purified by flash chromatography on silica gel (15-40 μm, 12 g, $CH_2Cl_2$/MeOH 98.5/1.5). The pure fractions were combined and the solvent was concentrated under reduced pressure to give 2-(4-chloro-2-(2-hydroxyethoxy)phenyl)-1-(5-fluoro-6-(trifluoromethoxy)indolin-1-yl)-2-((3-methoxy-5-(1H-1,2,4-triazol-1-yl)phenyl)amino)ethanone 9 (210 mg) as a racemate. A small fraction (17 mg) was further purified via reverse phase chromatography (Stationary phase: YMC-actus Triart-C18 10 μm 30×150 mm, Mobile phase: Gradient from 50% $NH_4HCO_3$ 0.2%, 50% $CH_3CN$ to 0% $NH_4HCO_3$ 0.2%, 100% $CH_3CN$) to afford 7 mg. The residue was solidified by lyophilization from a solvent mixture of $CH_3CN$ (1 ml) and water (4 mL).

The enantiomers of Compound 9 (190 mg) were separated via Preparative Chiral SFC (Stationary phase: Chiralpak® AD-H 5 μm 250×30 mm, Mobile phase: 65% $CO_2$, 35% EtOH (+0.3% $iPrNH_2$)). The first eluted enantiomer (58 mg) was dissolved in $CH_3CN$ (2 ml), water (8 mL) was added and the mixture was lyophilized to give Enantiomer 9A (58 mg) as a powder. The second eluted enantiomer (59 mg) was dissolved in $CH_3CN$ (2 ml), water (8 mL) was added and the mixture was lyophilized to give Enantiomer 9B (59 mg) as a powder.

Compound 9:
$^1$H NMR (500 MHz, DMSO-$d_6$) δ ppm 3.13-3.30 (m, 2H) 3.72 (s, 3H) 3.70-3.80 (m, 2H) 4.06-4.22 (m, 3H) 4.42 (td, J=10.4, 6.3 Hz, 1H) 4.97 (br s, 1H) 5.82 (d, J=8.5 Hz, 1H) 6.34 (s, 1H) 6.66 (t, J=1.9 Hz, 1H) 6.82 (s, 1H) 6.87 (d, J=8.2 Hz, 1H) 7.03 (dd, J=8.2, 1.9 Hz, 1H) 7.15 (d, J=2.2 Hz, 1H) 7.36 (d, J=8.2 Hz, 1H) 7.45 (d, J=9.8 Hz, 1H) 8.14-8.18 (m, 2H)

LC/MS (method LC-A): $R_t$ 3.32 min, MH+ 622

Enantiomer 9A:
$^1$H NMR (400 MHz, DMSO-$d_6$) δ ppm 3.12-3.28 (m, 2H) 3.72 (s, 3H) 3.69-3.82 (m, 2H) 3.99-4.22 (m, 3H) 4.42 (td, J=10.0, 6.8 Hz, 1H) 4.96 (t, J=5.3 Hz, 1H) 5.81 (d, J=9.1 Hz, 1H) 6.34 (s, 1H) 6.66 (t, J=1.8 Hz, 1H) 6.80-6.88 (m, 2H) 7.02 (dd, J=8.1, 2.0 Hz, 1H) 7.15 (d, J=2.0 Hz, 1H) 7.36 (d, J=8.6 Hz, 1H) 7.45 (d, J=10.1 Hz, 1H) 8.13-8.18 (m, 2H) 9.13 (s, 1H)

LC/MS (method LC-B): $R_t$ 3.17 min, MH+ 622

$[\alpha]_D^{20}$: −35.1° (c 0.276, DMF)

Chiral SFC (method SFC-B): $R_t$ 2.75 min, MH+ 622, chiral purity 100%.

Enantiomer 9B:
$^1$H NMR (400 MHz, DMSO-$d_6$) δ ppm 3.12-3.28 (m, 2H) 3.72 (s, 3H) 3.69-3.82 (m, 2H) 3.99-4.22 (m, 3H) 4.42 (td, J=10.0, 6.8 Hz, 1H) 4.96 (t, J=5.3 Hz, 1H) 5.81 (d, J=9.1 Hz, 1H) 6.34 (s, 1H) 6.66 (t, J=1.8 Hz, 1H) 6.80-6.88 (m, 2H) 7.02 (dd, J=8.1, 2.0 Hz, 1H) 7.15 (d, J=2.0 Hz, 1H) 7.36 (d, J=8.6 Hz, 1H) 7.45 (d, J=10.1 Hz, 1H) 8.13-8.18 (m, 2H) 9.13 (s, 1H)

LC/MS (method LC-B): $R_t$ 3.17 min, MH+ 622

$[\alpha]_D^{20}$: +32.3° (c 0.254, DMF)

Chiral SFC (method SFC-B): $R_t$ 3.75 min, MH+ 622, chiral purity 100%.

Example 10: Synthesis of 2-(4-chloro-2-(2-hydroxyethoxy)phenyl)-2-((3-methoxy-5-(1H-1,2,4-triazol-1-yl)phenyl)amino)-1-(4-methyl-6-(trifluoromethoxy)indolin-1-yl)ethanone (Compound 10) and Chiral Separation into Enantiomers 10A and 10B

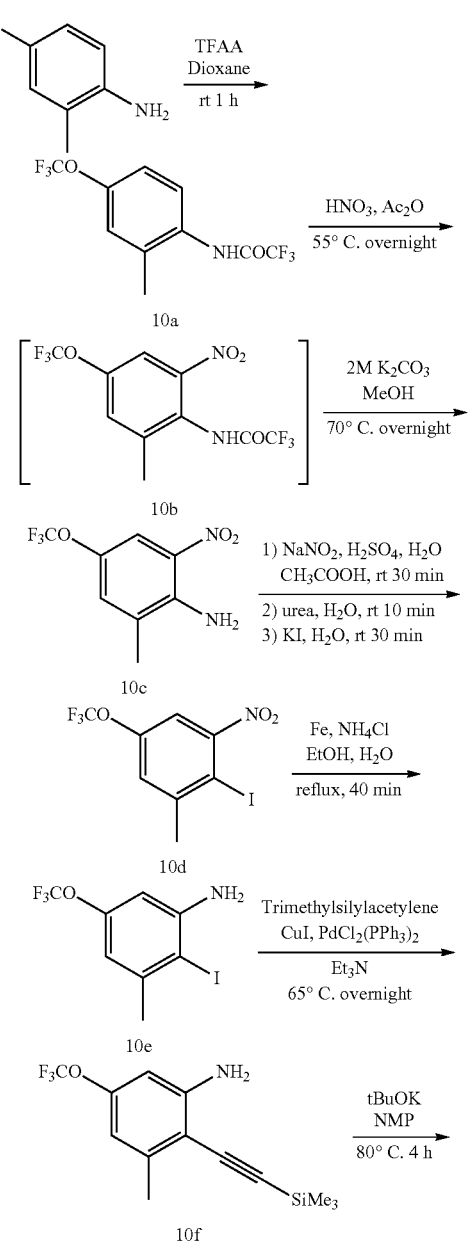

-continued

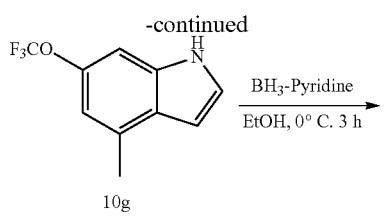

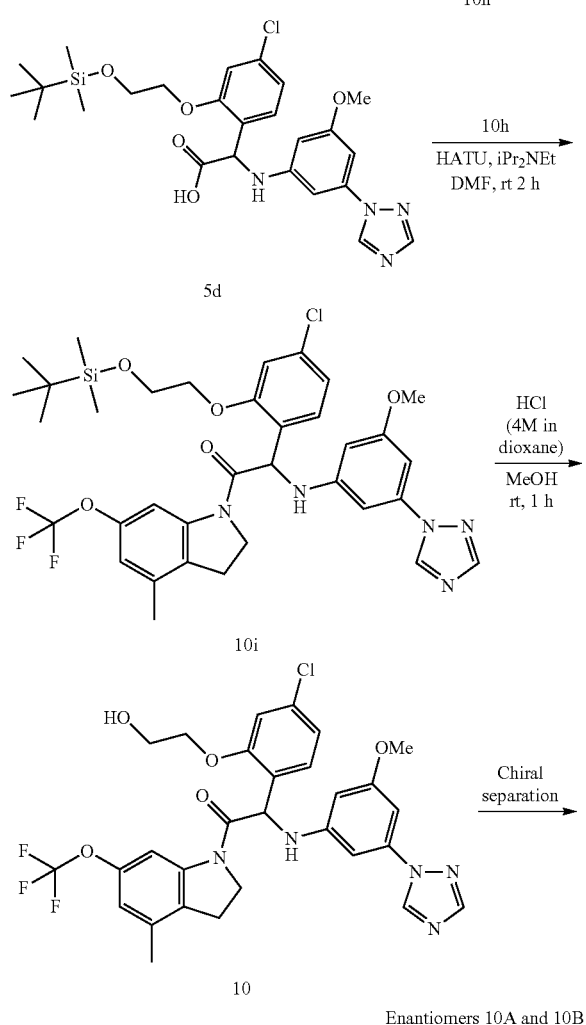

Enantiomers 10A and 10B

Synthesis of Intermediate 10a

To a solution of 2-methyl-4-(trifluoromethoxy)aniline [CAS 86256-59-9] (10.0 g, 52.3 mmol) in dioxane (20 mL) was added trifluoroacetic anhydride (8 mL, 57.2 mmol). The reaction mixture was stirred at room temperature for 1 h. The reaction mixture was concentrated under reduced pressure. The residue was partitioned between EtOAc and 1N HCl. The phases were separated. The organic phase was washed with a saturated solution of $NaHCO_3$ in water, $H_2O$ and brine, dried over $Na_2SO_4$, filtered and concentrated under reduced pressure to afford 14.7 g of 2,2,2-trifluoro-N-(2-methyl-4-(trifluoromethoxy)phenyl)acetamide 10a as a white powder. The compound was used in the next step without further purification.

Synthesis of Intermediate 10c

To acetic anhydride (11.4 mL, 61.1 mmol), cooled at 0° C. was added dropwise 70% nitric acid (3.9 mL). 2,2,2-Trifluoro-N-(2-methyl-4-(trifluoromethoxy)phenyl)-acetamide 10a (5 g, 17.4 mmol) was added portionwise and the reaction mixture was heated at 55° C. for 12 h. After cooling to room temperature, the reaction mixture was diluted with EtOAc and washed with $H_2O$. The organic phase was washed with brine, dried over $Na_2SO_4$, filtered and concentrated under reduced pressure. The residue was dissolved in methanol (46 mL). 2M $K_2CO_3$ (23 mL, 46 mmol) was added and the reaction mixture was heated at 70° C. for 4 h. More 2M $K_2CO_3$ (10 mL, 20 mmol) was added and the reaction mixture was heated at 70° C. for 12 h. The reaction mixture was partially concentrated under reduced pressure to remove methanol. The residue was extracted with EtOAc. The organic phase was washed with $H_2O$ and brine, dried over $Na_2SO_4$, filtered and concentrated under reduced pressure. The residue was purified by flash chromatography on silica gel using a gradient of EtOAc (20% to 50%) in heptane to afford 3.6 g of 2-methyl-6-nitro-4-(trifluoromethoxy)aniline 10c as a yellow solid.

Synthesis of Intermediate 10d

To a solution of 2-methyl-6-nitro-4-(trifluoromethoxy)aniline 10c (1.8 g, 7.69 mmol) in acetic acid (10.9 mL) was added dropwise a solution of sodium nitrite (0.806 g, 11.7 mmol) in $H_2SO_4/H_2O$ (2 mL, 1/1). The reaction mixture was stirred at room temperature for 30 min. $H_2O$ (22 mL) and urea (0.802 g, 13.4 mmol) were added. After 10 min at room temperature, a solution of potassium iodide (1.7 g, 10.2 mmol) in $H_2O$ (11 mL) was added dropwise. The reaction mixture was stirred at room temperature for 30 min. The yellow solid was filtered off, washed with $H_2O$ and dried to give 2.4 g of 2-iodo-1-methyl-3-nitro-5-(trifluoromethoxy)benzene 10d.

Synthesis of Intermediate 10e

To a solution of 2-iodo-1-methyl-3-nitro-5-(trifluoromethoxy)benzene 10d (3.5 g, 10.0 mmol) in EtOH (30 mL) was added a solution of $NH_4Cl$ (2.7 g, 49.9 mmol) in $H_2O$ (30 mL). The reaction mixture was heated at 50° C. Iron (2.6 g, 46.9 mmol) was added and the reaction mixture was heated under reflux for 40 min. After cooling to room temperature, the reaction mixture was filtered through Celite®. The solids were washed with EtOH. The filtrate was partially concentrated under reduced pressure to remove EtOH. The residue was partitioned between EtOAc and a saturated solution of $NaHCO_3$ in water. The phases were separated. The organic phase was washed with $H_2O$ and brine, dried over $Na_2SO_4$, filtered and concentrated under reduced pressure. The residue was purified by flash chromatography on silica gel using a gradient of EtOAc (0% to 25%) in heptane to afford 2.9 g of 2-iodo-3-methyl-5-(trifluoromethoxy)aniline 10e as a yellow oil.

Synthesis of Intermediate 10f

A solution of 2-iodo-3-methyl-5-(trifluoromethoxy)aniline 10e (2.9 g, 9.1 mmol) in triethylamine (23 mL) was degassed with argon for 15 min. Dichlorobis(triphenylphosphine)palladium(II) (0.327 g, 0.47 mmol), copper(I) iodide (0.164 g, 0.86 mmol) and trimethylsilylacetylene (1.8 mL, 13.1 mmol) were added. The reaction mixture was heated at 65° C. for 12 h. After cooling to room temperature, the reaction mixture was diluted with $H_2O$ and extracted with EtOAc (3×). The organic phases were combined, washed with $H_2O$ and brine, dried over $Na_2SO_4$, filtered and concentrated under reduced pressure. The residue was purified by flash chromatography on silica gel using a gradient of EtOAc (0% to 20%) in heptane to afford 2.6 g of 3-methyl-5-(trifluoromethoxy)-2-((trimethylsilyl)ethynyl)aniline 10f as an orange oil.

Synthesis of Intermediate 10g

To a solution of 3-methyl-5-(trifluoromethoxy)-2-((trimethylsilyl)ethynyl)aniline 10f (2.7 g, 9.3 mmol) in NMP (27 mL) was added tBuOK (3.1 g, 27.8 mmol). The reaction mixture was heated at 80° C. for 4 h. After cooling to room temperature, the reaction mixture was diluted with $H_2O$ and extracted with EtOAc (2×). The organic phases were combined, washed with $H_2O$ and brine, dried over $Na_2SO_4$, filtered and concentrated under reduced pressure. The residue was purified by flash chromatography on silica gel using a gradient of EtOAc (0% to 20%) in heptane to afford 1.7 g of 4-methyl-6-(trifluoromethoxy)-1H-indole 10g as an orange oil.

Synthesis of Intermediate 10h

At 0° C., $BH_3$-Pyridine (1.2 mL, 11.6 mmol) was added dropwise to a solution of 4-methyl-6-(trifluoromethoxy)-1H-indole 10g (0.5 g, 2.32 mmol) in EtOH (3 mL). 6N HCl (6 mL) was slowly added dropwise while maintaining the reaction temperature below 10° C. The mixture was stirred at 0° C. for 3 h. Water (12 mL) was added and the mixture was basified until pH 8-9 with a concentrated solution of NaOH in water (the reaction temperature was kept below 20° C.). The mixture was extracted with EtOAc. The organic layer was washed with water, dried over $MgSO_4$, filtered and the solvent was evaporated under reduced pressure. Toluene was added and the solution was concentrated under reduced pressure to give 450 mg of 4-methyl-6-(trifluoromethoxy)indoline 10h.

Synthesis of Intermediate 10i

A mixture of 4-methyl-6-(trifluoromethoxy)indoline 10h (163 mg, 0.75 mmol), 2-(2-(2-((tert-butyldimethylsilyl)oxy)ethoxy)-4-chlorophenyl)-2-((3-methoxy-5-(1H-1,2,4-triazol-1-yl)phenyl)amino)acetic acid 5d (400 mg, 0.75 mmol), HATU (428 mg, 1.13 mmol) and diisopropylethylamine (372 µL, 2.25 mmol) in DMF (3.8 mL) was stirred at room temperature for 2 h. The mixture was diluted with water. The resulting gummy material was taken up with EtOAc. The organic layer was washed with a solution of $K_2CO_3$ 10% in water, water, dried over $MgSO_4$, filtered and the solvent was concentrated under reduced pressure. The compound was purified by flash chromatography on silica gel (15-40 µm, 24 g, heptane/EtOAc gradient 80/20 to 70/30). The pure fractions were combined and the solvent was concentrated under reduced pressure to give 2-(2-(2-((tert-butyldimethylsilyl)oxy)ethoxy)-4-chlorophenyl)-2-((3-methoxy-5-(1H-1,2,4-triazol-1-yl)phenyl)amino)-1-(4-methyl-6-(trifluoromethoxy)indolin-1-yl)ethanone 10i (226 mg).

Synthesis of Compound 10 and Chiral Separation into Enantiomers 10A and 10B

Under a $N_2$ flow, at 5° C., 4M HCl in dioxane (772 µL, 3.1 mmol) was added dropwise to a solution of 2-(2-(2-((tert-butyldimethylsilyl)oxy)ethoxy)-4-chlorophenyl)-2-((3-methoxy-5-(1H-1,2,4-triazol-1-yl)phenyl)amino)-1-(4-methyl-6-(trifluoromethoxy)indolin-1-yl)ethanone 10i (226 mg, 0.31 mmol) in MeOH (4 mL). The reaction was stirred at room temperature for 1 h. The mixture was cooled to 0° C., basified with a 10% aqueous solution of $K_2CO_3$ and extracted with EtOAc. The organic layer was separated, washed with water, dried over $MgSO_4$, filtered and the solvent was concentrated under reduced pressure. The residue was purified by flash chromatography on silica gel (15-40 µm, 12 g, $CH_2Cl_2$/MeOH 98.5/1.5). A second purification was performed via reverse phase chromatography (Stationary phase: YMC-actus Triart-C18 10 µm 30×150 mm, Mobile phase: Gradient from 55% $NH_4HCO_3$ 0.2%, 45% $CH_3CN$ to 0% $NH_4HCO_3$ 0.2%, 100% $CH_3CN$). The pure fractions were combined and the solvent was concentrated under reduced pressure to give 2-(4-chloro-2-(2-hydroxyethoxy)phenyl)-2-((3-methoxy-5-(1H-1,2,4-triazol-1-yl)phenyl)amino)-1-(4-methyl-6-(trifluoromethoxy) indolin-1-yl)ethanone 10 (78 mg) as a racemate. A small fraction was solidified by trituration with $CH_3CN$/diisopropyl ether to provide Compound 10 (9 mg). The remaining amount was used to separate the Enantiomers of Compound 10 via Preparative Chiral SFC (Stationary phase: Chiralpak® AD-H 5 µm 250×30 mm, Mobile phase: 60% $CO_2$, 40% iPrOH). The first eluted enantiomer (27 mg) was dissolved in $CH_3CN$ (2 ml), water (8 mL) was added and the mixture was lyophilized to give Enantiomer 10A (25 mg) as a powder. The second eluted enantiomer (28 mg) was dissolved in $CH_3CN$ (2 ml), water (8 mL) was added and the mixture was lyophilized to give Enantiomer 10B (22 mg) as a powder.

Compound 10:

$^1$H NMR (500 MHz, DMSO-$d_6$) δ ppm 2.21 (s, 3H) 3.01-3.13 (m, 2H) 3.72 (s, 3H) 3.70-3.82 (m, 2H) 4.08-4.22 (m, 3H) 4.40-4.48 (m, 1H) 4.98 (t, J=5.4 Hz, 1H) 5.82 (d, J=8.5 Hz, 1H) 6.35 (br s, 1H) 6.66 (s, 1H) 6.82-6.90 (m, 3H) 7.02 (dd, J=8.4, 1.7 Hz, 1H) 7.15 (d, J=1.6 Hz, 1H) 7.36 (d, J=8.2 Hz, 1H) 7.89 (s, 1H) 8.16 (s, 1H) 9.13 (s, 1H)

LC/MS (method LC-B): $R_t$ 3.26 min, MH$^+$ 618

Enantiomer 10A:

$^1$H NMR (500 MHz, DMSO-$d_6$) δ ppm 2.21 (s, 3H) 3.01-3.14 (m, 2H) 3.72 (s, 3H) 3.71-3.83 (m, 2H) 4.07-4.22 (m, 3H) 4.44 (td, J=10.2, 6.5 Hz, 1H) 4.98 (t, J=5.5 Hz, 1H) 5.82 (d, J=8.5 Hz, 1H) 6.35 (s, 1H) 6.66 (t, J=1.9 Hz, 1H) 6.81-6.90 (m, 3H) 7.02 (dd, J=8.4, 2.1 Hz, 1H) 7.15 (d, J=1.9 Hz, 1H) 7.36 (d, J=8.2 Hz, 1H) 7.89 (s, 1H) 8.16 (s, 1H) 9.13 (s, 1H)

LC/MS (method LC-B): $R_t$ 3.26 min, MH$^+$ 618

$[α]_D^{20}$: −38.4° (c 0.279, DMF)

Chiral SFC (method SFC-F): $R_t$ 1.41 min, MH$^+$ 618, chiral purity 100%.

Enantiomer 10B:

$^1$H NMR (500 MHz, DMSO-$d_6$) δ ppm 2.21 (s, 3H) 3.00-3.14 (m, 2H) 3.72 (s, 3H) 3.71-3.82 (m, 2H) 4.06-4.23 (m, 3H) 4.44 (td, J=10.1, 6.9 Hz, 1H) 4.95-5.02 (m, 1H) 5.82 (d, J=8.5 Hz, 1H) 6.35 (s, 1H) 6.66 (t, J=1.7 Hz, 1H) 6.82-6.90 (m, 3H) 7.02 (dd, J=8.5, 1.9 Hz, 1H) 7.15 (d, J=1.9 Hz, 1H) 7.36 (d, J=8.2 Hz, 1H) 7.89 (s, 1H) 8.16 (s, 1H) 9.13 (s, 1H)

LC/MS (method LC-B): $R_t$ 3.26 min, MH$^+$ 618

$[α]_D^{20}$: −37.5° (c 0.299, DMF)

Chiral SFC (method SFC-F): $R_t$ 1.82 min, MH$^+$ 618, chiral purity 100%.
Example 11: Synthesis of 4-(5-chloro-2-(1-((3-methoxy-5-(1H-1,2,4-triazol-1-yl)phenyl)amino)-2-oxo-2-(6-(trifluoromethyl)indolin-1-yl)ethyl)phenoxy)butanoic acid (Compound 11) and Chiral Separation into Enantiomers 11A and 11B
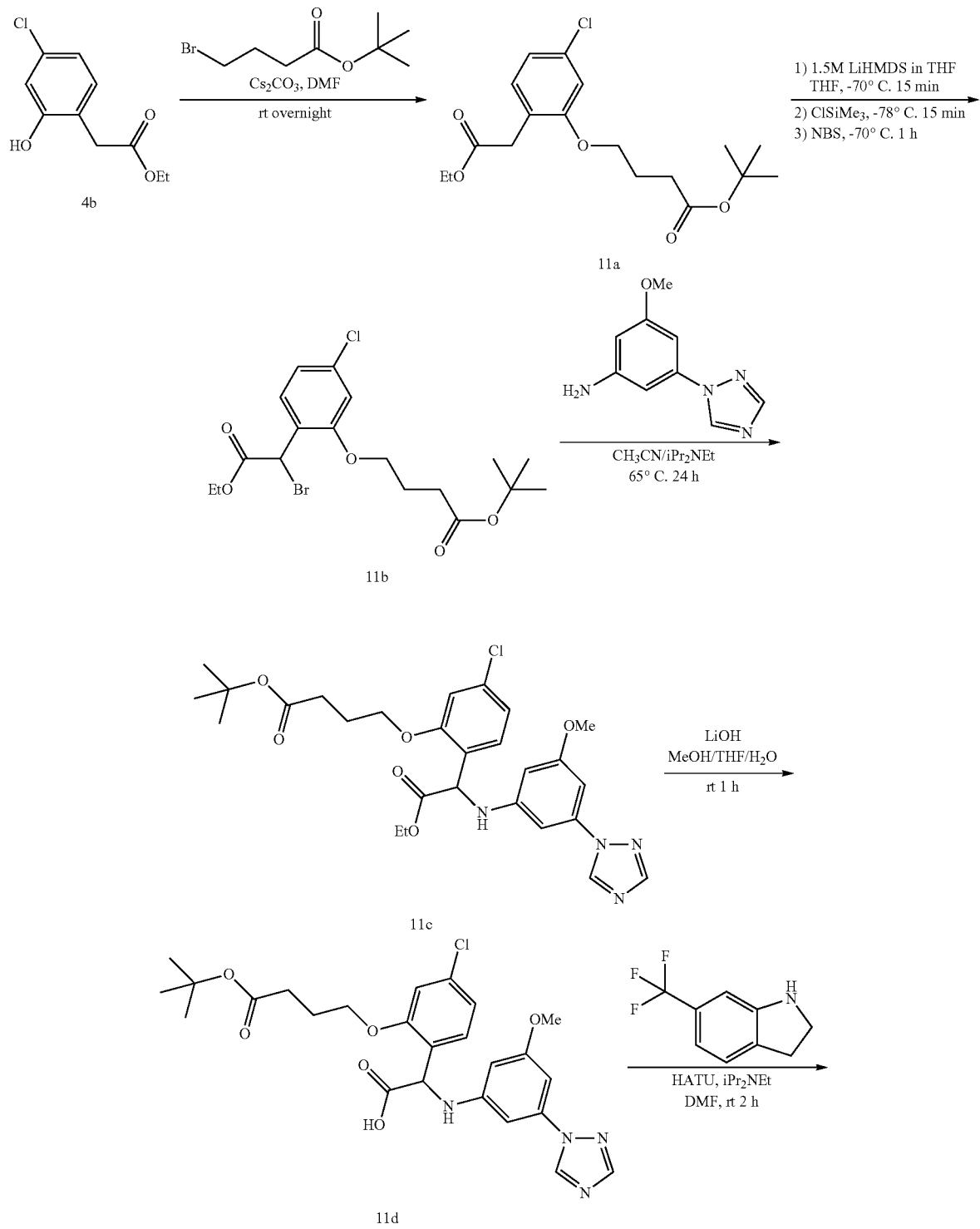

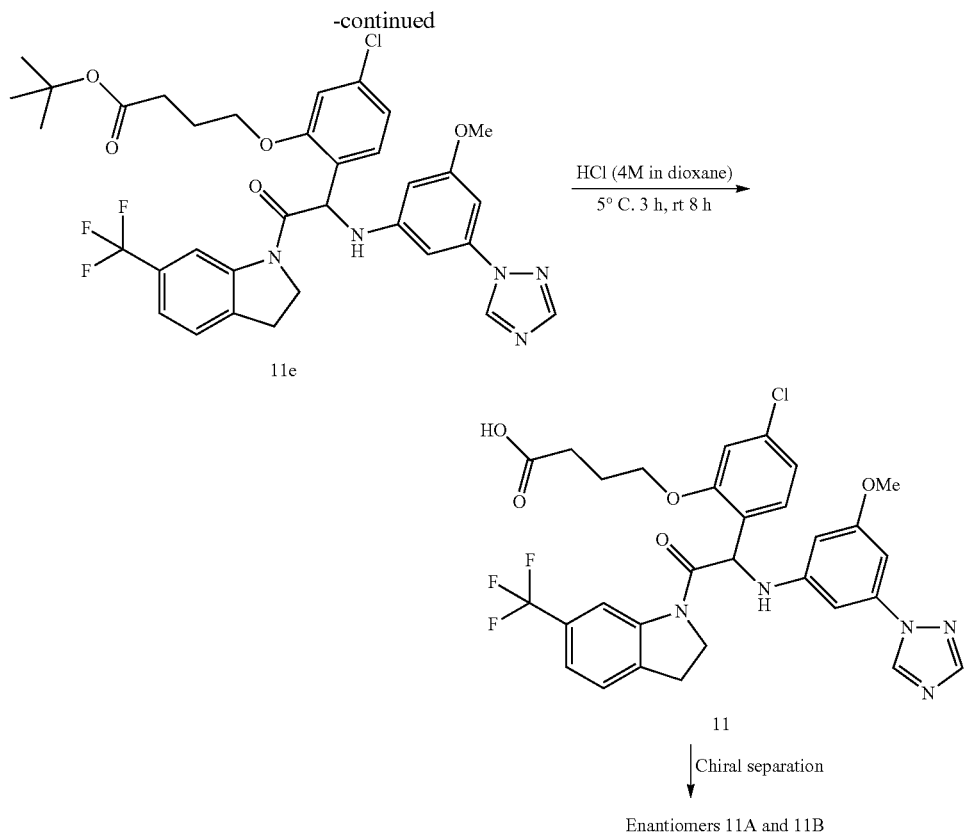

Synthesis of Intermediate 11a

To a suspension of ethyl 2-(4-chloro-2-hydroxyphenyl)acetate 4b (8.5 g, 39.6 mmol) and Cs$_2$CO$_3$ (25.8 g, 79.2 mmol) in DMF (130 mL) at 10° C. was added dropwise tert-butyl 4-bromobutanoate [CAS 110611-91-1] (7 mL, 39.6 mmol). The mixture was stirred at room temperature overnight. The mixture was diluted with EtOAc and water. The layers were decanted. The organic layer was washed with water, dried over MgSO$_4$, filtered and the solvent was concentrated under reduced pressure. The residue was purified by flash chromatography on silica gel (15-40 µm, 120 g, heptane/EtOAc 90/10). The pure fractions were combined and concentrated to dryness to give tert-butyl 4-(5-chloro-2-(2-ethoxy-2-oxoethyl)phenoxy)butanoate 11a (12.7 g).

Synthesis of Intermediate 11b

A flask was charged with LiHMDS 1.5 M in THF (23.5 mL, 35.3 mmol) under a N$_2$ flow and the solution was cooled to −78° C. A solution of tert-butyl 4-(5-chloro-2-(2-ethoxy-2-oxoethyl)phenoxy)butanoate 11a (6.3 g, 17.6 mmol) in THF (60 mL) was added dropwise and the mixture was stirred at −78° C. for 15 min. Chlorotrimethylsilane (3.6 mL, 28.3 mmol) was added. After 15 min at −78° C., N-Bromosuccinimide (3.77 g, 21.2 mmol) in THF (40 mL) was added and the mixture was stirred at −70° C. for 1 h. The reaction was quenched with water and extracted with EtOAc. The organic layer was separated, washed with water, dried over MgSO$_4$, filtered and the solvent was concentrated under reduced pressure to yield tert-butyl 4-(2-(1-bromo-2-ethoxy-2-oxoethyl)-5-chlorophenoxy)butanoate 11b (7.6 g). The compound was used directly in the next reaction step without further purification.

Synthesis of Intermediate 11c

To a solution of tert-butyl 4-(2-(1-bromo-2-ethoxy-2-oxoethyl)-5-chlorophenoxy)butanoate 11b (7.6 g, 17.4 mmol) in CH$_3$CN (140 mL) at room temperature, was added diisopropylethylamine (4.8 mL, 27.9 mmol) and 3-methoxy-5-(1H-1,2,4-triazol-1-yl)aniline [CAS 1220630-56-7] (4 g, 20.9 mmol). The mixture was stirred at 65° C. for 24 h. The mixture was diluted with EtOAc, washed with 0.5N HCl (twice) and water. The organic layer was dried over MgSO$_4$, filtered and the solvent was concentrated under reduced pressure. The residue was purified by flash chromatography on silica gel (15-40 µm, 120 g, heptane/EtOAc 85/15 to 70/30). The pure fractions were combined and concentrated to dryness to give tert-butyl 4-(5-chloro-2-(2-ethoxy-1-((3-methoxy-5-(1H-1,2,4-triazol-1-yl)phenyl)amino)-2-oxoethyl)phenoxy)butanoate 11c (6.6 g).

Synthesis of Intermediate 11d

A mixture of tert-butyl 4-(5-chloro-2-(2-ethoxy-1-((3-methoxy-5-(1H-1,2,4-triazol-1-yl)phenyl)amino)-2-oxoethyl)phenoxy)butanoate 11c (6.6 g, 12.1 mmol) and lithium hydroxide monohydrate (1.52 g, 36.3 mmol) in THF/water (1/1) (160 mL) was stirred at room temperature for 1 h. The mixture was diluted with water. The aqueous solution was slowly acidified with 3N HCl and extracted with EtOAc. The combined organic layers were dried over MgSO$_4$, filtered and the solvent was concentrated under reduced pressure to give 2-(2-(4-(tert-butoxy)-4-oxobutoxy)-4-chlorophenyl)-2-((3-methoxy-5-(1H-1,2,4-triazol-1-yl)phenyl)amino)acetic acid 11d (6.2 g). The crude product was used without further purification in the next step.

Synthesis of Intermediate 11e

A mixture of 6-(trifluoromethyl)indoline [CAS 181513-29-1] (290 mg, 1.55 mmol), 2-(2-(4-(tert-butoxy)-4-oxobutoxy)-4-chlorophenyl)-2-((3-methoxy-5-(1H-1,2,4-triazol-1-yl)phenyl)amino)acetic acid 11d (800 mg, 1.55 mmol), HATU (880 mg, 2.32 mmol) and diisopropylethylamine (770 µL, 4.64 mmol) in DMF (30 mL) was stirred at room temperature for 2 h. The mixture was diluted with water. The precipitate was filtered off, washed with water and taken up with EtOAc. The organic layer was washed with water, dried over $MgSO_4$, filtered and the solvent was concentrated under reduced pressure. The residue was crystallized from diisopropyl ether to give tert-butyl 4-(5-chloro-2-(1-((3-methoxy-5-(1H-1,2,4-triazol-1-yl)phenyl)amino)-2-oxo-2-(6-(trifluoromethyl)indolin-1-yl)ethyl)phenoxy)butanoate 11e (500 mg).

Synthesis of Compound 11 and Chiral Separation into Enantiomers 11A and 11B

A solution of tert-butyl 4-(5-chloro-2-(1-((3-methoxy-5-(1H-1,2,4-triazol-1-yl)phenyl)amino)-2-oxo-2-(6-(trifluoromethyl)indolin-1-yl)ethyl)phenoxy)butanoate 11e (500 mg, 0.729 mmol) in 4M HCl in dioxane (5 mL) was stirred at 5° C. for 3 h and at room temperature for 8 h. The precipitate was filtered off, washed with dioxane/diisopropyl ether and dried to give 4-(5-chloro-2-(1-((3-methoxy-5-(1H-1,2,4-triazol-1-yl)phenyl)amino)-2-oxo-2-(6-(trifluoromethyl)indolin-1-yl)ethyl)phenoxy)butanoic acid 11 (430 mg, 0.4 $H_2O$ (determined by titration)) as a racemate.

The eEnantiomers of Compound 11 were separated via Preparative Chiral SFC (Stationary phase: Chiralpak® AD-H 5 µm 250×30 mm, Mobile phase: 65% $CO_2$, 35% EtOH). The first eluted enantiomer (80 mg) was solidified by titration with petroleum ether/diisopropyl ether to give Enantiomer 11A (65 mg). The second eluted enantiomer (126 mg) was solidified by titration with petroleum ether/diisopropyl ether to give Enantiomer 11B (110 mg).
Compound 11:
$^1$H NMR (400 MHz, DMSO-$d_6$) δ ppm 1.94-2.02 (m, 2H) 2.31-2.42 (m, 2H) 3.15-3.35 (m, 2H) 3.73 (s, 3H) 4.01-4.24 (m, 3H) 4.22-4.49 (m, 1H) 5.73 (s, 1H) 6.34 (s, 1H) 6.67 (s, 1H) 6.82 (s, 1H) 7.02 (dd, J=8.1, 2.0 Hz, 1H) 7.13 (d, J=2.0 Hz, 1H) 7.33 (d, J=8.0 Hz, 1H) 7.38 (d, J=7.6 Hz, 1H) 7.45 (d, J=7.6 Hz, 1H) 8.16 (s, 1H) 8.38 (s, 1H) 9.15 (s, 1H)
LC/MS (method LC-A): $R_t$ 2.70 min, MH$^+$ 630
Enantiomer 11A:
$^1$H NMR (500 MHz, DMSO-$d_6$) δ ppm 1.98 (br s, 2H) 2.28-2.45 (m, 2H) 3.13-3.29 (m, 2H) 3.74 (s, 3H) 4.02-4.17 (m, 3H) 4.36-4.44 (m, 1H) 5.74 (br d, J=8.5 Hz, 1H) 6.35 (br s, 1H) 6.68 (s, 1H) 6.80-6.88 (m, 2H) 7.03 (br d, J=7.9 Hz, 1H) 7.14 (s, 1H) 7.33 (d, J=7.8 Hz, 1H) 7.37-7.40 (m, 1H) 7.46 (br d, J=7.6 Hz, 1H) 8.16 (s, 1H) 8.39 (s, 1H) 9.16 (s, 1H) 12.13 (br s, 1H)
LC/MS (method LC-A): $R_t$ 2.79 min, MH$^+$ 630
$[α]_D^{20}$: −28.9° (c 0.26, DMF)
Chiral SFC (method SFC-G): $R_t$ 3.31 min, MH$^+$ 630, chiral purity 100%.
Enantiomer 11B:
$^1$H NMR (500 MHz, DMSO-$d_6$) δ ppm 1.91-2.04 (m, 2H) 2.28-2.46 (m, 2H) 3.16-3.30 (m, 2H) 3.73 (s, 3H) 4.02-4.18 (m, 3H) 4.35-4.44 (m, 1H) 5.73 (br d, J=8.5 Hz, 1H) 6.34 (br s, 1H) 6.68 (s, 1H) 6.80-6.87 (m, 2H) 7.02 (br d, J=7.9 Hz, 1H) 7.13 (s, 1H) 7.31-7.41 (m, 2H) 7.45 (br d, J=7.9 Hz, 1H) 8.16 (s, 1H) 8.38 (s, 1H) 9.16 (s, 1H) 12.13 (br s, 1H)
LC/MS (method LC-A): $R_t$ 2.79 min, MH$^+$ 630
$[α]_D^{20}$: +23.8° (c 0.29, DMF)
Chiral SFC (method SFC-G): $R_t$ 4.32 min, MH$^+$ 630, chiral purity 100%.

Example 12: Synthesis of 4-(5-chloro-2-(1-((3-methoxy-5-(1H-1,2,4-triazol-1-yl)phenyl)amino)-2-(5-methoxy-6-(trifluoromethyl)indolin-1-yl)-2-oxoethyl)phenoxy)butanoic acid (Compound 12) and Chiral Separation into Enantiomers 12A and 12B

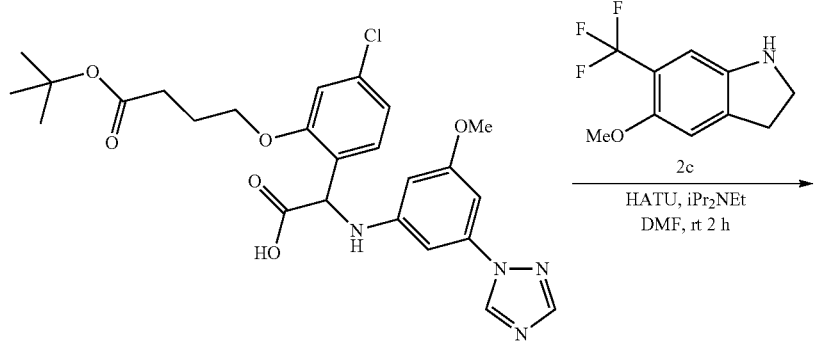

11d

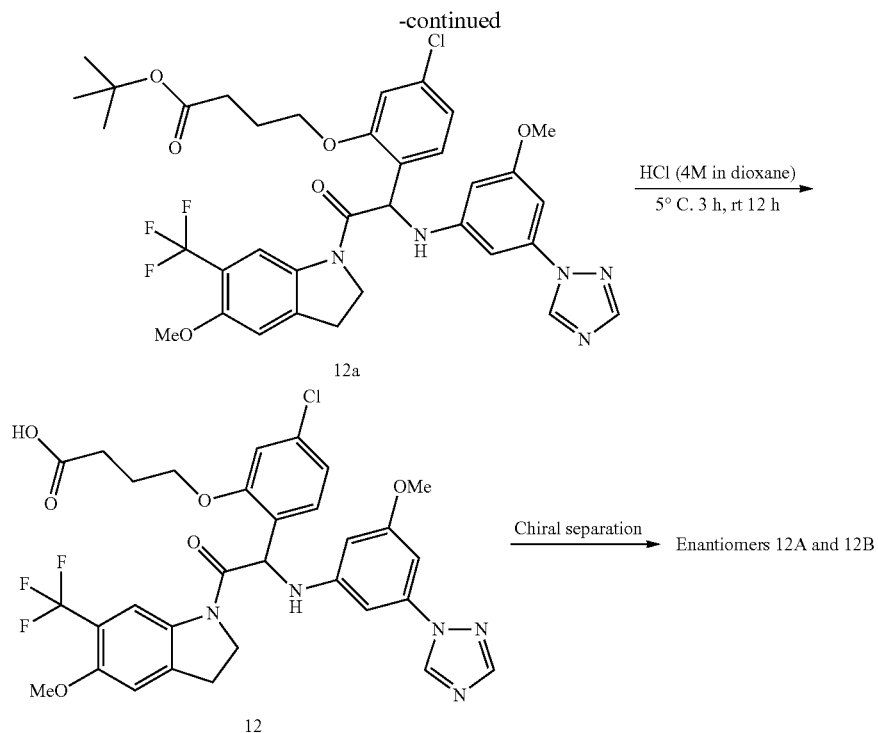

Synthesis of Intermediate 12a

A mixture of 5-methoxy-6-(trifluoromethyl)indoline 2c (630 mg, 2.9 mmol), 2-(2-(4-(tert-butoxy)-4-oxobutoxy)-4-chlorophenyl)-2-((3-methoxy-5-(1H-1,2,4-triazol-1-yl)phenyl)amino)acetic acid 11d (1.5 g, 2.9 mmol), HATU (1.65 g, 4.35 mmol) and diisopropylethylamine (1.45 mL, 8.7 mmol) in DMF (30 mL) was stirred at room temperature for 2 h. The mixture was diluted with water. The precipitate was filtered off, washed with water and taken up with EtOAc. The organic solution was washed with water, dried over $MgSO_4$, filtered and the solvent was concentrated under reduced pressure. The residue was purified by flash chromatography on silica gel (15-40 µm, 120 g, heptane/EtOAc 60/40). The pure fractions were combined and concentrated to dryness to give, after crystallization from ether/diisopropyl ether, tert-butyl 4-(5-chloro-2-(1-(((3-methoxy-5-(1H-1,2,4-triazol-1-yl)phenyl)amino)-2-(5-methoxy-6-(trifluoromethyl)indolin-1-yl)-2-oxoethyl)phenoxy)butanoate 12a (1.45 g).

Synthesis of Compound 12 and Chiral Separation into Enantiomers 12A and 12B

A solution of tert-butyl 4-(5-chloro-2-(1-((3-methoxy-5-(1H-1,2,4-triazol-1-yl)phenyl)amino)-2-(5-methoxy-6-(trifluoromethyl)indolin-1-yl)-2-oxoethyl)phenoxy)butanoate 12a (1.45 g, 2.03 mmol) in 4M HCl in dioxane (12 mL) was stirred at 5° C. for 3 h and at room temperature for 12 h. The precipitate was filtered off, washed with dioxane/diisopropyl ether and dried to provide crude Compound 12 (1.02 g). A small part (90 mg) was further purified by achiral SFC (Stationary phase: 2-Ethylpyridine 6 µm 150×21.2 mm, Mobile phase: 60% $CO_2$, 40% iPrOH) to give, after solidification by trituration with $CH_3CN$/diisopropyl ether, 4-(5-chloro-2-(1-((3-methoxy-5-(1H-1,2,4-triazol-1-yl)phenyl) amino)-2-(5-methoxy-6-(trifluoromethyl)indolin-1-yl)-2-oxoethyl)phenoxy)butanoic acid 12 (70 mg) as a racemate. The remaining amount was used to separate the enantiomers.

The enantiomers of Compound 12 were separated via Preparative Chiral SFC (Stationary phase: Chiralpak® AS-H 5 µm 250×20 mm, Mobile phase: 63% $CO_2$, 37% iPrOH). The first eluted enantiomer (458 mg) was stirred in a mixture of 1N HCl and EtOAc. The organic layer was separated, dried over $MgSO_4$, filtered and the solvent was concentrated under reduced pressure. The residue was solidified by trituration with diisopropyl ether/petroleum ether to give Enantiomer 12A (270 mg). The second eluted enantiomer (405 mg) was stirred in a mixture of 1N HCl and EtOAc. The organic layer was separated, dried over $MgSO_4$, filtered and the solvent was concentrated under reduced pressure. The residue was solidified by trituration with diisopropyl ether/petroleum ether to give Enantiomer 12B (272 mg).

Compound 12:

$^1$H NMR (400 MHz, DMSO-$d_6$) δ ppm 1.95-2.04 (m, 2H) 2.31-2.45 (m, 2H) 3.15-3.28 (m, 2H) 3.73 (s, 3H) 3.84 (s, 3H) 3.98-4.17 (m, 3H) 4.33-4.41 (m, 1H) 5.70 (br d, J=8.6 Hz, 1H) 6.33 (s, 1H) 6.66 (s, 1H) 6.77-6.83 (m, 2H) 7.01 (br d, J=8.6 Hz, 1H) 7.12 (s, 1H) 7.23 (s, 1H) 7.33 (d, J=8.6 Hz, 1H) 8.15 (s, 1H) 8.34 (s, 1H) 9.13 (s, 1H) 12.07 (br s, 1H)

LC/MS (method LC-A): $R_t$ 2.72 min, MH$^+$ 660

Enantiomer 12A:

$^1$H NMR (500 MHz, DMSO-$d_6$) δ ppm 1.94-2.05 (m, 2H) 2.31-2.46 (m, 2H) 3.16-3.31 (m, 2H) 3.73 (s, 3H) 3.85 (s, 3H) 3.99-4.18 (m, 3H) 4.38 (td, J=10.2, 6.5 Hz, 1H) 5.71 (d, J=8.5 Hz, 1H) 6.34 (s, 1H) 6.67 (s, 1H) 6.82 (s, 1H) 6.83 (d, J=9.5 Hz, 1H) 7.02 (dd, J=8.2, 1.6 Hz, 1H) 7.13 (s, 1H) 7.23 (s, 1H) 7.33 (d, J=8.2 Hz, 1H) 8.16 (s, 1H) 8.34 (s, 1H) 9.15 (s, 1H) 12.11 (br s, 1H)

LC/MS (method LC-A): $R_t$ 2.70 min, MH⁺ 660
$[\alpha]_D^{20}$: +30.4° (c 0.257, DMF)
Chiral SFC (method SFC-H): $R_t$ 3.71 min, MH⁺ 660, chiral purity 100%.
Enantiomer 12B:
¹H NMR (500 MHz, DMSO-d₆) δ ppm 1.91-2.08 (m, 2H) 2.32-2.44 (m, 2H) 3.16-3.31 (m, 2H) 3.73 (s, 3H) 3.85 (s, 3H) 3.99-4.17 (m, 3H) 4.38 (td, J=10.3, 6.6 Hz, 1H) 5.71 (d, J=8.5 Hz, 1H) 6.34 (s, 1H) 6.67 (s, 1H) 6.79-6.85 (m, 2H) 7.02 (d, J=8.1 Hz, 1H) 7.13 (s, 1H) 7.23 (s, 1H) 7.33 (d, J=8.2 Hz, 1H) 8.16 (s, 1H) 8.34 (s, 1H) 9.15 (s, 1H) 12.12 (br s, 1H)

LC/MS (method LC-A): $R_t$ 2.70 min, MH⁺ 630
$[\alpha]_D^{20}$: −36.9° (c 0.287, DMF)
Chiral SFC (method SFC-H): $R_t$ 5.91 min, MH⁺ 660, chiral purity 100%.

Example 13: Synthesis of 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)butanoic acid (Compound 13) and Chiral Separation into Enantiomers 13A and 13B

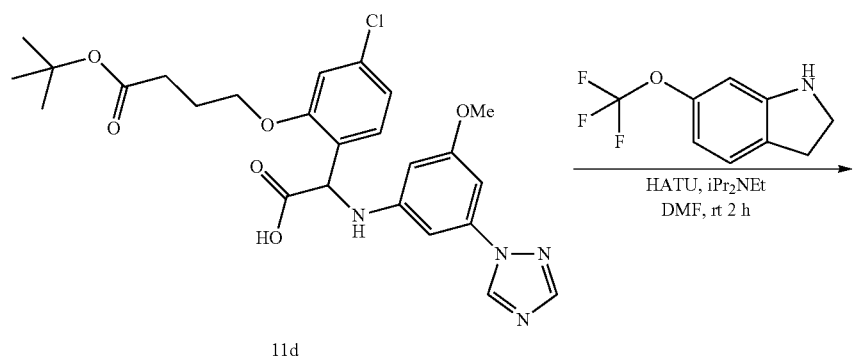

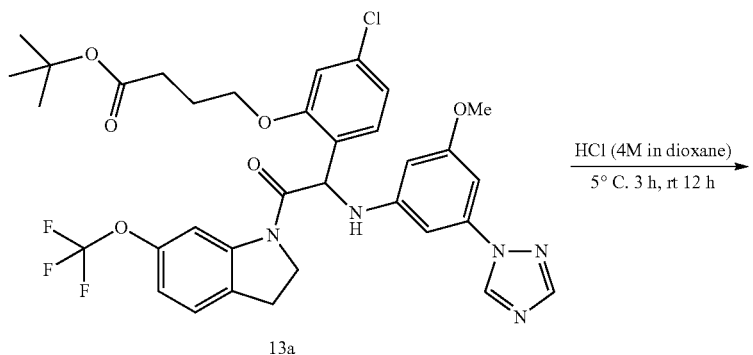

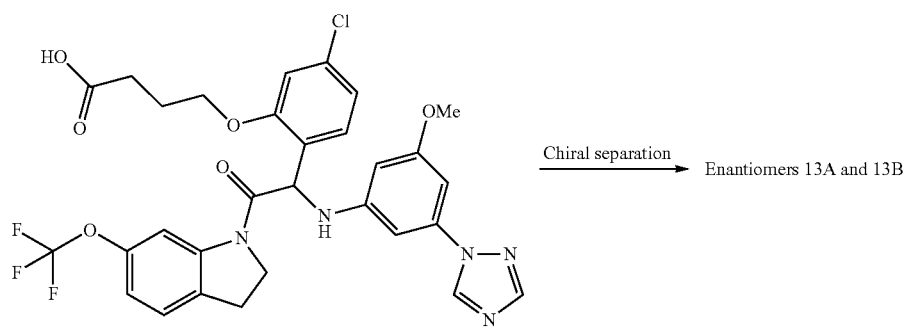

Synthesis of Intermediate 13a

A mixture of 6-(trifluoromethoxy)indoline [CAS 959235-95-1] (590 mg, 2.9 mmol), 2-(2-(4-(tert-butoxy)-4-oxobutoxy)-4-chlorophenyl)-2-((3-methoxy-5-(1H-1,2,4-triazol-1-yl)phenyl)amino)acetic acid 11d (1.5 g, 2.9 mmol), HATU (1.65 g, 4.35 mmol) and diisopropylethylamine (1.45 mL, 8.7 mmol) in DMF (60 mL) was stirred at room temperature for 12 h. The mixture was diluted with water. The precipitate was filtered off, washed with water and taken up with EtOAc. The organic layer was washed with water, dried over MgSO$_4$, filtered and the solvent was concentrated under reduced pressure. The residue was purified by flash chromatography on silica gel (15-40 µm, 120 g, heptane/EtOAc 60/40). The pure fractions were combined and concentrated to dryness to give, after crystallization from ether/diisopropyl ether, tert-butyl 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)-butanoate 13a (1.05 g).

Synthesis of Compound 13 and Chiral Separation into Enantiomers 13A and 13B

A solution of tert-butyl 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)butanoate 13a (1.05 g, 1.50 mmol) in 4M HCl in dioxane (9.5 mL) was stirred at 5° C. for 3 h and at room temperature for 12 h. The precipitate was filtered off, washed with dioxane/diisopropyl ether and dried to give 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)butanoic acid 13 (965 mg, 0.23 H$_2$O (determined by titration)) as a racemate.

The enantiomers of Compound 13 were separated via Preparative Chiral SFC (Stationary phase: Chiralpak® AS-H 5 µm 250×20 mm, Mobile phase: 80% CO$_2$, 20% EtOH). The first eluted enantiomer (390 mg) was solidified by trituration with petroleum ether/diisopropyl ether to give Enantiomer 13A (260 mg). The second eluted enantiomer (350 mg) was solidified by trituration with petroleum ether/diisopropyl ether to give Enantiomer 13B (188 mg).

Compound 13:
$^1$H NMR (500 MHz, DMSO-d$_6$) δ ppm 1.94-2.03 (m, 2H) 2.33-2.41 (m, 2H) 3.10-3.24 (m, 2H) 3.73 (s, 3H) 4.04-4.26 (m, 3H) 4.39 (td, J=10.2, 6.5 Hz, 1H) 5.71 (s, 1H) 6.34 (s, 1H) 6.67 (s, 1H) 6.81 (s, 1H) 6.99-7.07 (m, 2H) 7.13 (d, J=1.6 Hz, 1H) 7.27-7.39 (m, 2H) 8.04 (s, 1H) 8.16 (s, 1H) 9.15 (s, 1H) 12.08 (br s, 1H)
LC/MS (method LC-B): R$_t$ 2.73 min, MH$^+$ 646

Enantiomer 13A:
$^1$H NMR (500 MHz, DMSO-d$_6$) δ ppm 1.93-2.03 (m, 2H) 2.34-2.47 (m, 2H) 3.13-3.21 (m, 2H) 3.73 (s, 3H) 4.03-4.17 (m, 3H) 4.39 (td, J=10.1, 6.6 Hz, 1H) 5.72 (d, J=8.5 Hz, 1H) 6.35 (s, 1H) 6.68 (s, 1H) 6.82 (s, 1H) 6.87 (d, J=8.2 Hz, 1H) 7.02 (t, J=8.4 Hz, 1H) 7.13 (s, 1H) 7.27-7.39 (m, 2H) 8.04 (s, 1H) 8.16 (s, 1H) 9.15 (s, 1H) 12.10 (br s, 1H)
LC/MS (method LC-A): R$_t$ 2.83 min, MH$^+$ 646
[α]$_D^{20}$: +38.4° (c 0.276, DMF)
Chiral SFC (method SFC-I): R$_t$ 4.96 min, MH$^+$ 646, chiral purity 100%.

Enantiomer 13B:
$^1$H NMR (500 MHz, DMSO-d$_6$) δ ppm 1.91-2.02 (m, 2H) 2.33-2.41 (m, 2H) 3.10-3.24 (m, 2H) 3.73 (s, 3H) 4.04-4.17 (m, 3H) 4.39 (td, J=10.1, 6.6 Hz, 1H) 5.72 (d, J=8.5 Hz, 1H) 6.35 (s, 1H) 6.68 (s, 1H) 6.81-6.89 (m, 2H) 6.99-7.05 (m, 2H) 7.12-7.15 (m, 1H) 7.27-7.40 (m, 2H) 8.04 (s, 1H) 8.16 (s, 1H) 9.16 (s, 1H) 12.11 (br s, 1H)
LC/MS (method LC-A): R$_t$ 2.83 min, MH$^+$ 646
[α]$_D^{20}$: −43.2° (c 0.273, DMF)
Chiral SFC (method SFC-I): R$_t$ 6.56 min, MH$^+$ 646, chiral purity 100%.

Example 14: Synthesis of 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)-2,2-dimethylbutanoic acid (Compound 14) and Chiral Separation into Enantiomers 14A and 14B

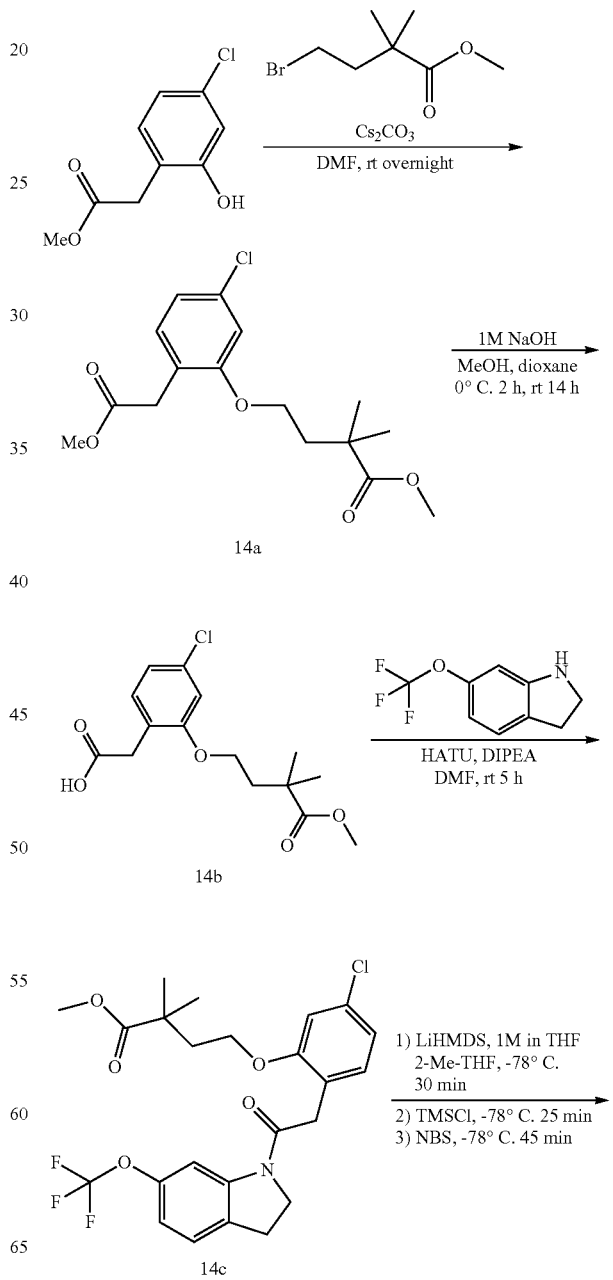

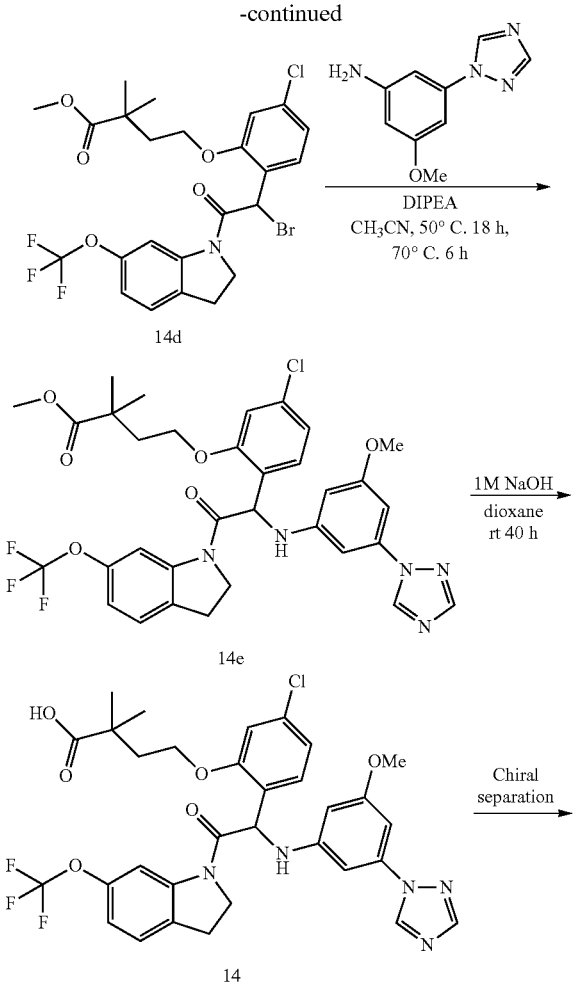

Synthesis of Intermediate 14a

To a mixture of methyl 2-(4-chloro-2-hydroxyphenyl)acetate [CAS 518979-09-4] (1 g, 4.99 mmol) and cesium carbonate (3.25 g, 9.97 mmol) in DMF (30 mL) was added methyl 4-bromo-2,2-dimethylbutanoate [CAS 4833-99-2] (1.09 g, 5.23 mmol). The reaction mixture was stirred at room temperature for 20 h. the reaction mixture was poured out into stirring water (150 mL) and the product was extracted (2×) with Et$_2$O. The combined organic layers were washed with brine, dried over MgSO$_4$, filtered, and evaporated under reduced pressure. The product crystallized upon standing at room temperature. The solid residue was stirred up in 5 mL diisopropyl ether. The precipitate was filtered off, washed (3×) with diisopropyl ether, and dried under vacuum at 45° C. to provide methyl 4-(5-chloro-2-(2-methoxy-2-oxoethyl)phenoxy)-2,2-dimethylbutanoate 14a (0.897 g).

Synthesis of Intermediate 14b

A solution of methyl 4-(5-chloro-2-(2-methoxy-2-oxoethyl)phenoxy)-2,2-dimethylbutanoate 14a (0.897 g, 2.73 mmol) in a solvent mixture of MeOH (10 mL) and dioxane (5 mL) was cooled on an ice-bath. At 0° C., 1M NaOH (2.73 mL, 2.73 mmol) was added carefully. The reaction mixture was stirred at 0° C. for 2 h, and at room temperature for 14 h. The reaction mixture was poured out into water (50 mL), stirred for 15 minutes and left standing for 30 minutes. The solid fraction (unreacted intermediate 14a) was filtered off, and washed (3×) with water. The combined filtrates were acidified by dropwise addition of 1N HCl (2.8 mL) while stirring. After 10 min, the precipitate was filtered off, washed (3×) with water, and dried under vacuum at 45° C. to provide 2-(4-chloro-2-(4-methoxy-3,3-dimethyl-4-oxobutoxy)phenyl)acetic acid 14b (0.576 g).

Synthesis of Intermediate 14c

To a stirring solution of 2-(4-chloro-2-(4-methoxy-3,3-dimethyl-4-oxobutoxy)phenyl)acetic acid 14b (576 mg, 1.83 mmol), 6-(trifluoromethoxy)indoline [CAS 959235-95-1] (409 mg, 2.01 mmol) and diisopropylethylamine (907 µL, 5.49 mmol) in DMF (7.5 mL) under N$_2$-atm was added HATU (1.07 g, 2.75 mmol), and the reaction mixture was stirred at room temperature for 5 h. Water (30 mL) was added, and the product was extracted (2×) with Et$_2$O. The combined organic layers were washed with brine, dried over MgSO$_4$, filtered, and evaporated under reduced pressure. The residue was purified by flash chromatography on silica gel (40 g) using a gradient of heptane/EtOAc 100/0 to 0/100. The desired fractions were combined and evaporated under reduced pressure, and co-evaporated with toluene. The residue was dried under vacuum at 45° C. to provide methyl 4-(5-chloro-2-(2-oxo-2-(6-(trifluoromethoxy)indolin-1-yl)ethyl)phenoxy)-2,2-dimethylbutanoate 14c (790 mg) as a powder.

Synthesis of Intermediate 14d

A solution of methyl 4-(5-chloro-2-(2-oxo-2-(6-(trifluoromethoxy)indolin-1-yl)ethyl)phenoxy)-2,2-dimethylbutanoate 14c (790 mg, 1.58 mmol) in 2-Me-THF (30 mL) was stirred under N$_2$-flow and cooled to −78° C. A solution of 1M lithium bis(trimethylsilyl)amide in THF (3.16 mL, 3.16 mmol) was added dropwise and the resulting mixture was stirred at −78° C. for 30 minutes. Chlorotrimethylsilane (323 µL, 2.53 mmol) was added dropwise and the mixture was stirred at −78° C. for 25 min. A solution of N-bromosuccinimide (352 mg, 1.98 mmol) in 2-Me-THF (7.5 mL) and THF (2.5 mL) was added dropwise and the reaction mixture was stirred at −78° C. for 45 min. An aqueous saturated solution of NH$_4$Cl (50 mL) was added slowly, and the resulting mixture was stirred without cooling until the temperature reached 0° C. Water (10 mL) was added and, after stirring for 30 min, the layers were separated. The organic layer was dried over MgSO$_4$, filtered, evaporated under reduced pressure, and co-evaporated with CH$_3$CN to provide methyl 4-(2-(1-bromo-2-oxo-2-(6-(trifluoromethoxy)indolin-1-yl)ethyl)-5-chlorophenoxy)-2,2-dimethylbutanoate 14d (915 mg). The product was used without further purification in the next step.

Synthesis of Intermediate 14e

To a stirred solution of methyl 4-(2-(1-bromo-2-oxo-2-(6-(trifluoromethoxy)indolin-1-yl)ethyl)-5-chlorophenoxy)-2,2-dimethylbutanoate 14d (915 mg, 1.58 mmol) in CH$_3$CN (40 mL), under N$_2$-atm, were added 3-methoxy-5-(1H-1,2,4-triazol-1-yl)aniline [CAS 1220630-56-7] (301 mg, 1.58 mmol), and diisopropylethylamine (545 µL, 3.16 mmol) and the reaction mixture was stirred at 50° C. for 18 h and 70°

C. for 6 h. The mixture was cooled to room temperature and poured out into stirring H$_2$O (200 mL). The product was extracted (2×) with Et$_2$O. The combined organic layers were washed with brine, dried over MgSO$_4$, filtered, and evaporated under reduced pressure. The residue was purified by flash chromatography on silica gel (40 g) using a gradient of heptane/EtOAc/EtOH 100/0/0 to 40/45/15. The desired fractions were combined and the solvent was evaporated under reduced pressure and co-evaporated with dioxane to provide methyl 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)-2,2-dimethylbutanoate 14e (1.09 g). The product was used in the next step without purification.

Synthesis of Compound 14 and Chiral Separation into Enantiomers 14A and 14B

1M NaOH (3.95 mL, 3.95 mmol) was added to a stirring solution of methyl 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)-2,2-dimethylbutanoate 14e (1.09 g, 1.58 mmol) in dioxane (6.5 mL The reaction mixture was stirred at room temperature for 40 h. Water (21 mL) and 1N HCl (4.1 mL) were added and after stirring for 10 minutes, the precipitate was filtered off, and washed (3×) with water. The solid residue (0.9 g) was stirred up in CH$_2$Cl$_2$ (7.5 mL) for 45 minutes, filtered off, washed (3×) with CH$_2$Cl$_2$, and dried under vacuum at 45° C. to provide racemic 4-(5-chloro-2-(1-((3-methoxy-5-(1H-1,2,4-triazol-1-yl)phenyl)amino)-2-oxo-2-(6-(trifluoromethoxy)indolin-1-yl)ethyl)phenoxy)-2,2-dimethylbutanoic acid (Compound 14, 590 mg).

The enantiomers of Compound 14 (557 mg) were separated via Preparative Chiral SFC (Stationary phase: Chiralpak® Diacel AD 20×250 mm, Mobile phase: CO$_2$, EtOH+ 0.4% iPrNH$_2$). The fractions containing the first eluted product were combined, evaporated under reduced pressure and co-evaporated with CH$_3$CN. The residue was crystallized from Et$_2$O/heptane 3/1, filtered off, washed (3×) with Et$_2$O, and dried under vacuum at 50° C. to provide Enantiomer 14A (96 mg). The fractions containing the second eluted product were combined, evaporated under reduced pressure and co-evaporated with CH$_3$CN. The residue was crystallized from Et$_2$O, filtered off, washed (3×) with Et$_2$O, and dried under vacuum at 50° C. to provide Enantiomer 14B (35 mg+106 mg (second crop)).

Compound 14:
$^1$H NMR (400 MHz, DMSO-d$_6$) δ ppm 1.11 (d, J=5.1 Hz, 6H) 1.86-2.03 (m, 2H) 3.09-3.28 (m, 2H) 3.73 (s, 3H) 4.01-4.18 (m, 3H) 4.38 (td, J=10.2, 6.6 Hz, 1H) 5.69 (d, J=8.6 Hz, 1H) 6.33 (t, J=2.0 Hz, 1H) 6.67 (t, J=1.9 Hz, 1H) 6.79-6.86 (m, 2H) 6.97-7.05 (m, 2H) 7.18 (d, J=1.8 Hz, 1H) 7.31 (d, J=8.1 Hz, 1H) 7.34 (d, J=8.1 Hz, 1H) 8.03 (br s, 1H) 8.15 (s, 1H) 9.14 (s, 1H) 12.25 (br s, 1H)
LC/MS (method LC-C): R$_t$ 1.12 min, MH$^+$ 674

Enantiomer 14A:
$^1$H NMR (400 MHz, DMSO-d$_6$) δ ppm 1.11 (d, J=5.1 Hz, 6H) 1.87-2.02 (m, 2H) 3.09-3.26 (m, 2H) 3.73 (s, 3H) 4.02-4.18 (m, 3H) 4.37 (td, J=10.2, 6.6 Hz, 1H) 5.69 (d, J=8.8 Hz, 1H) 6.33 (t, J=2.2 Hz, 1H) 6.67 (t, J=1.8 Hz, 1H) 6.79-6.86 (m, 2H) 6.99-7.04 (m, 2H) 7.18 (d, J=2.0 Hz, 1H) 7.31 (d, J=8.1 Hz, 1H) 7.34 (d, J=8.4 Hz, 1H) 8.03 (br s, 1H) 8.15 (s, 1H) 9.14 (s, 1H) 12.25 (br s, 1H)
LC/MS (method LC-D): R$_t$ 2.09 min, MH$^+$ 674
[α]$_D^{20}$: −32.8° (c 0.528, DMF)
Chiral SFC (method SFC-K): R$_t$ 3.63 min, MH$^+$ 674, chiral purity 100%.
Melting point: 111° C.

Enantiomer 14B:
$^1$H NMR (400 MHz, DMSO-d$_6$) δ ppm 1.11 (d, J=5.1 Hz, 6H) 1.87-2.02 (m, 2H) 3.10-3.27 (m, 2H) 3.73 (s, 3H) 4.03-4.18 (m, 3H) 4.38 (td, J=10.2, 6.5 Hz, 1H) 5.69 (d, J=8.6 Hz, 1H) 6.33 (t, J=1.9 Hz, 1H) 6.67 (t, J=1.9 Hz, 1H) 6.79-6.86 (m, 2H) 6.98-7.05 (m, 2H) 7.18 (d, J=1.8 Hz, 1H) 7.31 (d, J=8.4 Hz, 1H) 7.34 (d, J=8.1 Hz, 1H) 8.03 (br s, 1H) 8.15 (s, 1H) 9.14 (s, 1H) 12.25 (br s, 1H)
LC/MS (method LC-D): R$_t$ 2.08 min, MH$^+$ 674
[α]$_D^{20}$: +32.8° (c 0.515, DMF)
Chiral SFC (method SFC-K): R$_t$ 4.22 min, MH$^+$ 674, chiral purity 100%.
Melting point: 177° C.

Example 15: Synthesis of 4-(5-chloro-2-(2-(5-fluoro-6-(trifluoromethoxy)indolin-1-yl)-1-((3-methoxy-5-(1H-1,2,4-triazol-1-yl)phenyl)amino)-2-oxoethyl)phenoxy)butanoic acid (Compound 15) and Chiral Separation into Enantiomers 15A and 15B

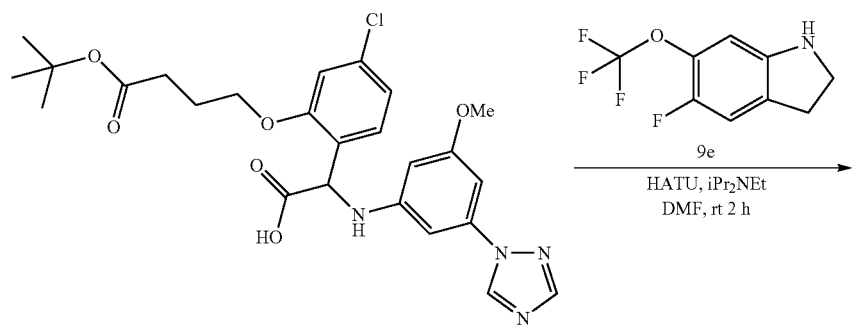

11d

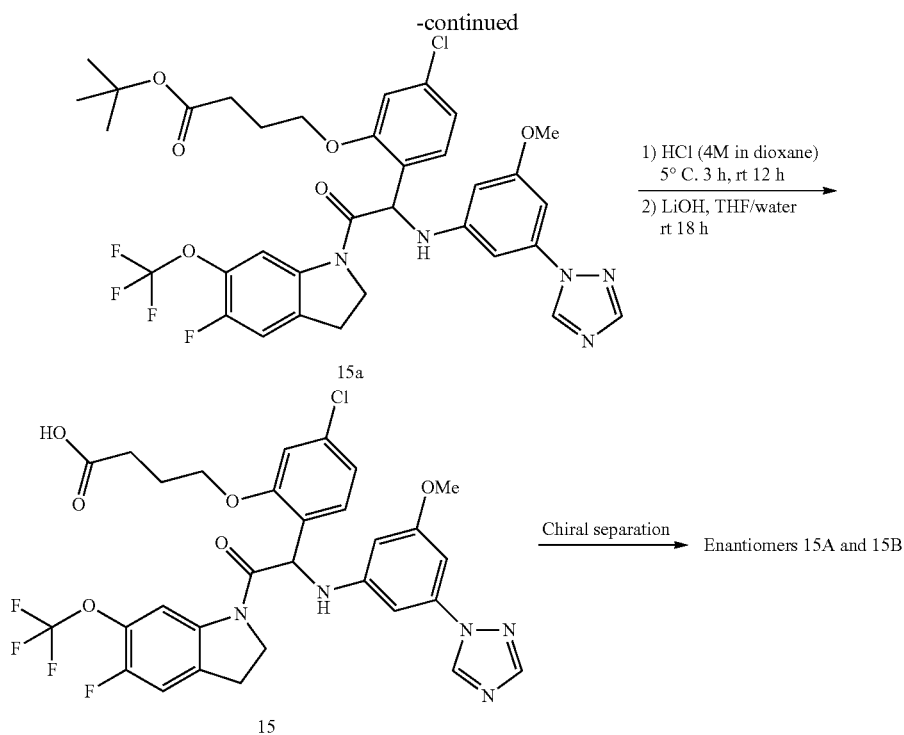

Synthesis of Intermediate 15a

A mixture of 5-fluoro-6-(trifluoromethoxy)indoline 9e (321 mg, 1.45 mmol), 2-(2-(4-(tert-butoxy)-4-oxobutoxy)-4-chlorophenyl)-2-((3-methoxy-5-(1H-1,2,4-triazol-1-yl)phenyl)amino)acetic acid 11d (750 mg, 1.45 mmol), HATU (827 mg, 2.18 mmol) and diisopropylethylamine (719 µL, 4.35 mmol) in DMF (30 mL) was stirred at room temperature for 12 h. The mixture was diluted with water. The precipitate was filtered off, washed with water and taken up with EtOAc. The organic solution was washed with a 10% solution of $K_2CO_3$ in water, water, dried over $MgSO_4$, filtered and the solvent was concentrated under reduced pressure. The residue was purified by flash chromatography on silica gel (15-40 µm, 40 g, $CH_2Cl_2$/MeOH 98/2). The pure fractions were combined and concentrated to dryness to give tert-butyl 4-(5-chloro-2-(2-(5-fluoro-6-(trifluoromethoxy)indolin-1-yl)-1-((3-methoxy-5-(1H-1,2,4-triazol-1-yl)phenyl)amino)-2-oxoethyl)phenoxy)butanoate 15a (1.05 g).

Synthesis of Compound 15 and Chiral Separation into Enantiomers 15A and 15B

A solution of tert-butyl 4-(5-chloro-2-(2-(5-fluoro-6-(trifluoromethoxy)indolin-1-yl)-1-((3-methoxy-5-(1H-1,2,4-triazol-1-yl)phenyl)amino)-2-oxoethyl)phenoxy)butanoate 15a (1.05 g, 1.46 mmol) in 4M HCl in dioxane (8 mL) was stirred at 5° C. for 3 h and at room temperature for 12 h. The precipitate was filtered off, washed with dioxane/diisopropyl ether and dried. The residue (580 mg) was dissolved in THF (2.5 mL) and a solution of lithium hydroxide monohydrate (180 mg, 4.277 mmol) in water (2.5 mL) was added dropwise. The mixture was stirred at room temperature for 18 h. The reaction was cooled to 0° C. and water and ice were added. The pH was adjusted to 6 by the addition of 3N HCl. The product was extracted with EtOAc. The organic layer was separated, dried over $MgSO_4$, filtered and the solvent was concentrated under reduced pressure. A small fraction of the residue was crystallized from $CH_2Cl_2$ to give 4-(5-chloro-2-(2-(5-fluoro-6-(trifluoromethoxy)indolin-1-yl)-1-((3-methoxy-5-(1H-1,2,4-triazol-1-yl)phenyl)amino)-2-oxoethyl)phenoxy)butanoic acid 15 (24 mg) as a racemate. The remaining amount was further purified by flash chromatography on silica gel (20-45 µm, 24 g, $CH_2Cl_2$/MeOH gradient 99.5/0.5 to 90/10). The pure fractions were combined and concentrated to dryness to provide a second fraction of Compound 15 (382 mg).

The enantiomers of Compound 15 (382 mg) were separated via Preparative Chiral SFC (Stationary phase: Chiralcel® OD-H 5 µm 250×30 mm, Mobile phase: 75% $CO_2$, 25% MeOH (+0.3% iPrNH$_2$)). The first eluted enantiomer (178 mg) was solidified by titration with heptane/diisopropyl ether to give Enantiomer 15A (140 mg). The second eluted enantiomer (187 mg) was solidified by titration with heptane/diisopropyl ether to give Enantiomer 15B (136 mg).

Compound 15:
$^1$H NMR (500 MHz, DMSO-d$_6$) δ ppm 1.90-2.04 (m, 2H) 2.28-2.46 (m, 2H) 3.11-3.28 (m, 2H) 3.73 (s, 3H) 4.03-4.18 (m, 3H) 4.33-4.42 (m, 1H) 5.71 (d, J=8.8 Hz, 1H) 6.34 (s, 1H) 6.67 (s, 1H) 6.81 (s, 1H) 6.87 (br d, J=8.8 Hz, 1H) 7.02 (dd, J=8.2, 1.9 Hz, 1H) 7.12 (s, 1H) 7.31 (d, J=8.2 Hz, 1H) 7.43 (d, J=9.8 Hz, 1H) 8.12-8.20 (m, 2H) 9.16 (s, 1H) 12.12 (br s, 1H)

LC/MS (method LC-B): $R_t$ 2.72 min, MH$^+$ 664

Melting point: 188° C.

Enantiomer 15A:
$^1$H NMR (400 MHz, DMSO-d$_6$) δ ppm 1.88-2.12 (m, 2H) 2.19-2.42 (m, 2H) 2.96-3.24 (m, 2H) 3.73 (s, 3H) 3.89-4.16 (m, 3H) 4.25-4.43 (m, 1H) 5.72 (d, J=8.6 Hz, 1H) 6.34 (s, 1H) 6.66 (s, 1H) 6.79-6.86 (m, 2H) 7.01 (dd, J=8.3, 1.8 Hz, 1H) 7.09-7.14 (m, 1H) 7.32 (d, J=8.1 Hz, 1H) 7.41 (d, J=9.6 Hz, 1H) 8.12-8.17 (m, 2H) 9.16 (s, 1H)

LC/MS (method LC-B): $R_t$ 2.75 min, MH+ 664
$[\alpha]_D^{20}$: −31.5° (c 0.267, DMF)
Chiral SFC (method SFC-J): $R_t$ 2.66 min, MH+ 664, chiral purity 99.69%.
Enantiomer 15B:
$^1$H NMR (400 MHz, DMSO-$d_6$) δ ppm 1.88-2.04 (m, 2H) 2.22-2.43 (m, 2H) 3.12-3.40 (m, 2H) 3.72 (s, 3H) 4.03-4.17 (m, 3H) 4.33-4.43 (m, 1H) 5.72 (d, J=8.6 Hz, 1H) 6.34 (s, 1H) 6.67 (s, 1H) 6.78-6.87 (m, 2H) 7.01 (dd, J=8.3, 1.8 Hz, 1H) 7.09-7.13 (m, 1H) 7.32 (d, J=8.1 Hz, 1H) 7.41 (d, J=9.6 Hz, 1H) 8.12-8.18 (m, 2H) 9.16 (s, 1H)

LC/MS (method LC-B): $R_t$ 2.73 min, MH+ 664
$[\alpha]_D^{20}$: +28.2° (c 0.262, DMF)
Chiral SFC (method SFC-J): $R_t$ 3.53 min, MH+ 664, chiral purity 98.93%.

Example 16: Synthesis of 4-(5-chloro-2-(1-((3-methoxy-5-(1H-1,2,4-triazol-1-yl)phenyl)amino)-2-(4-methyl-6-(trifluoromethoxy)indolin-1-yl)-2-oxo-ethyl)phenoxy)butanoic acid (Compound 16) and Chiral Separation into Enantiomers 16A and 16B

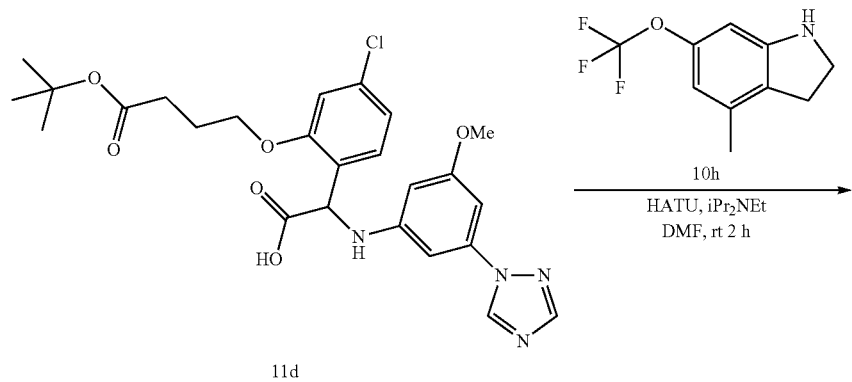

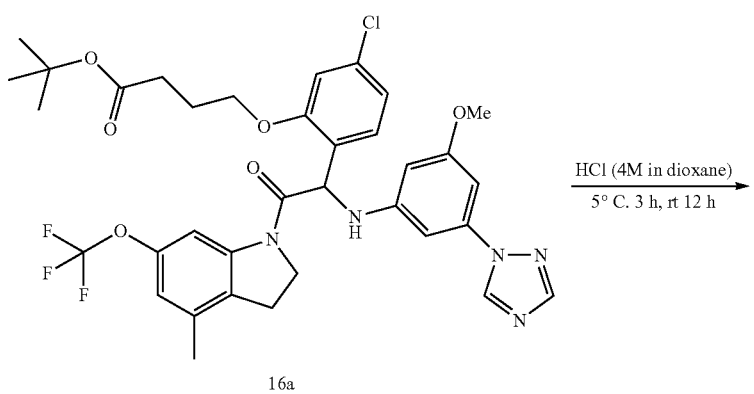

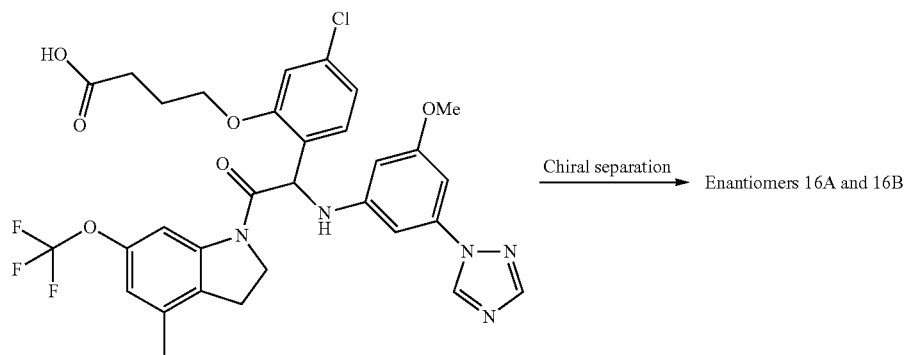

Synthesis of Intermediate 16a

A mixture of 4-methyl-6-(trifluoromethoxy)indoline 10h (336 mg, 1.55 mmol), 2-(2-(4-(tert-butoxy)-4-oxobutoxy)-4-chlorophenyl)-2-((3-methoxy-5-(1H-1,2,4-triazol-1-yl)phenyl)amino)acetic acid 11d (800 mg, 1.55 mmol), HATU (883 mg, 2.32 mmol) and diisopropylethylamine (767 μL, 4.64 mmol) in DMF (30 mL) was stirred at room temperature for 12 h. The mixture was diluted with water. The precipitate was filtered off, washed with water and taken up with EtOAc. The organic solution was washed with a 10% solution of $K_2CO_3$ in water, water, dried over $MgSO_4$, filtered and the solvent was concentrated under reduced pressure. The residue was purified by flash chromatography on silica gel (15-40 μm, 40 g, heptane/EtAOc gradient 90/10 to 70/30). The pure fractions were combined and concentrated to dryness to give tert-butyl 4-(5-chloro-2-(1-((3-methoxy-5-(1H-1,2,4-triazol-1-yl)phenyl)amino)-2-(4-methyl-6-(trifluoromethoxy)indolin-1-yl)-2-oxoethyl)phenoxy)butanoate 16a (816 mg).

Synthesis of Compound 16 and Chiral Separation into Enantiomers 16A and 16B

A solution of tert-butyl 4-(5-chloro-2-(1-((3-methoxy-5-(1H-1,2,4-triazol-1-yl)phenyl)amino)-2-(4-methyl-6-(trifluoromethoxy)indolin-1-yl)-2-oxoethyl)phenoxy)butanoate 16a (816 mg, 1.14 mmol) in 4M HCl in dioxane (7 mL) was stirred at 5° C. for 2 h and at room temperature for 12 h. The precipitate was filtered off, washed with dioxane/diisopropyl ether and dried. The residue was purified by flash chromatography on silica gel (20-45 μm, 40 g, $CH_2Cl_2$/MeOH gradient 100/0 to 95/5). Pure fractions were combined and solvent was evaporated under reduced pressure to give, after crystallization from $CH_3CN$/diisopropyl ether, 4-(5-chloro-2-(1-((3-methoxy-5-(1H-1,2,4-triazol-1-yl)phenyl)amino)-2-(4-methyl-6-(trifluoromethoxy)indolin-1-yl)-2-oxoethyl)phenoxy)butanoic acid 16 (495 mg).

The enantiomers of Compound 16 were separated via Preparative Chiral SFC (Stationary phase: Chiralpak® AD-H 5 μm 250×30 mm, Mobile phase: 65% $CO_2$, 35% iPrOH (+0.3% $iPrNH_2$)). The first eluted enantiomer (145 mg) was further purified by flash chromatography on silica gel (10-40 μm, 24 g, $CH_2Cl_2$/MeOH 98/2). The pure fractions were combined and the solvent was concentrated under reduced pressure to give, after solidification by trituration with diisopropyl ether/pentane, Enantiomer 16A (99 mg). The second eluted enantiomer (149 mg) was further purified by flash chromatography on silica gel (10-40 μm, 24 g, $CH_2Cl_2$/MeOH 98/2). The pure fractions were combined and the solvent was concentrated under reduced pressure to give, after solidification by trituration with diisopropyl ether/pentane, Enantiomer 16B (95 mg).

Compound 16:
$^1$H NMR (400 MHz, DMSO-$d_6$) δ ppm 1.91-2.05 (m, 2H) 2.20 (s, 3H) 2.29-2.43 (m, 2H) 3.01-3.27 (m, 2H) 3.72 (s, 3H) 4.02-4.18 (m, 3H) 4.35-4.44 (m, 1H) 5.71 (br d, J=8.6 Hz, 1H) 6.34 (br s, 1H) 6.67 (s, 1H) 6.78-6.90 (m, 3H) 7.01 (br d, J=7.1 Hz, 1H) 7.12 (s, 1H) 7.31 (d, J=8.1 Hz, 1H) 7.88 (br s, 1H) 8.15 (s, 1H) 9.14 (s, 1H) 12.07 (br s, 1H)
LC/MS (method LC-A): $R_t$ 2.93 min, MH$^+$ 660
Melting point: 214° C.

Enantiomer 16A:
$^1$H NMR (400 MHz, DMSO-$d_6$) δ ppm 1.92-2.04 (m, 2H) 2.20 (s, 3H) 2.30-2.44 (m, 2H) 2.99-3.16 (m, 2H) 3.73 (s, 3H) 4.04-4.17 (m, 3H) 4.35-4.44 (m, 1H) 5.71 (br d, J=8.6 Hz, 1H) 6.34 (br s, 1H) 6.67 (s, 1H) 6.79-6.89 (m, 3H) 7.02 (br d, J=8.6 Hz, 1H) 7.12 (s, 1H) 7.32 (d, J=8.1 Hz, 1H) 7.89 (s, 1H) 8.15 (s, 1H) 9.14 (s, 1H) 12.09 (br s, 1H)
LC/MS (method LC-A): $R_t$ 2.94 min, MH$^+$ 660
$[α]_D^{20}$: −35.4° (c 0.263, DMF)
Chiral SFC (method SFC-F): $R_t$ 1.61 min, MH$^+$ 660, chiral purity 100%.

Enantiomer 16B:
$^1$H NMR (400 MHz, DMSO-$d_6$) δ ppm 1.91-2.04 (m, 2H) 2.20 (s, 3H) 2.30-2.44 (m, 2H) 3.00-3.15 (m, 2H) 3.73 (s, 3H) 4.03-4.17 (m, 3H) 4.35-4.44 (m, 1H) 5.71 (d, J=8.6 Hz, 1H) 6.34 (s, 1H) 6.67 (s, 1H) 6.79-6.89 (m, 3H) 7.02 (dd, J=8.1, 1.5 Hz, 1H) 7.10-7.14 (m, 1H) 7.32 (d, J=8.59 Hz, 1H) 7.89 (s, 1H) 8.15 (s, 1H) 9.14 (s, 1H) 12.10 (br s, 1H)
LC/MS (method LC-A): $R_t$ 2.94 min, MH$^+$ 660
$[α]_D^{20}$: +34.3° (c 0.274, DMF)
Chiral SFC (method SFC-F): $R_t$ 2.22 min, MH$^+$ 660, chiral purity 99.47%.

TABLE

Compounds prepared as described above

| Compound | Structure | Optical rotation |
|---|---|---|
| 1 | 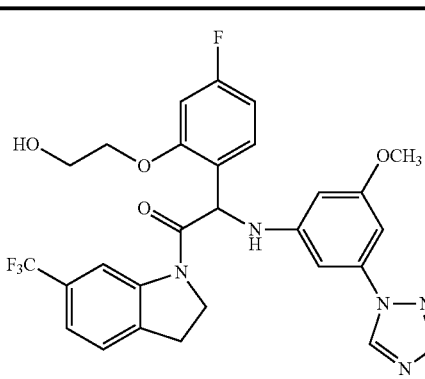 | racemic |

TABLE-continued

Compounds prepared as described above

| Compound | Structure | Optical rotation |
|---|---|---|
| 1A | (structure: 4-fluoro-2-(2-hydroxyethoxy)phenyl group, (−) stereocenter with NH linked to 3-methoxy-5-(1,2,4-triazol-1-yl)phenyl, carbonyl linked to 6-trifluoromethylindoline) | $[\alpha]_D^{20} = -44.8°$ |
| 1B | (structure: same as 1A but (+) stereocenter) | $[\alpha]_D^{20} = +36.2°$ |
| 2 | (structure: 4-fluoro-2-(2-hydroxyethoxy)phenyl, NH linked to 3-methoxy-5-(1,2,4-triazol-1-yl)phenyl, carbonyl linked to 5-methoxy-6-trifluoromethylindoline) | racemic |
| 2A | (structure: same as compound 2 with (−) stereocenter) | $[\alpha]_D^{20} = -45.0°$ |

TABLE-continued

| Compounds prepared as described above | | |
|---|---|---|
| Compound | Structure | Optical rotation |
| 2B | (structure) | $[\alpha]_D^{20} = +43.4°$ |
| 3 | (structure) | racemic |
| 3A | (structure) | $[\alpha]_D^{20} = -38.2°$ |
| 3B | (structure) | $[\alpha]_D^{20} = +40.9°$ |

TABLE-continued

Compounds prepared as described above

| Compound | Structure | Optical rotation |
|---|---|---|
| 4 | 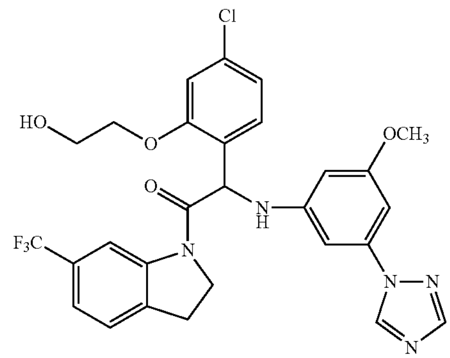 | racemic |
| 4A | 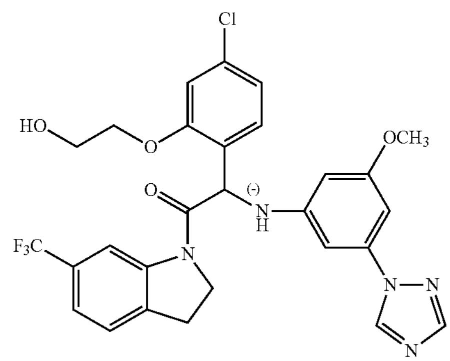 | $[\alpha]_D^{20} = -42.9°$ |
| 4B | 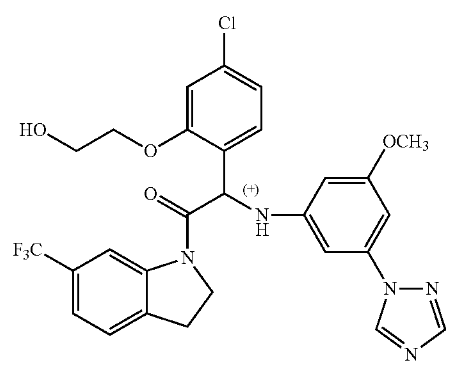 | $[\alpha]_D^{20} = +39.5°$ |
| 5 | 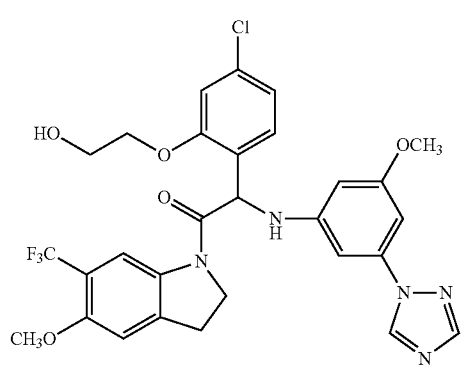 | racemic |

TABLE-continued

Compounds prepared as described above

| Compound | Structure | Optical rotation |
|---|---|---|
| 5A | (structure) | $[\alpha]_D^{20} = -40.3°$ |
| 5B | (structure) | $[\alpha]_D^{20} = +40.0°$ |
| 6 | (structure) | racemic |
| 6A | (structure) | $[\alpha]_D^{20} = +45.9°$ |

TABLE-continued

Compounds prepared as described above

| Compound | Structure | Optical rotation |
|---|---|---|
| 6B | 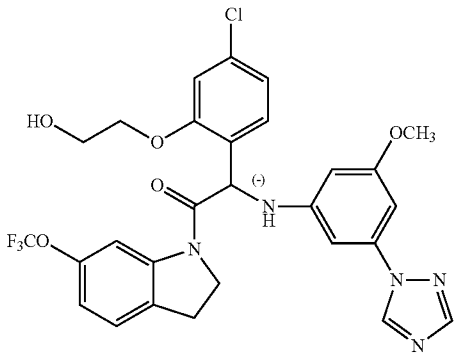 | $[\alpha]_D^{20} = -46.3°$ |
| 7 | 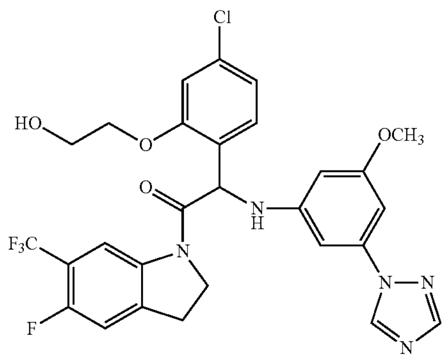 [SMILES: COc1cc(NC(C(=O)N2CCc3cc(F)c(C(F)(F)F)cc32)c2ccc(Cl)cc2OCCO)cc(-n2cncn2)c1] | racemic |
| 7A | 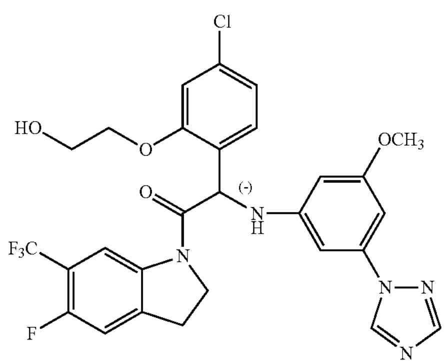 [SMILES: COc1cc(NC(C(=O)N2CCc3cc(F)c(C(F)(F)F)cc32)c2ccc(Cl)cc2OCCO)cc(-n2cncn2)c1] | $[\alpha]_D^{20} = -44.3°$ |
| 7B | 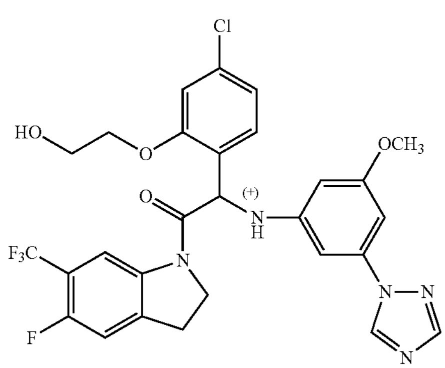 [SMILES: COc1cc(NC(C(=O)N2CCc3cc(F)c(C(F)(F)F)cc32)c2ccc(Cl)cc2OCCO)cc(-n2cncn2)c1] | $[\alpha]_D^{20} = +35.6°$ |

TABLE-continued

| Compounds prepared as described above | | |
|---|---|---|
| Compound | Structure | Optical rotation |
| 8 | | racemic |
| 8A | | $[\alpha]_D^{20} = +39.3°$ |
| 8B | | $[\alpha]_D^{20} = -44.4°$ |
| 9 | | racemic |

TABLE-continued

Compounds prepared as described above

| Compound | Structure | Optical rotation |
| --- | --- | --- |
| 9A | 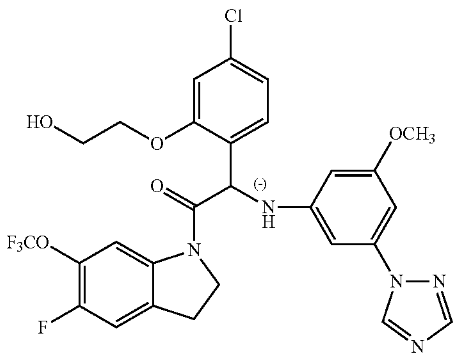 [SMILES: COc1cc(NC(C(=O)N2CCc3cc(F)c(OC(F)(F)F)cc32)c2ccc(Cl)cc2OCCO)cc(-n2cncn2)c1] | $[\alpha]_D^{20} = -35.1°$ |
| 9B | 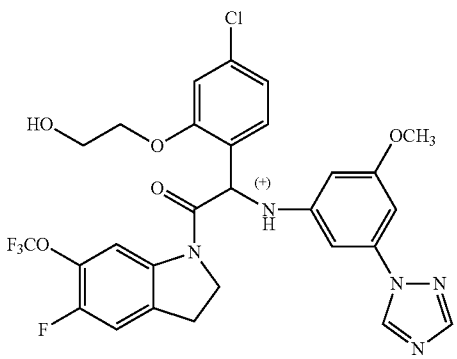 [SMILES: COc1cc(NC(C(=O)N2CCc3cc(F)c(OC(F)(F)F)cc32)c2ccc(Cl)cc2OCCO)cc(-n2cncn2)c1] | $[\alpha]_D^{20} = +32.3°$ |
| 10 | 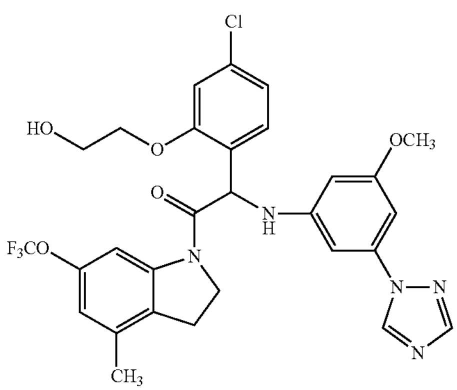 [SMILES: COc1cc(NC(C(=O)N2CCc3c(C)cc(OC(F)(F)F)cc32)c2ccc(Cl)cc2OCCO)cc(-n2cncn2)c1] | racemic |
| 10A | 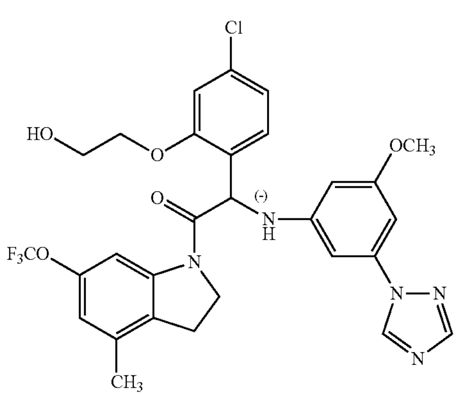 [SMILES: COc1cc(NC(C(=O)N2CCc3c(C)cc(OC(F)(F)F)cc32)c2ccc(Cl)cc2OCCO)cc(-n2cncn2)c1] | $[\alpha]_D^{20} = -38.4°$ |

TABLE-continued

Compounds prepared as described above

| Compound | Structure | Optical rotation |
|---|---|---|
| 10B | 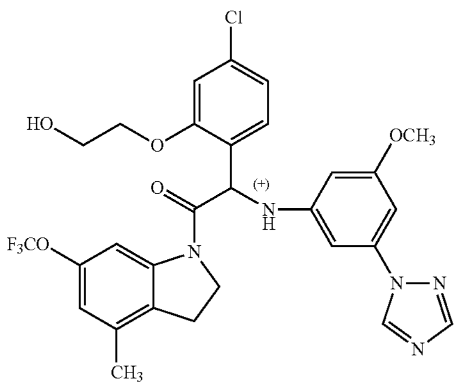 [SMILES: COc1cc(NC(C(=O)N2CCc3c(C)cc(OC(F)(F)F)cc32)c2ccc(Cl)cc2OCCO)cc(-n2cncn2)c1] | $[\alpha]_D^{20} = +37.5°$ |
| 11 | 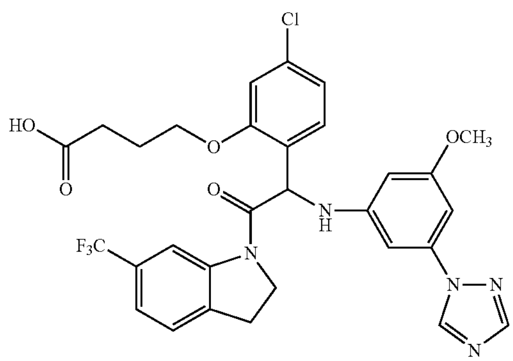 [SMILES: COc1cc(NC(C(=O)N2CCc3ccc(C(F)(F)F)cc32)c2ccc(Cl)cc2OCCCC(=O)O)cc(-n2cncn2)c1] | racemic |
| 11A | 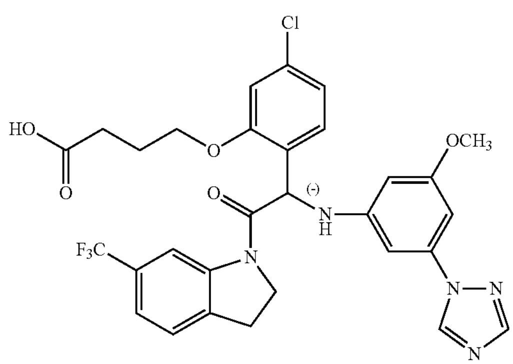 [SMILES: COc1cc(NC(C(=O)N2CCc3ccc(C(F)(F)F)cc32)c2ccc(Cl)cc2OCCCC(=O)O)cc(-n2cncn2)c1] | $[\alpha]_D^{20} = -28.9°$ |
| 11B | 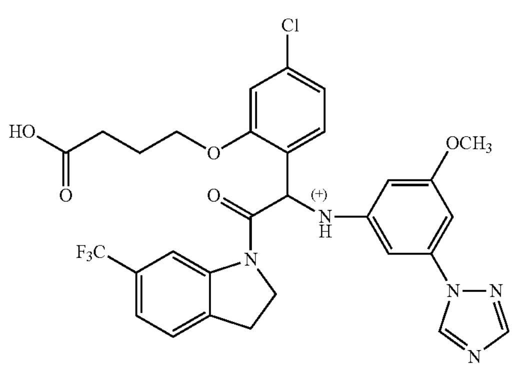 | $[\alpha]_D^{20} = +23.8°$ |

TABLE-continued

Compounds prepared as described above

| Compound | Structure | Optical rotation |
|---|---|---|
| 12 | 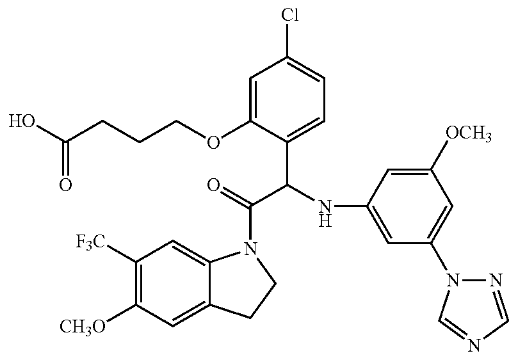 | racemic |
| 12A | 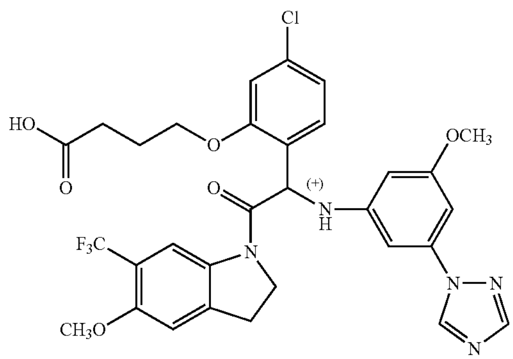 | $[\alpha]_D^{20} = +30.4°$ |
| 12B | 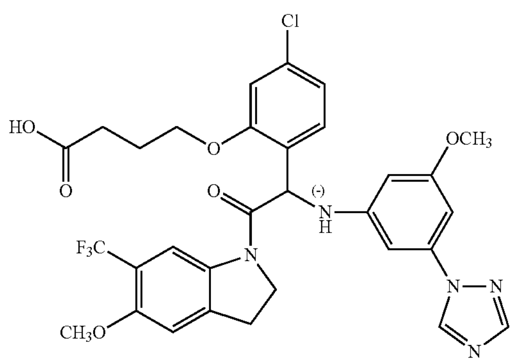 | $[\alpha]_D^{20} = -36.9°$ |
| 13 | 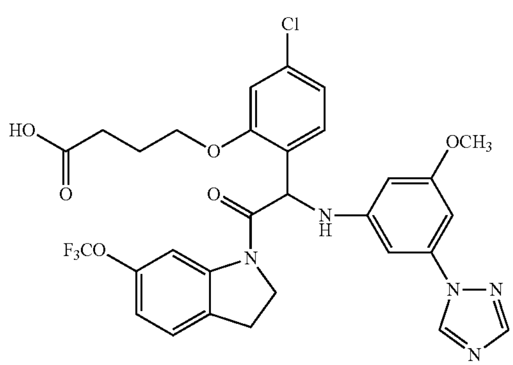 [SMILES: COc1cc(NC(C(=O)N2CCc3ccc(OC(F)(F)F)cc32)c2ccc(Cl)cc2OCCCC(=O)O)cc(-n2cncn2)c1] | racemic |

TABLE-continued

Compounds prepared as described above

| Compound | Structure | Optical rotation |
|---|---|---|
| 13A | 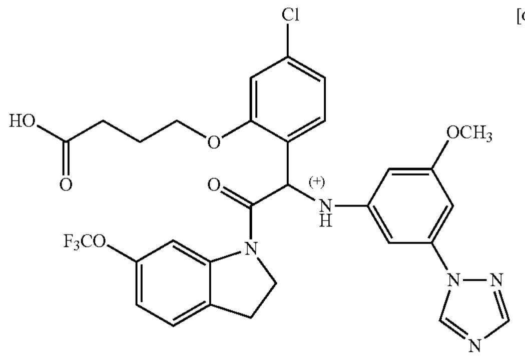 | $[\alpha]_D^{20} = +38.4°$ |
| 13B | 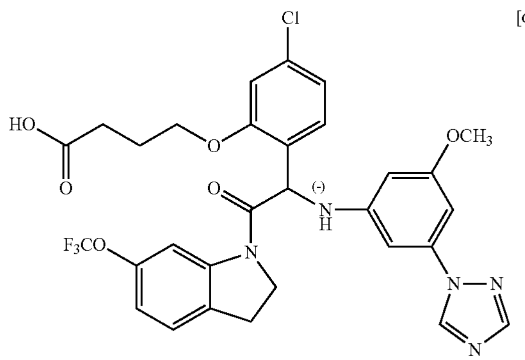 | $[\alpha]_D^{20} = -43.2°$ |
| 14 | 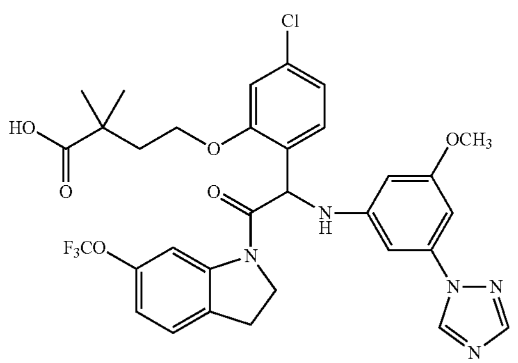 [SMILES: COc1cc(NC(C(=O)N2CCc3ccc(OC(F)(F)F)cc32)c2ccc(Cl)cc2OCCC(C)(C)C(=O)O)cc(-n2cncn2)c1] | racemic |
| 14A | 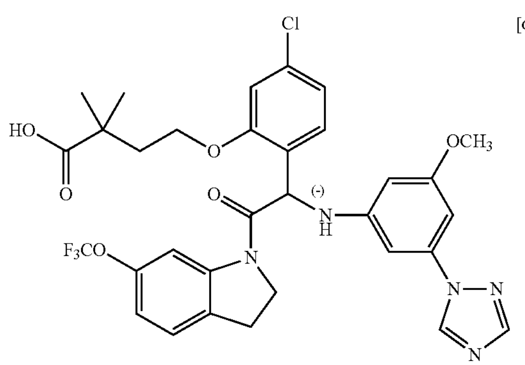 | $[\alpha]_D^{20} = -32.8°$ |

TABLE-continued

Compounds prepared as described above

| Compound | Structure | Optical rotation |
|---|---|---|
| 14B | 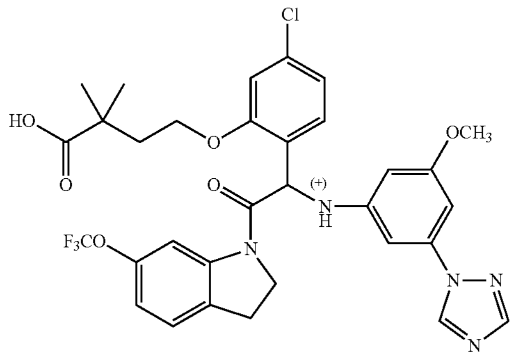 [SMILES: COc1cc(NC(C(=O)N2CCc3ccc(OC(F)(F)F)cc32)c2ccc(Cl)cc2OCCC(C)(C)C(=O)O)cc(-n2cncn2)c1] | $[\alpha]_D^{20} = +32.8°$ |
| 15 | 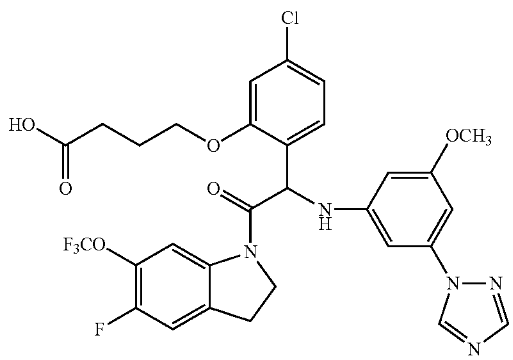 [SMILES: COc1cc(NC(C(=O)N2CCc3cc(F)c(OC(F)(F)F)cc32)c2ccc(Cl)cc2OCCCC(=O)O)cc(-n2cncn2)c1] | racemic |
| 15A | 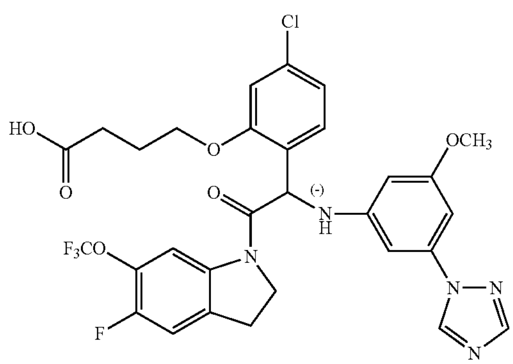 [SMILES: COc1cc(NC(C(=O)N2CCc3cc(F)c(OC(F)(F)F)cc32)c2ccc(Cl)cc2OCCCC(=O)O)cc(-n2cncn2)c1] | $[\alpha]_D^{20} = -31.5°$ |
| 15B | 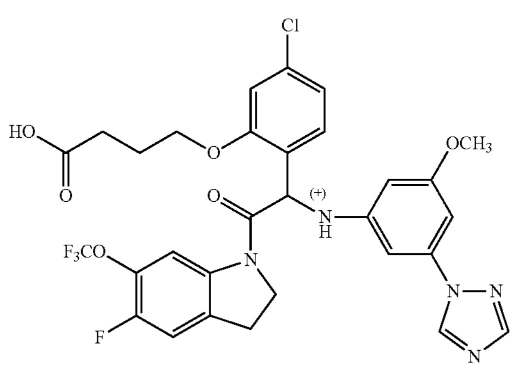 [SMILES: COc1cc(NC(C(=O)N2CCc3cc(F)c(OC(F)(F)F)cc32)c2ccc(Cl)cc2OCCCC(=O)O)cc(-n2cncn2)c1] | $[\alpha]_D^{20} = +28.2°$ |

TABLE-continued

Compounds prepared as described above

| Compound | Structure | Optical rotation |
|---|---|---|
| 16 | 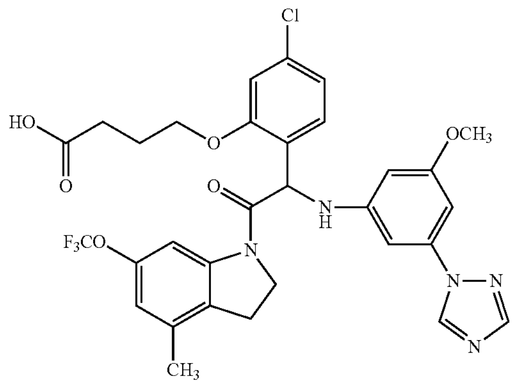 [SMILES: COc1cc(NC(C(=O)N2CCc3c(C)cc(OC(F)(F)F)cc32)c2ccc(Cl)cc2OCCCC(=O)O)cc(-n2cncn2)c1] | racemic |
| 16A | 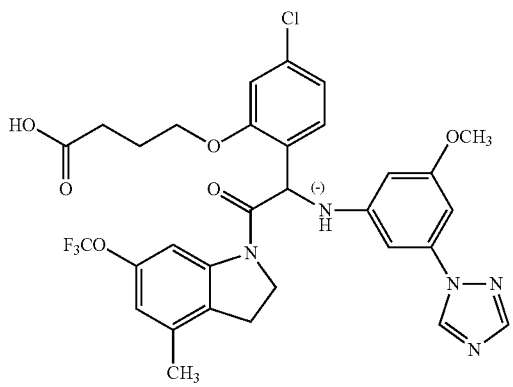 [SMILES: COc1cc(NC(C(=O)N2CCc3c(C)cc(OC(F)(F)F)cc32)c2ccc(Cl)cc2OCCCC(=O)O)cc(-n2cncn2)c1] | $[\alpha]_D^{20} = -35.4°$ |
| 16B | 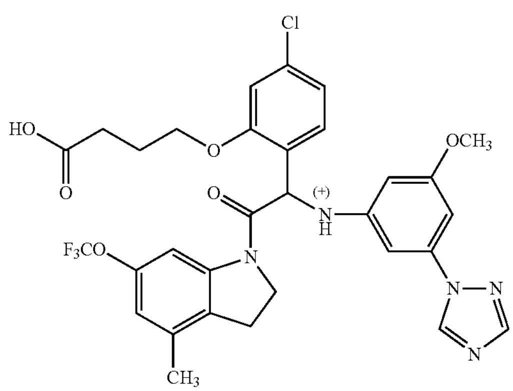 [SMILES: COc1cc(NC(C(=O)N2CCc3c(C)cc(OC(F)(F)F)cc32)c2ccc(Cl)cc2OCCCC(=O)O)cc(-n2cncn2)c1] | $[\alpha]_D^{20} = +34.3°$ |

Antiviral Activity of the Compounds of the Invention
DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 μM-0.000064 μM or 2.5 μM-0.0000064 μM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% CO₂) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$, $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 μL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (μM) | N | $CC_{50}$ (μM) | N | SI | N |
|---|---|---|---|---|---|---|
| 1 | 0.0031 | 4 | 12 | 4 | 3350 | 4 |
| 1A | 1.00 | 3 | 7.7 | 3 | 7.8 | 3 |
| 1B | 0.0028 | 4 | 9.8 | 2 | 3530 | 2 |
| 2 | 0.0028 | 4 | 13 | 4 | 4000 | 4 |
| 2A | 0.27 | 3 | 12 | 3 | 43 | 3 |
| 2B | 0.0018 | 3 | 10 | 3 | 4180 | 3 |
| 3 | 0.0019 | 4 | 8.5 | 4 | 5210 | 4 |
| 3A | 0.52 | 3 | 11 | 3 | 22 | 3 |
| 3B | 0.00099 | 3 | 8.7 | 3 | 11400 | 3 |
| 4A | 1.2 | 4 | 7.8 | 4 | 6.4 | 4 |
| 4B | 0.0010 | 3 | 11 | 3 | 16100 | 3 |
| 5 | 0.00082 | 3 | 11 | 3 | 11200 | 3 |
| 5A | 0.042 | 3 | 11 | 3 | 275 | 3 |
| 5B | 0.00062 | 3 | 9.2 | 3 | 14400 | 3 |
| 6 | 0.00097 | 3 | 3.3 | 3 | 3370 | 3 |
| 6A | 0.00059 | 9 | 8.5 | 3 | 14900 | 9 |
| 6B | 0.092 | 7 | 7.3 | 7 | 79 | 7 |
| 7 | 0.0030 | 3 | 10 | 3 | 3410 | 3 |
| 7A | 0.43 | 3 | 11 | 3 | 26 | 3 |
| 7B | 0.0018 | 3 | 7.6 | 3 | 4180 | 3 |
| 8 | 0.0021 | 3 | 9.5 | 3 | 4410 | 3 |
| 8A | 0.0015 | 3 | 12 | 3 | 7360 | 3 |
| 8B | 0.25 | 3 | 12 | 3 | 47 | 3 |
| 9 | 0.0016 | 4 | 3.9 | 3 | 2850 | 3 |
| 9A | 0.25 | 4 | 4.2 | 4 | 17 | 3 |
| 9B | 0.00060 | 3 | 10 | 3 | 13800 | 3 |
| 10 | 0.00035 | 3 | 10 | 3 | 26600 | 3 |
| 10A | 0.063 | 3 | 10 | 3 | 165 | 3 |
| 10B | 0.00025 | 3 | 11 | 3 | 51400 | 3 |

TABLE 1-continued $EC_{50}$, $CC_{50}$, and SI for the compounds of the invention in the DENV-2 antiviral assay

| compound# | $EC_{50}$ (μM) | N | $CC_{50}$ (μM) | N | SI | N |
|---|---|---|---|---|---|---|
| 11 | 0.00031 | 3 | 15 | 3 | 53500 | 3 |
| 11A | 0.045 | 3 | 11 | 3 | 246 | 3 |
| 11B | 0.00020 | 3 | 12 | 3 | 45200 | 3 |
| 12 | 0.0022 | 3 | 13 | 3 | 5660 | 3 |
| 12A | 0.0012 | 3 | 13 | 3 | 11000 | 3 |
| 12B | 0.32 | 3 | 12 | 3 | 37 | 3 |
| 13 | 0.00023 | 3 | 11 | 3 | 59500 | 3 |
| 13A | 0.00012 | 4 | 12 | 4 | 103601 | 4 |
| 13B | 0.012 | 3 | 12 | 3 | 972 | 3 |
| 14 | 0.00041 | 3 | 10 | 3 | 24900 | 3 |
| 14A | 0.42 | 3 | 9.1 | 3 | 22 | 3 |
| 14B | 0.00027 | 4 | 9.4 | 4 | 35500 | 4 |
| 15 | 0.00022 | 3 | 11 | 3 | 58700 | 3 |
| 15A | 0.0053 | 3 | 10 | 3 | 1970 | 3 |
| 15B | 0.00013 | 3 | 11 | 4 | 94800 | 3 |
| 16 | 0.00011 | 3 | 11 | 3 | 95800 | 3 |
| 16A | 0.014 | 3 | 11 | 3 | 800 | 3 |
| 16B | 0.000069 | 5 | 6.2 | 5 | >174673 | 5 |

N = the number of independent experiments in which the compounds were tested.

Tetravalent Reverse Transcriptase Quantitative-PCR (RT-qPCR) Assay: Protocol A.

The antiviral activity of the compounds of the invention was tested against DENV-1 strain TC974#666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values are determined based on the $C_p$ values acquired for the housekeeping gene β-actin.

TABLE 2

Primers and probes used for the real-time, quantitative RT-PCR.

| Primer/probe | Target | Sequence[a, b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM-5'-AAGGACTAG-ZEN-AGGTTAGAGGAGCCCCCC-3'-*IABkFQ* |
| Factin743 | β-actin | 5'-GGCCAGGTCATCACCATT-3' |
| Ractin876 | β-actin | 5'-ATGTCCACGTCACACTTCATG-3' |

TABLE 2-continued

Primers and probes used for the real-time, quantitative RT-PCR.

| Primer/probe | Target | Sequence[a,b] |
|---|---|---|
| Pactin773 | β-actin | *HEX*-5'-TTCCGCTGC-*ZEN*-CCTGAGGCTCTC-3'-*IABkFQ* |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 μM-0.000064 μM or 2.5 μM-0.0000064 μM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, 2, 3 and 4 were diluted in order to obtain a Cp of ~22-24 in the assay. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), and 22.02 μL/well was dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription.

A
Mix A
Plates 8
Samples 828
Reaction Vol. (μl) 20

| | | | | Volume for (μl) | |
|---|---|---|---|---|---|
| | | Concentration | | 1 | x |
| Mix Item | Unit | Stock | Final | sample | samples |
| Milli-Q $H_2O$ | | | | 7.27 | 6019.56 |
| R3utr425 | μM | 20 | 0.27 | 0.15 | 124.20 |
| Ractin876 | μM | 20 | 0.27 | 0.15 | 124.20 |
| | | Volume mix/well (μl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B
Samples 864

| | | | | Volume for (μl) | |
|---|---|---|---|---|---|
| | | Concentration | | 1 | x |
| Mix Item | Unit | Stock | Final | sample | samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/μl | 40.00 | 1.00 | 0.50 | 432.0 |
| Expand RT | U/μl | 50.00 | 0.33 | 0.13 | 112.3 |
| | | Total Volume Mix (μl) | | 7.43 | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix C
Samples 833
Reaction Vol. (μl) 25

| | | | | Volume for (μl) | |
|---|---|---|---|---|---|
| | | Concentration | | 1 | x |
| Mix Item | Unit | Stock | Final | sample | samples |
| $H_2O$ PCR grade Roche | | | | 7.74 | 6447.42 |
| Roche 2xMM mix | X | 2 | 1 | 12.50 | 10412.50 |
| F3utr258 | μM | 20 | 0.3 | 0.38 | 316.54 |
| R3utr425 | μM | 20 | 0.3 | 0.38 | 316.54 |

TABLE 4-continued qPCR mix and protocol.

| P3utr343 | μM | 20 | 0.1 | 0.13 | 108.29 |
| Factin743 | μM | 20 | 0.3 | 0.38 | 316.54 |
| Ractin876 | μM | 20 | 0.3 | 0.38 | 316.54 |
| Pactin773 | μM | 20 | 0.1 | 0.13 | 108.29 |

| | Volume Mix/Tube (μl) | 22.02 |
| | cDNA | 3.00 |

B
Protocol qPCR3

| Step | Temp | Time | Ramp rate | |
| --- | --- | --- | --- | --- |
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$, and SI for the compounds against serotype 1 in the RT-qPCR assays Protocol A
RT-qPCR serotype 1 TC974#666

| compound# | $EC_{50}$ (μM) | N | $CC_{50}$ (μM) | N | SI | N |
| --- | --- | --- | --- | --- | --- | --- |
| 1B | 0.0015 | 4 | >2.5 | 4 | >2290 | 4 |
| 2B | 0.0060 | 5 | >2.5 | 5 | >744 | 5 |
| 3B | 0.0024 | 3 | >2.5 | 2 | >1550 | 2 |
| 4B | 0.00057 | 4 | >2.5 | 4 | >8060 | 4 |
| 5B | 0.0020 | 4 | >2.5 | 4 | >981 | 4 |
| 6A | 0.00064 | 4 | >2.5 | 4 | >10900 | 4 |
| 7B | 0.00088 | 3 | >2.5 | 3 | >6750 | 3 |
| 8A | 0.0020 | 3 | >2.5 | 3 | >1570 | 3 |
| 9B | 0.00099 | 3 | >2.5 | 3 | >2860 | 3 |
| 10B | 0.00036 | 3 | >2.5 | 3 | >8670 | 3 |
| 11B | 0.000095 | 3 | >2.5 | 3 | >41800 | 3 |
| 12A | 0.0021 | 3 | 11 | 3 | 3850 | 3 |
| 13A | 0.00012 | 3 | >2.5 | 3 | >32500 | 3 |
| 14B | 0.00022 | 3 | 2.3 | 3 | 8720 | 3 |
| 15B | 0.00013 | 3 | 4.9 | 3 | 46500 | 3 |
| 16B | 0.000092 | 3 | >1.0 | 3 | >23100 | 3 |

N = the number of independent experiments in which the compounds were tested.

TABLE 6

$EC_{50}$, $CC_{50}$, and SI for the compounds against serotype 2 in the RT-qPCR assays Protocol A
RT-qPCR serotype 2 16681

| compound# | $EC_{50}$ (μM) | N | $CC_{50}$ (μM) | N | SI | N |
| --- | --- | --- | --- | --- | --- | --- |
| 1B | 0.0024 | 3 | >2.5 | 1 | >1480 | 1 |
| 2B | 0.0021 | 3 | 4.3 | 3 | 2070 | 3 |
| 3B | 0.0014 | 3 | 13 | 3 | 5680 | 3 |
| 4B | 0.00045 | 3 | 2.4 | 3 | 6270 | 3 |
| 5B | 0.00052 | 3 | 2.8 | 3 | 6730 | 3 |
| 6A | 0.00049 | 5 | 11 | 5 | 18700 | 5 |
| 7B | 0.0019 | 3 | >2.5 | 2 | >9150 | 2 |
| 8A | 0.00038 | 3 | >0.99 | 3 | 3620 | 3 |
| 9B | 0.00047 | 3 | >2.5 | 2 | >4250 | 2 |
| 10B | 0.00015 | 3 | >1.0 | 3 | >10700 | 3 |
| 11B | 0.000059 | 3 | 5.0 | 3 | 64900 | 3 |
| 12A | 0.00042 | 3 | 14 | 3 | 19800 | 3 |
| 13A | 0.000057 | 3 | >2.5 | 3 | >53100 | 3 |
| 14B | 0.00016 | 4 | 2.6 | 3 | >9320 | 3 |
| 15B | 0.000100 | 3 | 6.3 | 4 | >22600 | 3 |
| 16B | 0.000055 | 3 | >1.0 | 3 | >44200 | 3 |

N = the number of independent experiments in which the compounds were tested.

TABLE 7

$EC_{50}$, $CC_{50}$, and SI for the compounds against serotype 3 in the RT-qPCR assays Protocol A
RT-qPCR serotype 3 H87

| compound# | $EC_{50}$ (μM) | N | $CC_{50}$ (μM) | N | SI | N |
| --- | --- | --- | --- | --- | --- | --- |
| 1B | 0.025 | 3 | >2.5 | 3 | >123 | 3 |
| 2B | 0.038 | 4 | >2.5 | 4 | >118 | 4 |
| 3B | 0.023 | 3 | >2.5 | 3 | >136 | 3 |
| 4B | 0.011 | 3 | 2.3 | 3 | 228 | 3 |
| 5B | 0.015 | 4 | >2.2 | 4 | >116 | 4 |
| 6A | 0.0081 | 4 | >2.5 | 4 | >227 | 4 |
| 7B | 0.013 | 3 | >2.5 | 3 | >259 | 3 |
| 8A | 0.015 | 3 | >2.5 | 3 | >203 | 3 |
| 9B | 0.0064 | 4 | >1.0 | 1 | >103 | 1 |
| 10B | 0.0059 | 3 | >2.5 | 3 | >414 | 3 |
| 11B | 0.0065 | 3 | >2.5 | 3 | >991 | 3 |
| 12A | 0.036 | 3 | 12 | 3 | 384 | 3 |
| 13A | 0.0018 | 3 | >2.5 | 3 | >1580 | 3 |
| 14B | 0.0055 | 3 | >2.5 | 3 | >644 | 3 |
| 15B | 0.0028 | 3 | 5.8 | 3 | 3130 | 3 |
| 16B | 0.00087 | 3 | >1.0 | 3 | >1780 | 3 |

N = the number of independent experiments in which the compounds were tested.

TABLE 8

$EC_{50}$, $CC_{50}$, and SI for the compounds against serotype 4 in the RT-qPCR assays Protocol A
RT-qPCR serotype 4 H241

| compound# | $EC_{50}$ (μM) | N | $CC_{50}$ (μM) | N | SI | N |
| --- | --- | --- | --- | --- | --- | --- |
| 1B | 0.18 | 3 | 2.2 | 2 | 10 | 2 |
| 2B | 0.15 | 3 | >2.5 | 3 | >11 | 3 |
| 3B | 0.098 | 3 | >2.5 | 2 | >25 | 2 |
| 4B | 0.076 | 3 | 1.8 | 3 | 23 | 3 |
| 5B | 0.090 | 3 | >2.5 | 2 | >33 | 2 |
| 6A | 0.060 | 6 | >2.5 | 4 | >53 | 4 |
| 7B | 0.12 | 3 | 1.1 | 3 | 10 | 3 |
| 8A | 0.056 | 3 | 1.1 | 2 | 21 | 2 |
| 9B | 0.087 | 3 | 2.5 | 3 | 27 | 3 |
| 10B | 0.032 | 3 | 1.1 | 2 | 27 | 2 |
| 11B | 0.020 | 3 | 3.3 | 3 | 184 | 3 |
| 12A | 0.10 | 3 | 5.5 | 3 | 96 | 3 |
| 13A | 0.010 | 3 | 2.6 | 3 | 251 | 3 |
| 14B | 0.023 | 3 | 1.4 | 3 | 61 | 3 |
| 15B | 0.015 | 3 | 2.3 | 3 | 174 | 3 |
| 16B | 0.0053 | 3 | 1.2 | 2 | 181 | 2 |

N = the number of independent experiments in which the compounds were tested.

The invention claimed is:

1. A compound having formula (I)

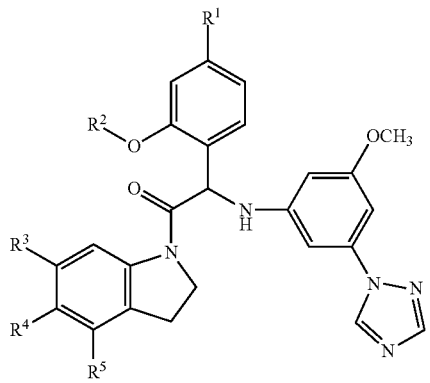

wherein
R¹ is chloro or fluoro,
R² is —CH$_2$CH$_2$OH, or C$_{3-5}$alkylCOOH;
R³ is trifluoromethyl, or trifluoromethoxy;
R⁴ is hydrogen, fluoro, or methoxy; and
R⁵ is hydrogen or methyl;
or a pharmaceutically acceptable salt, solvate or polymorph thereof.

2. A compound or its stereoisomeric form, a pharmaceutically acceptable salt, solvate or polymorph thereof according to claim 1 wherein said compound is selected from the group of

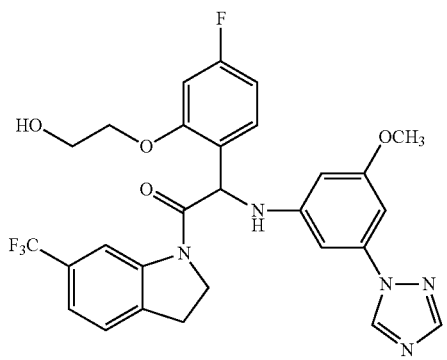

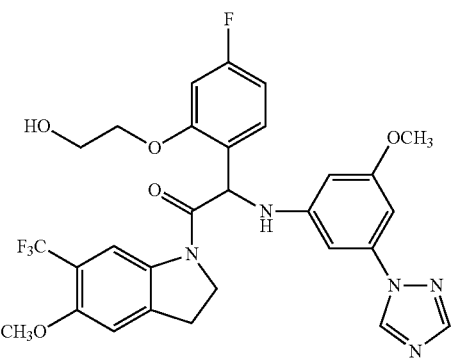

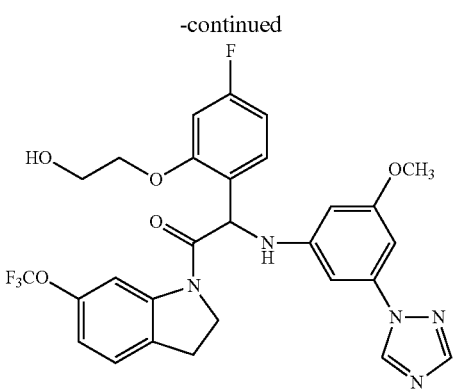

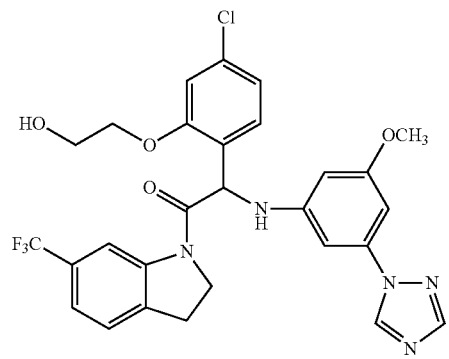

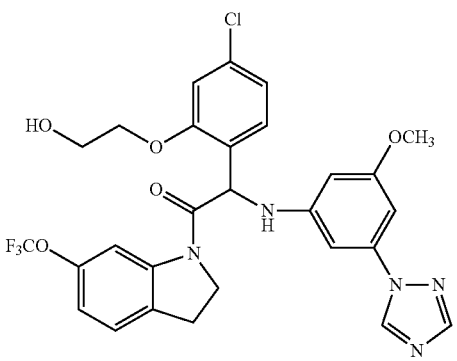

117
-continued
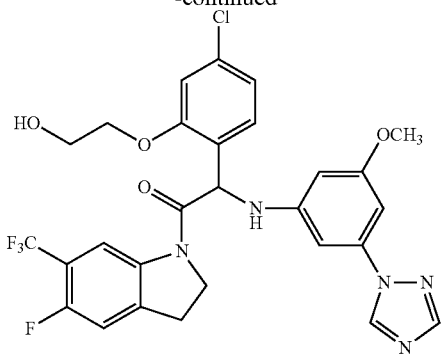
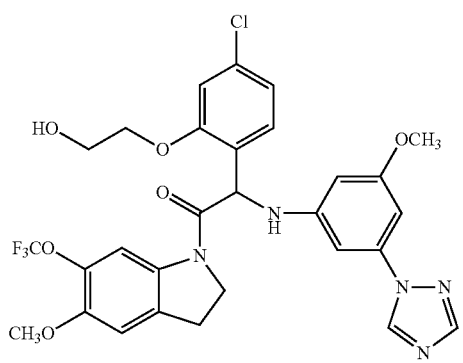
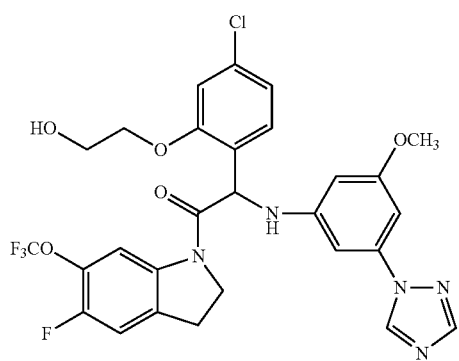
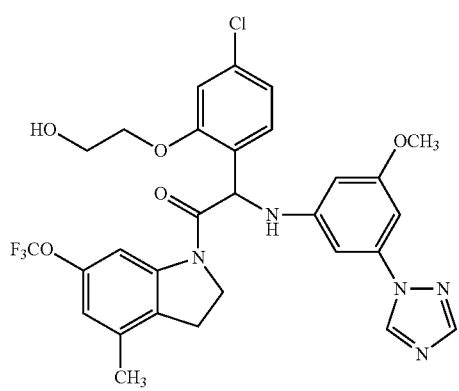
118
-continued
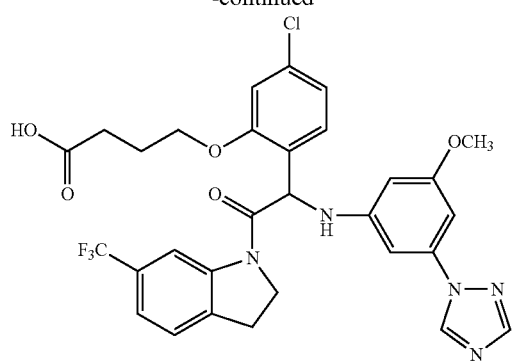
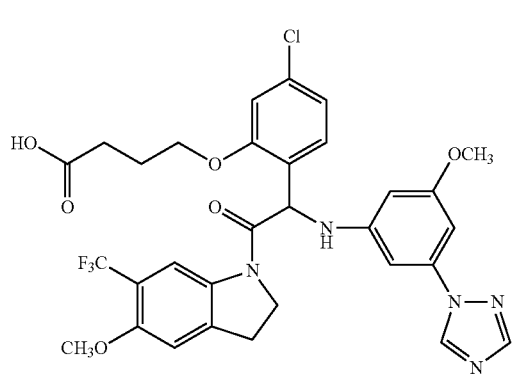
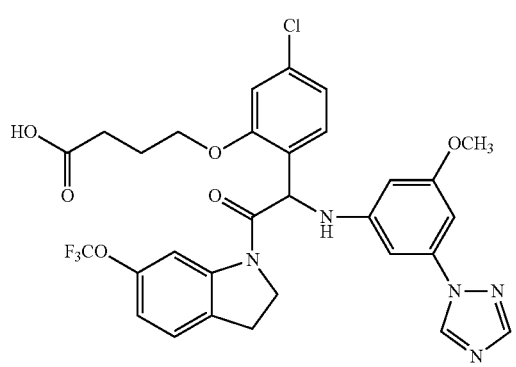
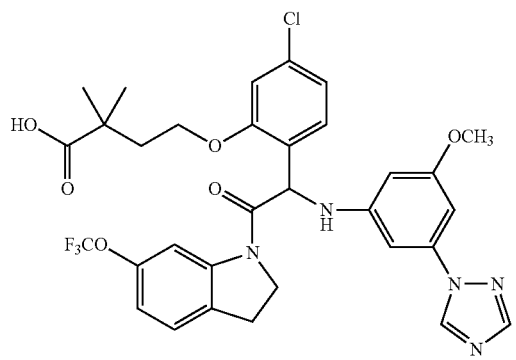

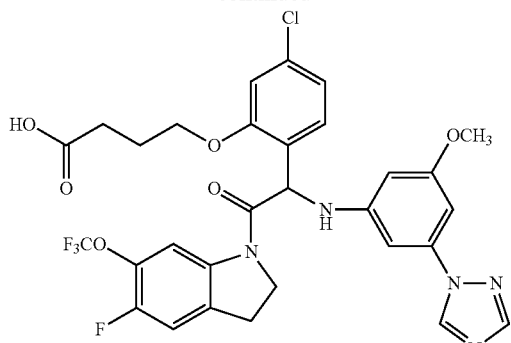
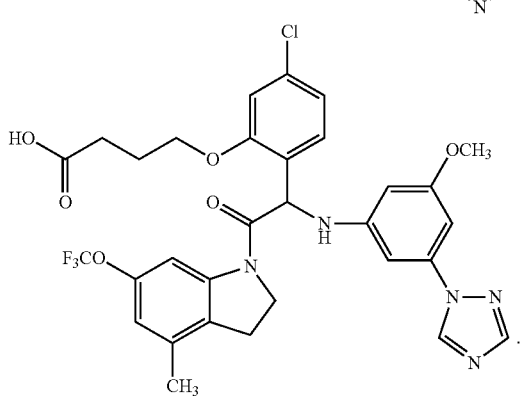
3. The compound according to claim 1 wherein said compound has the (+) specific rotation.
4. The compound according to claim 1 wherein said compound is selected from:
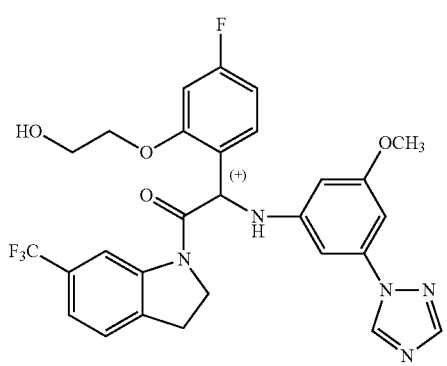
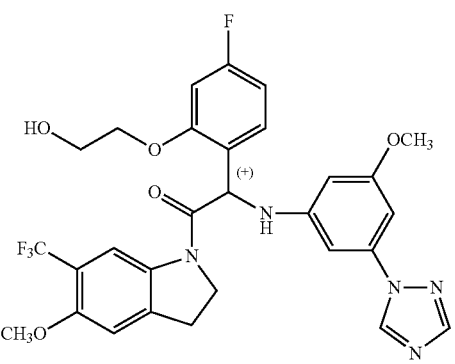
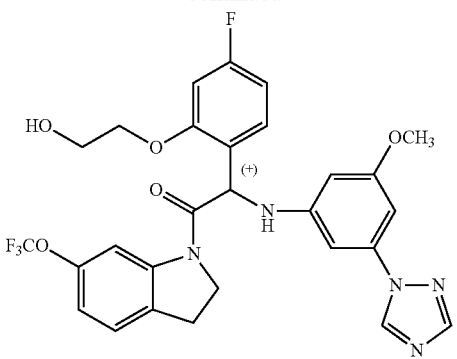
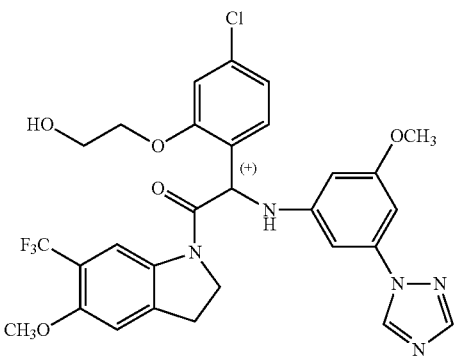
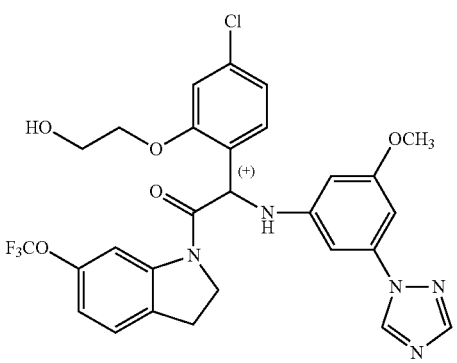

121
-continued
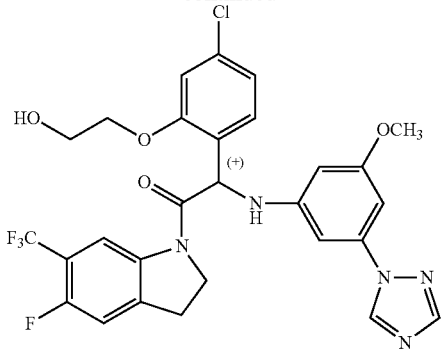
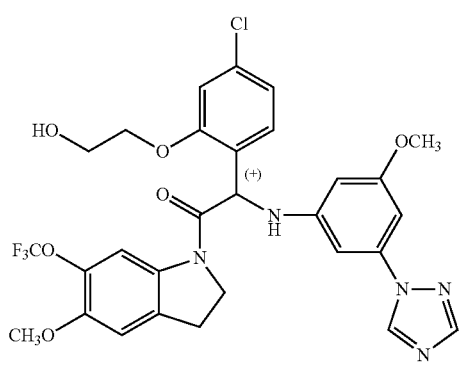
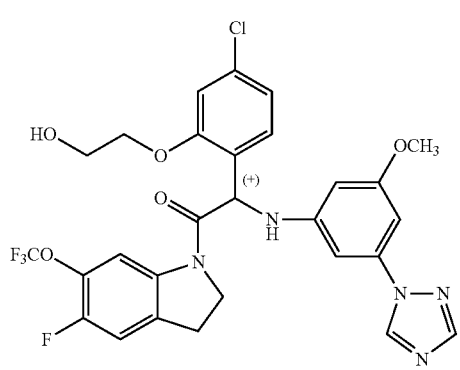
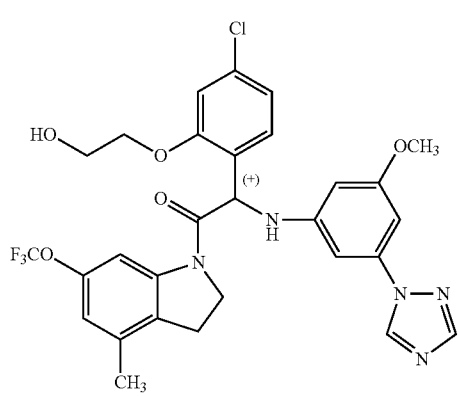
122
-continued
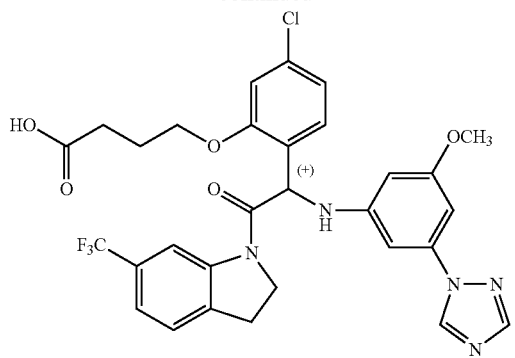
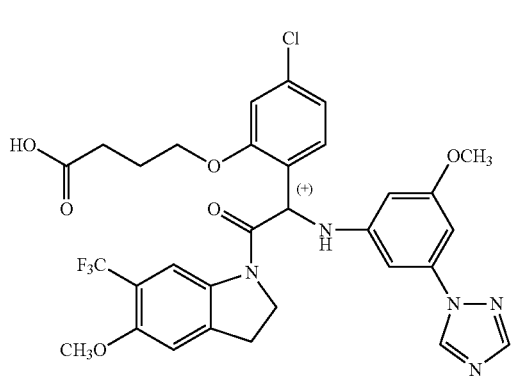
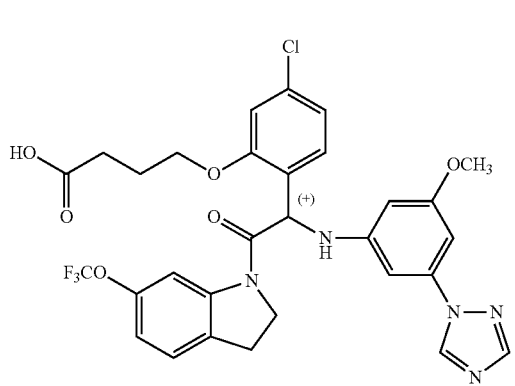
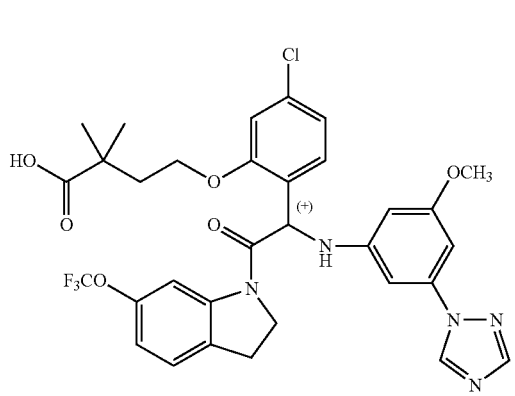

-continued

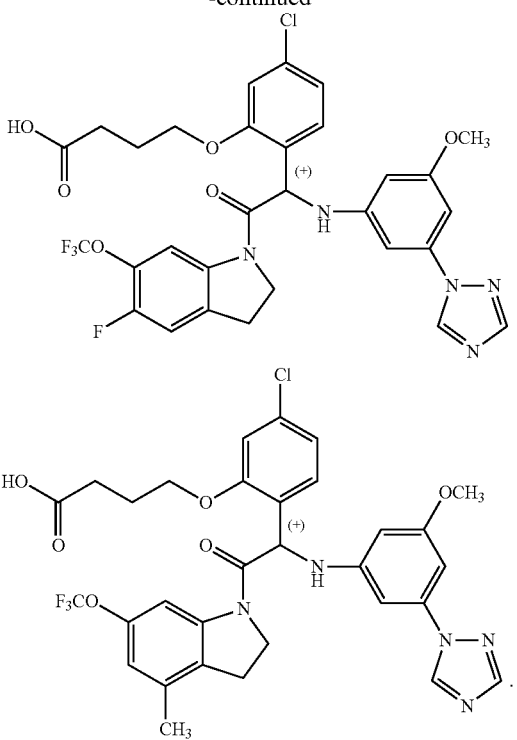

5. A pharmaceutical composition comprising a compound according to claim 1 together with one or more pharmaceutically acceptable excipients, diluents or carriers.

6. The pharmaceutical composition according to claim 5 which comprises a second or further active ingredient.

7. The pharmaceutical composition according to claim 6 wherein the second or further active ingredient is an antiviral agent.

8. A method of treating Dengue infection or a disease caused by Dengue infection, comprising administering to a patient in need thereof an effective amount of a compound of formula (I) according to claim 1.

9. The method according to claim 8 wherein the Dengue infection is an infection by viruses of the DENV-1, DENV-2, DENV-3 or DENV-4 strain.

10. A method of treating Dengue infection or a disease caused by Dengue infection comprising administering to a subject in need thereof an effective amount of the pharmaceutical composition of claim 5.

11. A method of treating Dengue infection or a disease caused by Dengue infection, comprising administering to a patient in need thereof a compound according to claim 2.

12. A method of treating Dengue infection or a disease caused by Dengue infection, comprising administering to a patient in need thereof a compound according to claim 3.

13. A method of treating Dengue infection or a disease caused by Dengue infection, comprising administering to a patient in need thereof a compound according to claim 4.

14. A method of inhibiting Dengue virus proliferation in an animal cell, comprising administering to a subject in need thereof an effective amount of the compound according to claim 1.

15. A method of inhibiting Dengue virus proliferation in an animal cell, comprising administering to a subject in need thereof an effective amount of the pharmaceutical composition according to claim 5.

* * * * *